(12) United States Patent
Bender et al.

(10) Patent No.: US 11,008,389 B2
(45) Date of Patent: May 18, 2021

(54) USES OF A DUAL V REGION ANTIBODY-LIKE PROTEIN

(71) Applicant: SANOFI, Paris (FR)

(72) Inventors: Florent C. Bender, Bedminster, NJ (US); Danxi Li, Skillman, NJ (US); Anne Minnich, Flemington, NJ (US); Amirtha Naadimuthu, Pennington, NJ (US); Ercole Rao, Morfelden-Waldorf (DE); Brian N. Swanson, Robesonia, PA (US); Lei Tang, Belle Mead, NJ (US); Haixin Yu, Scotch Plains, NJ (US); Otmane Boussif, Paris (FR); Sophie Carayon, Paris (FR)

(73) Assignee: SANOFI, Paris (FR)

(*) Notice: Subject to any disclaimer, the term of this patent is extended or adjusted under 35 U.S.C. 154(b) by 29 days.

(21) Appl. No.: 15/206,045

(22) Filed: Jul. 8, 2016

(65) Prior Publication Data
US 2017/0029498 A1  Feb. 2, 2017

Related U.S. Application Data

(63) Continuation of application No. 14/003,496, filed as application No. PCT/US2012/029147 on Mar. 15, 2012, now abandoned.

(60) Provisional application No. 61/557,635, filed on Nov. 9, 2011, provisional application No. 61/537,243, filed on Sep. 21, 2011, provisional application No. 61/453,275, filed on Mar. 16, 2011.

(30) Foreign Application Priority Data

Dec. 21, 2011 (FR) .................. 11 62177

(51) Int. Cl.
| C07K 16/24 | (2006.01) |
|---|---|
| C07K 16/46 | (2006.01) |
| A61K 39/00 | (2006.01) |
| A61K 39/395 | (2006.01) |

(52) U.S. Cl.
CPC .......... *C07K 16/247* (2013.01); *C07K 16/244* (2013.01); *A61K 2039/505* (2013.01); *C07K 16/468* (2013.01); *C07K 2317/24* (2013.01); *C07K 2317/31* (2013.01); *C07K 2317/565* (2013.01); *C07K 2317/62* (2013.01); *C07K 2317/64* (2013.01); *C07K 2317/73* (2013.01); *C07K 2317/75* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| 3,773,919 A | 11/1973 | Boswell et al. |
|---|---|---|
| 4,179,337 A | 12/1979 | Davis et al. |
| 4,256,746 A | 3/1981 | Miyashita et al. |
| 4,275,149 A | 6/1981 | Litman et al. |
| 4,294,757 A | 10/1981 | Asai |
| 4,301,144 A | 11/1981 | Iwashita et al. |
| 4,307,016 A | 12/1981 | Asai et al. |
| 4,313,946 A | 2/1982 | Powell et al. |
| 4,315,929 A | 2/1982 | Freedman et al. |
| 4,318,980 A | 3/1982 | Boguslaski et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,424,219 A | 1/1984 | Hashimoto et al. |
| 4,444,887 A | 4/1984 | Hoffmann |
| 4,450,254 A | 5/1984 | Isley et al. |
| 4,496,689 A | 1/1985 | Mitra |
| 4,560,655 A | 12/1985 | Baker |
| 4,640,835 A | 2/1987 | Shimizu et al. |
| 4,657,866 A | 4/1987 | Kumar |
| 4,670,417 A | 6/1987 | Iwasaki et al. |
| 4,676,980 A | 6/1987 | Segal et al. |
| 4,716,111 A | 12/1987 | Osband et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,397 A | 3/1989 | Boss et al. |
| 4,816,567 A | 3/1989 | Cabilly et al. |
| 4,946,778 A | 8/1990 | Ladner et al. |
| 5,122,464 A | 6/1992 | Wilson et al. |
| 5,122,469 A | 6/1992 | Mather et al. |

(Continued)

FOREIGN PATENT DOCUMENTS

| EP | 0 239 400 A2 | 9/1987 |
|---|---|---|
| EP | 0 332 424 A2 | 9/1989 |

(Continued)

OTHER PUBLICATIONS

Adey et al., Chapter 16, "Preparation of Second-Generation Phage Libraries", pp. 277-291, Phage Display of Peptides and Proteins, A Laboratory Manual, eds. Kay et al., Academic Press (1996).

(Continued)

*Primary Examiner* — Elizabeth C. Kemmerer
*Assistant Examiner* — Regina M DeBerry
(74) *Attorney, Agent, or Firm* — Morrison & Foerster LLP

(57) ABSTRACT

Uses of a dual V region antibody-like protein or a fragment of a dual V region antibody-like region.

11 Claims, 11 Drawing Sheets

Specification includes a Sequence Listing.

(56) References Cited

U.S. PATENT DOCUMENTS

| | | |
|---|---|---|
| 5,223,409 A | 6/1993 | Ladner et al. |
| 5,225,539 A | 7/1993 | Winter et al. |
| 5,314,995 A | 5/1994 | Fell, Jr. et al. |
| 5,413,923 A | 5/1995 | Kucherlapati et al. |
| 5,474,981 A | 12/1995 | Leder et al. |
| 5,475,092 A | 12/1995 | Chari et al. |
| 5,530,101 A | 6/1996 | Queen et al. |
| 5,534,617 A | 7/1996 | Cunningham et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,585,499 A | 12/1996 | Chari et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,661,016 A | 8/1997 | Lonberg et al. |
| 5,698,417 A | 12/1997 | Robinson et al. |
| 5,698,435 A | 12/1997 | Robinson et al. |
| 5,705,154 A | 1/1998 | Dalie et al. |
| 5,712,163 A | 1/1998 | Parenteau et al. |
| 5,807,715 A | 9/1998 | Morrison et al. |
| 5,814,318 A | 9/1998 | Lonberg et al. |
| 5,846,545 A | 12/1998 | Chari et al. |
| 5,869,619 A | 2/1999 | Studnicka |
| 5,885,793 A | 3/1999 | Griffiths et al. |
| 5,916,771 A | 6/1999 | Hori et al. |
| 5,928,904 A | 7/1999 | Holmes et al. |
| 5,939,598 A | 8/1999 | Kucherlapati et al. |
| 5,989,830 A | 11/1999 | Davis et al. |
| 6,048,728 A | 4/2000 | Inlow et al. |
| 6,204,023 B1 | 3/2001 | Robinson et al. |
| 6,277,375 B1 | 8/2001 | Ward |
| 6,333,410 B1 | 12/2001 | Chari et al. |
| 6,514,496 B1 | 2/2003 | Platz et al. |
| 7,612,181 B2 | 11/2009 | Wu et al. |
| 7,683,024 B2 | 3/2010 | Chan et al. |
| 8,388,965 B2 | 3/2013 | Rao et al. |
| 9,732,162 B2 | 8/2017 | Rao et al. |
| 9,738,728 B2 | 8/2017 | Rao et al. |
| 10,005,835 B2 | 6/2018 | Carayon et al. |
| 2002/0004587 A1 | 1/2002 | Miller et al. |
| 2002/0127231 A1 | 9/2002 | Schneck et al. |
| 2003/0130496 A1 | 7/2003 | Winter et al. |
| 2004/0033228 A1 | 2/2004 | Krause et al. |
| 2005/0003403 A1 | 1/2005 | Rossi et al. |
| 2006/0063228 A1 | 3/2006 | Kasaian et al. |
| 2007/0071675 A1 | 3/2007 | Wu et al. |
| 2009/0215092 A1 | 8/2009 | Love et al. |
| 2010/0226923 A1 | 9/2010 | Rao et al. |
| 2011/0206687 A1 | 8/2011 | Hickman |
| 2011/0217318 A1 | 9/2011 | Takayama et al. |
| 2012/0093830 A1 | 4/2012 | De Silva |
| 2012/0121580 A1 | 5/2012 | Bhambhani et al. |
| 2012/0251541 A1 | 10/2012 | Baurin et al. |
| 2013/0244282 A1* | 9/2013 | Schrum ............... C07K 16/00 435/69.6 |
| 2016/0075777 A1 | 3/2016 | Carayon et al. |
| 2018/0030156 A1 | 2/2018 | Rao et al. |

FOREIGN PATENT DOCUMENTS

| | | |
|---|---|---|
| EP | 0 338 745 A1 | 10/1989 |
| EP | 0 396 387 A2 | 11/1990 |
| EP | 0 413 622 A1 | 2/1991 |
| EP | 0 439 095 A2 | 7/1991 |
| EP | 0 519 596 A1 | 12/1992 |
| EP | 0 592 106 A1 | 4/1994 |
| EP | 2 222 709 A2 | 9/2010 |
| GB | 2403952 A | 1/2005 |
| GB | 2430883 B | 3/2008 |
| JP | 2011-501671 A | 1/2011 |
| WO | WO-86/05807 A1 | 10/1986 |
| WO | WO-87/05330 A1 | 9/1987 |
| WO | WO-89/01036 A1 | 2/1989 |
| WO | WO-1989/009622 A1 | 10/1989 |
| WO | WO-89/12624 A2 | 12/1989 |
| WO | WO-91/09967 A1 | 7/1991 |
| WO | WO-91/10741 A1 | 7/1991 |
| WO | WO-91/14438 A1 | 10/1991 |
| WO | WO-92/01047 A1 | 1/1992 |
| WO | WO-92/08495 A1 | 5/1992 |
| WO | WO-93/08829 A1 | 5/1993 |
| WO | WO-93/11161 A1 | 6/1993 |
| WO | WO-93/15199 A1 | 8/1993 |
| WO | WO-93/15200 A1 | 8/1993 |
| WO | WO-93/16185 A2 | 8/1993 |
| WO | WO-93/21232 A1 | 10/1993 |
| WO | WO-1993/021319 A1 | 10/1993 |
| WO | WO-94/25591 A1 | 11/1994 |
| WO | WO-96/33735 A1 | 10/1996 |
| WO | WO-96/34096 A1 | 10/1996 |
| WO | WO-97/14719 A1 | 4/1997 |
| WO | WO-97/33899 A1 | 9/1997 |
| WO | WO-97/34631 A1 | 9/1997 |
| WO | WO-97/34911 A1 | 9/1997 |
| WO | WO-98/16654 A1 | 4/1998 |
| WO | WO-98/23289 A1 | 6/1998 |
| WO | WO-98/24893 A2 | 6/1998 |
| WO | WO-98/46645 A2 | 10/1998 |
| WO | WO-98/50433 A2 | 11/1998 |
| WO | WO-2000/64944 A1 | 11/2000 |
| WO | WO-2001/77137 A1 | 10/2001 |
| WO | WO-2001/077342 A1 | 10/2001 |
| WO | WO-2001/090192 A2 | 11/2001 |
| WO | WO-2002/08293 A2 | 1/2002 |
| WO | WO-2003/035847 A2 | 5/2003 |
| WO | WO-2003/038041 A2 | 5/2003 |
| WO | WO-2003/092610 A2 | 11/2003 |
| WO | WO-2004/016286 A2 | 2/2004 |
| WO | WO-2005/007690 A1 | 1/2005 |
| WO | WO-2005/007699 A2 | 1/2005 |
| WO | WO-2005/062967 A2 | 7/2005 |
| WO | WO-2005/076990 A2 | 8/2005 |
| WO | WO-2005/083440 A2 | 9/2005 |
| WO | WO-2005/085284 A1 | 9/2005 |
| WO | WO-2005/113605 A1 | 12/2005 |
| WO | WO-2005/116077 A2 | 12/2005 |
| WO | WO-2005/123126 A2 | 12/2005 |
| WO | WO-2006/042333 A2 | 4/2006 |
| WO | WO-2007/045477 A2 | 4/2007 |
| WO | WO-2007/080174 A2 | 7/2007 |
| WO | WO-2007/085815 A2 | 8/2007 |
| WO | WO-2007/107349 A1 | 9/2007 |
| WO | WO-2008/086395 A2 | 7/2008 |
| WO | WO-2009/051837 A2 | 4/2009 |
| WO | WO-2009/052081 A2 | 4/2009 |
| WO | WO-2009/068649 A2 | 6/2009 |
| WO | WO-2009/070642 A1 | 6/2009 |
| WO | WO-2010/066762 A1 | 6/2010 |
| WO | WO-2012/125775 A1 | 9/2012 |
| WO | WO-2014177568 A1 * | 11/2014 ........... C07K 16/244 |

OTHER PUBLICATIONS

Almawi et al., "Clinical review 103: T helper type 1 and 2 cytokines mediate the onset and progression of type I (insulin-dependent) diabetes." The Journal of Clinical Endocrinology & Metabolism 84(5): 1497-502 (1999).

Amit et al., "Three-dimensional structure of an antigen-antibody complex at 2.8 A resolution," 233(4765) Science 747-53 (1986).

Altschul et al., "Basic local alignment search tool," J Mol Biol 215(3):403-410 (1990).

American Diabetes Association. Standards of medical care in diabetes—2009; Diabetes Care. 2009; 32 Suppl 1:S13-61.

Andrew et al., "Comparison of in Vitro Cell Binding Characteristics of Four Monoclonal Antibodies and Their Individual Tumor Localization Properties in Mice." Cancer Research 50:4423-28 (1990).

Aplin & Wriston, "Preparation, properties, and applications of carbohydrate conjugates of proteins and lipids," 10 (4) CRC Crit Rev Biochem 259-306 (1981).

(56) References Cited

OTHER PUBLICATIONS

Arnon et al., "Monoclonal Antibodies for Immunotargeting of Drugs in Cancer Therapy" in Monoclonal Antibodies and Cancer Therapy: Proceedings of the Roche-UCLA Symposium, 243-56 (Reisfeld and Sell eds., 1985).
Aversa et al., "An interleukin 4 (IL-4) mutant protein inhibits both IL-4 or IL-13-induced human immunoglobulin G4 (IgG4) and IgE synthesis and B cell proliferation: support for a common component shared by IL-4 and IL-13 receptors," J Exp Med 178(6): 2213-18 (1993).
Barbas et al., "In vitro evolution of a neutralizing human antibody to human immunodeficiency virus type 1 to enhance affinity and broaden strain cross-reactivity," 91(9) Proc Nat'l Acad Sci USA 3809-13 (1994).
Barbas et al., "Assembly of combinatorial antibody libraries on phage surfaces: the gene III site," 88(18) Proc Nat'l Acad Sci USA 7978-82 (1991).
Barnes et al., "Methods for growth of cultured cells in serum-free medium," 102(2) Anal Biochem 255-70 (1980).
Bass et al., "Hormone phage: an enrichment method for variant proteins with altered binding properties," 8(4) Proteins 309-14 (1990).
Biolegend: "Purified anti-human IL-4", Product Data Sheet, Nov. 30, 2012 (Nov. 30, 2012), Retrieved from the Internet: URL:http://www.biolegend.com/purified-anti-human-il-4-antibody-1 018.html [retrieved on Feb. 11, 2013].
Birch & Racher, "Antibody production," 58(5-6) Adv Drug Del Rev 671-685 (2006).
Bird et al, "Single-chain antigen-binding proteins," 242(4877) Science 423-6 (1988).
Boder et al., "Directed evolution of antibody fragments with monovalent femtomolar antigen-binding affinity," 97(20) Proc Nat' l Acad Sci USA 10701-5 (2000).
Bodey et al., "Failure of cancer vaccines: the significant limitations of this approach to immunotherapy", Anticancer Research 20(4):2665-76 (2000).
Boerner et al., "Production of antigen-specific human monoclonal antibodies from in vitro-primed human splenocytes," 147(1) J Immunol 86-95 (1991).
Brennan et al., "Preparation of bispecific antibodies by chemical recombination of monoclonal immunoglobulin G1 fragments," Science 229(4708): 81-83 (1985).
Brodeur et al., "Mouse-Human Myeloma Partners for the Production of Heterohybridomas," in Monoclonal Antibody Production Techniques and Applications, Chapter4:51-63 (LB Schook ed. 1st ed. 1987).
Brooks et al., "CHARMM: A program for macromolecular energy, minimization, and dynamics calculations," 4(2) J Computational Chemistry 187-217 (1983).
Broti et al., "Biomarkers of drug-induced vascular injury." Toxicol Appl PharmacoL 207(2 Suppl):441-45 (2005).
Brüggemann et al., "Designer mice: the production of human antibody repertoires in transgenic animals," 7 Year in Immunol 33-40 (1993).
Buchwald et al., "Long-term, continuous intravenous heparin administration by an implantable infusion pump in ambulatory patients with recurrent venous thrombosis," 88(4) Surgery 507-16 (1980).
Calabrese & Duna, "Drug-induced vasculitis." Curr Opin Rheumatol 8(1):34-40 (1996).
Caron et al., "Engineered humanized dimeric forms of IgG are more effective antibodies," 176(4) J Exp Med 1191-5 (1992).
Carter et al., Toward the production of bispecific antibody fragments for clinical applications, J Hematother 4 (5):463-70 (1995).
Carter, "Bispecific human IgG by design," J Immunol Methods 248(1-2):7-15 (2001).
Carter et al., "Humanization of an anti-p185HER2 antibody for human cancer therapy," Proc Nat'l Acad Sci USA 89 (10):4285-89 (1992).
Carter et al., "High level *Escherichia coli* expression and production of a bivalent humanized antibody fragment," 10 (2) Biotechnology 163-7 (1992).
Case et al., "The Amber biomolecular simulation programs," 26(16) J Computational Chemistry 1668-88 (2005).
Casset et al., "A peptide mimetic of an anti-CD4 monoclonal antibody by rational design" Biochemical and Biophysical Research Communication 307:198-205 (2003).
Cekmen et al., "Vascular endothelial growth factor levels are increased and associated with disease activity in patients with Behçet's syndrome." Int. J. Dermatol. 42(11):870-75 (2003).
Chan et al., "MEDUSA: An innovative formulation approach to improve pharmacokinetic and safety profiles of biotherapeutics", ONdrugDelivery, pp. 4-6 (Jan. 2011).
Chang et al., "Phenotypic expression in $E\_$ *coli* of a DNA sequence coding for mouse dihydrofolate reductase," 275 (5681) Nature 615-24 (1978).
Chatterjee et al., "Idiotypic antibody immunotherapy of cancer", Cancer Immunology and Immunotherapy 38 (2):75-82 (1994).
Chothia et al., "Canonical structures for the hypervariable regions of immunoglobulins," J Mol Biol 196(4):901-17 (1987).
Clackson et al., "Making antibody fragments using phage display libraries," 352(6336) Nature 624-28 (1991).
Clyne & Olshaker, "The C-reactive protein." J. Emerg. Med. 17(6):1019-25 (1999).
Cockett et al., "High level expression of tissue inhibitor of metalloproteinases in Chinese hamster ovary cells using glutamine synthetase gene amplification," 8(7) Biotechnology 662-7 (1990).
Colbére-Garapin et al., "A new dominant hybrid selective marker for higher eukaryotic cells," 150(1) J Mol Biol 1-14(1981).
Coppola et al., "Enforced expression of KDR receptor promotes proliferation, survival and megakaryocytic differentiation ofTF1 progenitor cell line," Cell Death Differ. 13(1):61-74 (Jan. 2006).
Cote et al., "Generation of human monoclonal antibodies reactive with cellular antigens," 80(7) Proc Nat'l Acad Sci USA 2026-39 (1983).
Creighton, Proteins: Structure and Molecular Properties, W.H. Freeman &Co., New York, pp. 78-87 (1st Edition, 1984).
Crouse et al., "Expression and amplification of engineered mouse dihydrofolate reductase minigenes," 3(2) Mal Cell Biol 257-66 (1983).
Cunningham & Wells, "High-resolution epitope mapping of hGH-receptor interactions by alanine-scanning mutagenesis," 244(4908) Science 1081-5 (1989).
Cunningham & Wells, "Rational design of receptor-specific variants of human growth hormone," 88(8) Proc Nat'l Acad Sci USA 3407-11 (1991).
Cwirla et al., "Peptides on phage: a vast library of peptides for identifying ligands," 87(16) Proc Nat'l Acad Sci USA 6378-82 (1990).
Daugherty et al., "Formulation and delivery issues for monoclonal antibody therapeutics", Advanced Drug Delivery Reviews, 58(5-6):686-706 (Aug. 2006).
Davies & Riechmann, "Affinity improvement of single antibody VH domains: residues in all three hypervariable regions affect antigen binding," 2(3) Immunotechnology 169-79 (1996).
Definition of "Treating" or "To Treat," The American Heritage® Medical Dictionary (2007), retrieved Aug. 3, 2015 from http://medical-dictionaryJhefreedictionary.com/treating pp. 1-3.
Defrance et al., "Interleukin 13 is a B cell stimulating factor," J Exp Med 179(1):135-43 (1994).
Derocq et al., "Interleukin-13 stimulates interleukin-6 production by human keratinocytes. Similarity with interleukin-4," FEBS Lett 343(1):32-36 (1994).
De Rosa & Agnello "Observations on cryoglobulin testing: I. The association of cryoglobulins containing rheumatoid factors with manifestation of cryoglobulinemic vasculitis." J. Rheumatol. 36(9):1953-55 (2009).
De Gruijl & Curiel, "Cancer vaccine strategies get bigger and better" Nature Medicine 5(10):1124-25 (1999).

(56) References Cited

OTHER PUBLICATIONS

De Waal Malefyt et al., "Effects of IL-13 on phenotype, cytokine production, and cytotoxic function of human monocytes_ Comparison with IL-4 and modulation by IFN-gamma or IL-10," J Immunol 151 (11):6370-381 (1993).
Dekruif & Logtenberg, "Leucine zipper dimerized bivalent and bispecific scFv antibodies from a semi-synthetic antibody phage display library," 270(13) J Biol Chem 7630-4 (1996).
Dermer, G.B. "Another anniversary for the war on cancer." Bio/Technology, 12(3):320 (1994).
Devlin et al., "No excess of homozygosity at loci used for DNA fingerprinting," 249(4975) Science 1416-20 (1990).
Diaclone: "Diaclone Monoclonal Antibody Cataloge 2004-2005", pp. 1-28, 2004.
Donnelly, "Cancer vaccine targets leukemia", Nature Medicine 9(11):1354-56 (2003).
Doyle et al., "Interleukin-13 alters the activation state of murine macrophages in vitro: comparison with interleukin-4 and interferon-gamma," Eur J Immunol 24(6):1441-45 (1994).
Duchosal et al., "Immunization of hu-PBL-SCID mice and the rescue of human monoclonal Fab fragments through combinatorial libraries," 355(6357) Nature 258-62 (1992).
During et al., "Controlled release of dopamine from a polymeric brain implant: in vivo characterization," 25(4) Ann Neurol 351-6 (1989).
Edge et al., "Deglycosylation of glycoproteins by trifluoromethanesulfonic acid," 118(1) Anal Biochem 131-7 (1981).
Ezzell, "Cancer 'Vaccines': An Idea Whose Time Has Come'?", J NIH Research 7:46-49 (1995).
Fell et al., "Genetic construction and characterization of a fusion protein consisting of a chimeric F(ab') with specificity for carcinomas and human IL-2," 146(7) J Immunol 2446-52 (1991).
Fior et al., "Interleukin-13 gene expression by malignant and EBV-transformed human B lymphocytes," Eur Cytokine Network 5(6):593-600 (1994).
Fleer et al., "High-level secretion of correctly processed recombinant human interleukin-1 beta in Kluyveromyces lactis," 107(2) Gene 285-95 (1991).
Foecking et al., "Powerful and versatile enhancer-promoter unit for mammalian expression vectors," 45(1) Gene 101-5 (1986).
Forni et al., "Immunoprevention of cancer: is the time ripe?," Cancer Research 60(10):2571-75 (2000).
Freedberg et al., "Flexibility and Function in HIV Protease: Dynamics of the HIV-1 Protease Bound to the Asymmetric Inhibitor Kynostatin 272 (KNI-272)," 120(31) J Am Chem Soc 7916-23 (1998).
Freshney, R.I. Culture of Animal Cells, A Manual of Basic Technique, pp. 3-4; Alan R Liss, Inc, New York (1983).
Furukawa et al., "A role of the third complementarity-determining region in the affinity maturation of an antibody," 276(29) J Biol Chem 27622-8 (2001).
Gauvreau et al., "Effects of interleukin-13 blockade on allergen-induced airway responses in mild atopic asthma." American Journal of Respiratory and Critical Care Medicine, 183(8): 1007-14 (2011).
Garrard et al., "Fab assembly and enrichment in a monovalent phage display system," 9(12) Biotechnology 1373-7 (1991).
Gentz et al., "Bioassay for trans-activation using purified human immunodeficiency virus tat-encoded protein: trans-activation requires mRNA synthesis," 86(3) Proc Nat'l Acad Sci USA 821-4 (1989).
George & Hutson, The Antibodies; Chapter 6—Bispecific Antibody Engineerin 4:99-141 (Zanetti & Capra, Ed., Harwood Academic Publishers, 1997).
Gillies et al., "High-level expression of chimeric antibodies using adapted cDNA variable region cassettes," J Immunol Methods 125(1-2):191-202 (1989).
Gillies et al., "Antibody-targeted interleukin 2 stimulates T-cell killing of autologous tumor cells," 89(4) Proc Nat'l Acad Sci USA 1428-32 (1992).

Goding, "Production of Monoclonal Antibodies," in Monoclonal Antibodies: Principles and Practice, Chapter3:59-103 (2nd Ed., 1986).
Goeddel et al., "Direct expression in *Escherichia coli* of a DNA sequence coding for human growth hormone," 281 (5732) Nature 544-8 (1979).
Goeddel et al., "Synthesis of human fibroblast interferon by *E. coli*," 8(18) Nucl Acids Res 4057-74 (1980).
Gordon & Martinez. "Alternative activation of macrophages: mechanism and functions." Immunity 32(5):593-604 (2010).
Gough et al., "Assessment of Dose Proportionality: Report from the Statisticians in the Pharmaceutical Industry/ Pharmacokinetics UK Joint Working Party" Therapeutic Innovation & Regulatory Science 29(3):1039-1048 (1995).
Gram et al., "In vitro selection and affinity maturation of antibodies from a naive combinatorial immunoglobulin library," 89(8) Proc Nat'l Acad Sci USA 3576-80 (1992).
Grünberg et al., "Flexibility and conformational entropy in protein-protein binding," 14(12) Structure 683-93 (2006).
Guidance for industry: toxicity grading scale for healthy adult and adolescent volunteers enrolled in preventive vaccine clinical trials, US Dept of Health and Human Services, Food and Drug Administration, Center for Biologics Evaluation and Research, Sep. 2007.
Guss et al., "Structure of the IgG-binding regions of streptococcal protein G," 5(7) EMBO J 1567-75 (1986).
Hakimuddin et al., "A chemical method for deglycosylation of proteins," 259(1) Arch Biochem Biophys 52-7 (1987).
Ham & McKeehan, "Media and growth requirements," 58 Meth Enzymol 44-93 (1979).
Hansel et al., "The safety and side effects of monoclonal antibodies." Nat Rev Drug Discov. 9(4):325-38 (2010).
Harris et al., "Commercial manufacturing scale formulation and analytical characterization of therapeutic recombinant antibodies," 61(3) Drug Dev Res 137-54 (2004).
Hart et al., "Preclinical efficacy and safety of pascolizumabe (SB 240683): A humanized anti-interleukin-4 antibody with therapeutic potential in asthma," Clinical and Experimental Immunology 103(1) 93-100 (2002).
Hawkins et al., "Selection of phage antibodies by binding affinity: Mimicking affinity maturation," 226(3) J Mol Biol 889-96 (1992).
Heathcote et al., "Prevalence and duration of exercise induced albuminuria in healthy people." Clin Invest Med. 32 (4):E261-65 (2009).
Heinzmann et al., "Genetic variants of IL-13 signalling and human asthma and atopy," Hum Mol Genet 9(4):549-59 (2000).
Heinzmann et al., "Genetic variants of IL-13 signalling and human asthma and atopy," 9(4) Hum Mol Genet 549-59 (2000).
Hellström et al., "Antibodies for Drug Delivery," in Controlled Drug Delivery: Fundamentals and Applications, Chapter 15:623-53 (Robinson & Lee eds., 2nd ed. 1987).
Herbert et al., "IL-4 and IL-13 exhibit comparable abilities to reduce pyrogen-induced expression of procoagulant activity in endothelial cells and monocytes," FEBS Lett 328(3):268-70 (1993).
Hinnen et al., "Transformation of yeast," 75(4) Proc Nat' l Acad Sci USA 1929-33 (1978).
Hesselink et al., "Profiles of the acute-phase reactants C-reactive protein and ferritin related to the disease course of patients with systemic lupus erythematosus-" Scand J Rheumatol. 32(3):151-55 (2003).
Hitzeman et al., "Isolation and characterization of the yeast 3-phosphoglycerokinase gene (PGK) by an immunological screening technique," 255(24) J Biol Chem 12073-80 (1980).
Holland & Holland, "Isolation and identification of yeast messenger ribonucleic acids coding for enolase, glyceraldehyde-3-phosphate dehydrogenase, and phosphoglycerate kinase," 17(23) Biochemistry 4900-7 (1978).
Holliger et al., ""Diabodies": small bivalent and bispecific antibody fragments," 90(14) Proc Nat'l Acad Sci USA 6444-8 (1993).
Howard et al., "Intracerebral drug delivery in rats with lesion-induced memory deficits," 71(1) J Neurosurg 105-12 (1989).
Hudson, "Recombinant antibody constructs in cancer therapy," Current Opinion in Immunology 11(5):548-57 (1999).

(56) References Cited

OTHER PUBLICATIONS

Hudson & Kortt, "High avidity scFv multimers; diabodies and triabodies," 231(1-2) J Immunol Methods 177-89 (1999).
Huston et al., "Protein engineering of antibody binding sites: recovery of specific activity in an anti-digoxin single-chain Fv analogue produced in *Escherichia coli*," 85(16) Proc Nat'l Acad Sci USA 5879-83 (1988).
The International Search Report from ISA for International Application No. PCT/EP2015/052899; dated Apr. 22, 2015, pp. 1-7.
The International Search Report from ISA for International Application No. PCT/EP2014/058733; dated Jul. 23, 2014, pp. 1-8.
The International Search Report for International Application No. PCT/US2012/029147 dated Jun. 29, 2012, pp. 1-5.
The International Preliminary Report on Patentability for International Application No. PCT/US2012/029147 dated Sep. 17, 2013, pp. 1-7.
Jackson et al., "Review series on helminths, immune modulation and the hygiene hypothesis: Immunity against helminths and immunological phenomena in modern human populations: coevolutionary legacies?" Immunology 126 (1):18-27 (2008).
Jakubzick et al., Human pulmonary fibroblasts exhibit altered interleukin-4 and interleukin-13 receptor subunit expression in idiopathic interstitial pneumonia—Am J. Pathol. 164(6):1989-2001 (2004).
Jakobovits et al., "Analysis of homozygous mutant chimeric mice: deletion of the immunoglobulin heavy-chain joining region blocks B-cell development and antibody production," 90(6) Proc Nat'l Acad Sci USA 2551-5 (1993).
Jakobovits et al., "Germ-line transmission and expression of a human-derived yeast artificial chromosome," 362 (6417) Nature 255-8 (1993).
James et al. "Antibody multi specificity mediated by conformational diversity," 299(5611) Science 1362-7 (2003).
Jespers et al., "Guiding the selection of human antibodies from phage display repertoires to a single epitope of an antigen," 12(9) Biotechnology 899-903 (1994).
Jones et al., "Replacing the complementarity-determining regions in a human antibody with those from a mouse," 321 (6069) Nature 522-5 (1986).
Kasaian et al., "Efficacy of IL-13 Neutralization in a SheEP-Model of Experimental Asthma", American Journal of Respiratory Cell and Molecular Biology, 36(3):368-376 (2007).
Kim & Kim, Elevation of cardiac troponin I in the acute stage of Kawasaki disease. Pediatr Cardiel. 20(3):184-88 (1999).
Köhler, "Immunoglobulin chain loss in hybridoma lines," 77(4) Proc Nat'l Acad Sci USA 2197-9 (1980).
Köhler & Milstein, "Continuous cultures of fused cells secreting antibody of predefined specificity." Nature 256 (5517):495-97 (1975).
Kontiinen et al., "Roadmap to vasculitis: a rheumatological treasure hunt: Part III. Laboratory evaluation and imaging-" Indian Journal of Rheumatology 2(3):100-4 (2007).
Kostelny et al., "Formation of a bispecific antibody by the use of leucine zippers," 148(5) J Immunol 1547-53 (1992).
Kozbor & Roder, The production of monoclonal antibodies from human lymphocytes, 4(3) Immunology Today 72-9 (1983).
Kozbor et al., "A human hybrid myeloma for production of human monoclonal antibodies," 133(6) J Immunol 3001-5 (1984).
Kufer et al., "A revival of bispecific antibodies," 22(5) Trends Biotech 238-44 (2004).
Kundu et al., "Dynamics of proteins in crystals: comparison of experiment with simple models," 83(2) Biophys J 723-32 (2002).
Kunkel, "Rapid and efficient site-specific mutagenesis without phenotypic selection," 82(2) Proc Nat'l Acad Sci USA 488-92 (1985).
Kurzrock et al., "A Phase I Study of CNTO 328. An Anti-Interelukin-6 Monoclonal Antibody in Patients with A-Cell Non-Hodgkin's Lymphoma. Multiple Myeloma, or Castleman's Disease." Blood (ASH Annual Meeting Abstracts) 112 (11):371-72 (2008).

Kushner et al. "What does minor elevation of C-reactive protein signify?" Am J Med. 119(2):166.e17-28 (2006).
Kutemeier et al., "Assembly of humanized antibody genes from synthetic oligonucleotides using a single-round PCR," 17(2) Bio. Techniques 242-6 (1994).
Langer, "New methods in drug delivery," 249(4976) Science 1527-33 (1990).
Langer & Peppas, "Chemical and Physical Structure of Polymers as Carriers for Controlled Release of Bioactive Agents: A Review," C23(1) J Macromol Sci Rev Macromol Chem 61-126 (1983).
Lazar et al., "A molecular immunology approach to antibody humanization and functional optimization," Mol Immunol 44(8):1986-88 (2007).
Lee et al., "Increased vaccine-specific T cell frequency after peptide-based vaccination correlates with increased susceptibility to in vitro stimulation but does not lead to tumor regression" Journal of Immunology 163(11): 6292-6300 (1999).
Lefort et al., "IL-13 and IL-4 share signal transduction elements as well as receptor components in TF-1 cells," FEBS Lett 366(1-2):122-26 (1995).
Levy et al., "Inhibition of calcification of bioprosthetic heart valves by local controlled-release diphosphonate," 228 (4696) Science 190-2 (1985).
Lindmark et al., "Binding of immunoglobulins to protein A and immunoglobulin levels in mammalian sera," 62(1) J Immunol Methods 1-13 (1983).
Liu et al., "Characterization of the stability of a fully human monoclonal IgG after prolonged incubation at elevated temperature," 837(1-2) J Chromatog B 35-43 (2006).
Lonberg & Huszar, "Human antibodies from transgenic mice," 13(1) Int Rev Immunol 65-93 (1995).
Lopez-Berestein, Treatment of Systemic Fungal Infections with Liposomal-Amphotericin B, in Liposomes in the Therapy of Infectious Disease and Cancer, 317-27 (Lopez-Berestein et al., eds., 1989).
Lowman & Wells, "Affinity maturation of human growth hormone by monovalent phage display," 234(3) J Mal Biol 564-78 (1993).
Lowman et al., "Selecting high-affinity binding proteins by monovalent phage display," 30(45) Biochemistry 10832-8 (1991).
Lowy et al., "Isolation of transforming DNA: cloning the hamster aprt gene," 22(3) Cell 817-23 (1980).
Lu et al., "Di-diabody: a novel tetravalent bispecific antibody molecule by design," J. Immunol. Methods 279 (1-2):219-32 (2003).
Lu et al., "Simultaneous blockade of both the epidermal growth factor receptor and the insulin-like growth factor receptor signaling pathways in cancer cells with a fully human recombinant bispecific antibody." J Biol Chem. 279(4):2856-65 (2004).
Lu et al., "A fully human recombinant IgG-like bispecific antibody to both the epidermal growth factor receptor and the insulin-like growth factor receptor for enhanced antitumor activity," J. Biol. Chem. 280(20):19665-72 (2005).
Luckow & Summers, "Trends in the development of baculorvirus expression vectors," 6 Nature Biotechnology 47-55 (1988).
Ma et al., "Multiple diverse ligands binding at a single protein site: A matter of pre-existing populations," 11(2) Protein Science 184-7 (2002).
Mack et al., "A small bispecific antibody construct expressed as a functional single-chain molecule with high tumor cell cytotoxicity," 92(15) Proc Nat'l Acad Sci USA 7021-5 (1995).
Mackerell et al., "CHARMM: The Energy Function and Its Parameterization," The Encyclopedia of Computational Chemistry, vol. 1 :271-177 (Schleyer et al., eds. 1998).
Macy et al., "Variability in the measurement of C-reactive protein in healthy subjects: implications for reference intervals and epidemiological applications." Clin Chem. 43(1):52-58 {1997).
Maeda et al., "Production of human alpha-interferon in silkworm using a baculovirus vector," 315(6020) Nature 592-4 (1985).
Mallender & Voss, "Construction, expression, and activity of a bivalent bispecific single-chain antibody," 269(1) J Biol Chem 199-206 (1994).
Marks et al., "By-passing immunization: Human antibodies from V-gene libraries displayed on phage," 222(3) J Mol Biol 581-97 (1991).

(56) References Cited

OTHER PUBLICATIONS

Marks et al., "By-passing immunization: building high affinity human antibodies by chain shuffling," 10(7) Biotechnology 779-83 (1992).

McCafferty et al., "Phage antibodies: filamentous phage displaying antibody variable domains," 348(6301) Nature 552-4 (1990).

McKenzie et al., "Interleukin 13, a T-cell-derived cytokine that regulates human monocyte and B-cell function," Proc Nat'l Acad Sci USA 90(8):3735-39 (1993).

Melzack, The McGill Pain Questionnaire: major properties and scoring methods. Pain 1:277-99 (1975).

Miller et al., "Design, construction, and in vitro analyses of multivalent antibodies," J Immunol 170(9):4854-61 (2003).

Miller et al., "An Insect Baculovirus Host-vector System for High-level Expression of Foreign Genes," Genetic Engineering: Principles and Methods, vol. 8:277-98 (Setlow and Hollaender, eds., 1986).

Milstein & Cuello, "Hybrid hybridomas and their use in immunohistochemistry," Nature 305(5934):537-40 (1983).

Minty et al., "Interleukin-13 is a new human lymphokine regulating inflammatory and immune responses," Nature 362 {6417):248-50 (1993).

Minty, "Interleukin-13" in Cytokines in Health and Disease, Chapter 13:185-97 (Remick and Friedland, eds., 2nd ed. 1997).

Montaner et al., "Interleukin 13 inhibits human immunodeficiency virus type 1 production in primary blood-derived human macrophages in vitro," J Exp Med 178(2):743-47 {1993).

Morimoto & Inouye, "Single-stEP-purification of F(ab')2 fragments of mouse monoclonal antibodies (immunoglobulins G1) by hydrophobic interaction high performance liquid chromatography using TSKgel Phenyl-5PW ," 24(1-2) J Biochem Biophys Methods 107-17 (1992).

Muller et al., "The first constant domain (CH1 and CL) of an antibody used as heterodimerization domain for bispecific miniantibodies." FEBS Letters 422:259-64 (1998).

Morrison, "Transfectomas provide novel chimeric antibodies," Science 229(4719):1202-207 (1985).

Morrison et al., "Chimeric human antibody molecules: mouse antigen-binding domains with human constant region domains," Proc Nat'l Acad Sci USA 81 (21):6851-55 (1984).

Murata et al., "Sharing of receptor subunits and signal transduction pathway between the IL-4 and IL-13 receptor system," Int J Hematol 69(1):13-20 (1999).

Murray et al., "Hyper-responsiveness of IPF/UIP fibroblasts: interplay between TGFbeta1, IL-13 and CCL2." Int J Biochem Cell Biol. 40(10):2174-82 (2008).

Mulligan & Berg, "Selection for animal cells that express the *Escherichia coli* gene coding for xanthine-guanine phosphoribosyltransferase," 78(4) Proc Nat'l Acad Sci USA 2072-6 (1981).

Munson & Rodbard, "Ligand: a versatile computerized approach for characterization of ligand-binding systems," 107(1) Anal Biochem 220-39 (1980).

Muzio et al., "Interleukin-13 induces the production of interleukin-1 receptor antagonist (1L-1 ra) and the expression of the mRNA for the intracellular (keratinocyte) form of IL-1 ra in human myelomonocytic cells," Blood 83(7):1738-43 (1994).

Naramura et al., "Mechanisms of cellular cytotoxicity mediated by a recombinant antibody-IL2 fusion protein against human melanoma cells," 39(1) Immunol Lett 91-9 (1994).

Ngoc et al., "Cytokines, allergy, and asthma," Curr Opin Allergy Clin Immunology 5(2):161-66 (2005).

Nisonoff et al., "Separation of univalent fragments from the bivalent rabbit antibody molecule by reduction of disulfide bonds," 89 Arch Biochem Biophys 230-44 (1960).

Ohno et al., "Antigen-binding specificities of antibodies are primarily determined by seven residues of VH", Proc. Natl. Acad. Sci. USA, 82:2945-49 (1985).

O'Hare et al., Transformation of mouse fibroblasts to methotrexate resistance by a recombinant plasmid expressing a prokaryotic dihydrofolate reductase, 78(3) Proc Nat'l Acad Sci USA 1527-31 (1981).

Oi & Morrison, "Chimeric antibodies," Bio Techniques 4:214-221 (1986).

Order, "Analysis, Results, and Future Prospective of the Therapeutic Use of Radiolabeled Antibody in Cancer Therapy," in Monoclonal Antibodies for Cancer Detection and Therapy 303-16 (Baldwin and Byers, eds., 1985).

Padlan, "A possible procedure for reducing the immunogenicity of antibody variable domains while preserving their ligand-binding properties," 28(4-5) Molecular Immunology 489-98 (1991).

Pan Ka et al., "Variable region framework differences result in decreased or increased affinity of variant anti-digoxin antibodies," Immunology 85:3080-84 (1988).

Parham, "On the fragmentation of monoclonal IgG1, IgG2a, and IgG2b from BALB/c mice," 131 (6) J Immunol 2895-2902 (1983).

Paul, W.E., Fundamental Immunology 3rd Ed. Fv Structure and Diversity in Three Dimensions: pp. 292-295 Raven Press, NY 1993.

Pham et al., "De novo proteomic sequencing of a monoclonal antibody raised against OX40 ligand," 352(1) Anal Biochem 77-86 (2006).

Pearson & Lipman "Improved tools for biological sequence comparison," Proc Nat'l Acad Sci USA 85(8):2444-48 (1988).

Pearson et al., "Markers of inflammation and cardiovascular disease: application to clinical and public health practice: A statement for healthcare professionals from the Centers for Disease Control and Prevention and the American Heart Association." Circulation 107(3):499-511 (2003).

Plückthun & Pack, "New protein engineering approaches to multivalent and bispecific antibody fragments," Immunotechnology 3(2):83-105 (1997).

Pollock et al., "Antineutrophil cytoplasmic antibody (ANCA) testing of routine sera varies in different laboratories but concordance is greater for cytoplasmic fluorescence (C-ANCA) and myeloperoxidase specificity (MPO-ANCA)." J Immunol Methods 347(1-2):19-23 (2009).

Presta et al., "Humanization of an antibody directed against IgE," J Immunol 151 (5):2623-32 (1993).

Proudfoot, Transcriptional interference and termination between duplicated alpha-globin gene constructs suggests a novel mechanism for gene regulation, 322(6079) Nature 562-5 (1986).

Punnonen et al., "Interleukin 13 induces interleukin 4-independent IgG4 and IgE synthesis and CD23 expression by human B cells," Proc Nat'l Acad Sci USA 90(8):3730-4 (1993).

Queen et al., "A humanized antibody that binds to the interleukin 2 receptor." Proc Natl Acad Sci U.SA 86 (24):10029-33 (1989).

Rader et al., "A phage display approach for rapid antibody humanization: designed combinatorial V gene libraries," 95(15) Proc Nat'l Acad Sci USA 8910-5 (1998).

Ridker et al., "C-reactive protein, the metabolic syndrome, and risk of incident cardiovascular events: an 8-year follow-up of 14 719 initially healthy American women." Circulation 107(3):391-97 (2003).

Ridker et al, "C-reactive protein and other markers of inflammation in the prediction of cardiovascular disease in women." N Engl J Med. 342(12):836-43 (2000).

Riechmann et al., "Reshaping human antibodies for therapy," 332(6162) Nature 323-7 (1988).

Rizzo et al., "Validation of a model for the complex of HIV-1 reverse transcriptase with Sustiva through computation of resistance profiles," 122(51) J Am Chem Soc 12898-12900 (2000).

Roberts et al., "An integrated strategy for structural characterization of the protein and carbohydrate components of monoclonal antibodies: application to anti-respiratory syncytial virus MAb," 67(20) Anal Chem 3613-25 (1995).

Rodriguez et al., "Lysyl oxidase as a potential therapeutic target." Drug News Perspect. 21:218-24 (2008).

Roguska et al., "Humanization of murine monoclonal antibodies through variable domain resurfacing," 91 (3) Proc Nat'l Acad Sci USA 969-73 (1994).

Rosenberg et al., "Vectors for selective expression of cloned DNAs by T7 RNA polymerase," 56(1) Gene 125-35 (1987).

(56) References Cited

OTHER PUBLICATIONS

Roy et al., "Beneficial effect of anti-interleukin-4 antibody when administered in a murine model of tuberculosis infection." Tuberculosis, 88(3):197-202 (2008).
Rudikoff et al., "Single amino acid substitution altering antigen-binding specificity" Proc. Natl. Acad. Sci. 79 (6):1979-83 (1982).
Sanger et al., "DNA sequencing with chain-terminating inhibitors," 74(12) Proc Nat' l Acad Sci USA 5463-7 (1977).
Santerre et al., "Expression of prokaryotic genes for hygromycin Band G418 resistance as dominant-selection markers in mouse L cells," 30(1-3) Gene 147-56 (1984).
Saudek et al., "A preliminary trial of the programmable implantable medication system for insulin delivery," 321 (9) N Engl J Med 574-9 (1989).
Sefton, "Implantable pumps," 14(3) Grit Rev Biomed Eng 201-40 (1987).
Schoepfer, "The pRSET family of T7 promoter expression vectors for *Escherichia coli*," 124(1) Gene 83-5 (1993).
Scott & Smith, "Searching for peptide ligands with an epitope library," 249(4967) Science 386-90 (1990).
Shen et al., "Single Variable Domain: IgG Fusion: A Novel Recombinant Approach to Fc Domain-Containing BiSpecific Antibodies." J Biol Chem. 281(16): 10706-14 (2006).
Shopes, "A genetically engineered human IgG mutant with enhanced cytolytic activity," 148(9) J Immunol 2918-22 (1992).
Short et al., "Complementary combining site contact residue mutations of the anti-digoxin Fab 26-10 permit high affinity wild-type binding," 277(19) J Biol Chem 16365-70 (2002).
Skerra & Pluckthun, "Assembly of a functional immunoglobulin Fv fragment in *Escherichia coli*," 240(4855) Science 1038-41 (1988).
Smith, "Filamentous fusion phage: novel expression vectors that display cloned antigens on the virion surface," 228 (4705) Science 1315-7 (1985).
Spring & Nisonoff et al., "Allotypic markers on Fab fragments of mouse immunoglobulins," 113(2) J Immunol 470-8 (1974).
Stevenson et al., "A chimeric antibody with dual Fc regions (bisFabFc) prepared by manipulations at the IgG hinge," 3(4) Anticancer Drug Des 219-30 (1989).
Sims et al., "A humanized CD18 antibody can block function without cell destruction," J Immunol 151 (4):2296-308 (1993).
Sozzani et al., "Interleukin-13 inhibits protein kinase C-triggered respiratory burst in human monocytes. Role of calcium and cyclic AMP," J Biol Chem 270(10):5084-8 (1995).
Staerz et al., "Hybrid antibodies can target sites for attack by T cells," Nature 314(6012):628-31 (1985).
Sunderkotter & Sindrilaru, "Clinical classification of vasculitis." Eur J. Dermatol. 16(2):114-24 (2006).
Studnicka et al., "Human-engineered monoclonal antibodies retain full specific binding activity by preserving non-CDR complementarity-modulating residues," 7(6) Protein Engineering 805-14 (1994).
Studier, "Use of bacteriophage T7 lysozyme to improve an inducible T7 expression system," 219(1) J Mol Biol 37-44 (1991).
Sundberg & Mariuzza, "Luxury accommodations: the expanding role of structural plasticity in protein-protein interactions," 8(7) Structure R137-R142 (2000).
Suresh et al., "Bispecific monoclonal antibodies from hybrid hybridomas," 121 Meth Enzym 210-28 (1986).
Szybalska & Szybalski, "Genetics of human cell lines IV_ DNA-mediated heritable transformation of a biochemical trait," 48(12) Proc Nat' l Acad Sci USA 2026-34 (1962).
Takahashi et al., "Human Fas ligand: gene structure, chromosomal location and species specificity," 6(10) Int Immunol 1567-74 (1994).
Tanaka et al., "Interleukin-6, in Cytokine Regulation of Humoral Immunity: Basic and Clinical Aspects," Chapter10:251-272 (Snapper, ed. 1996).
Tesfamariam & DeFelice, "Endothelial injury in the initiation and progression of vascular disorders." Vascul Pharmacol 46(4):229-37 (2007).
Thompson et al., "Affinity maturation of a high-affinity human monoclonal antibody against the third hypervariable loop of human immunodeficiency virus: use of phage display to improve affinity and broaden strain reactivity," 256(1) J Mol Biol 77-88 (1996).
Thornton et al., "Protein structure_ Prediction of progress at last," 354 (6349) Nature 105-6 (1991).
Thotakura & Bahl, "Enzymatic deglycosylation of glycoproteins," 138 Meth Enzymol 350-9 (1987).
Thorpe & Ross, "The preparation and cytotoxic properties of antibody-toxin conjugates," 62 Immunol Rev 119-58 (1982).
Thorpe, "Antibody Carriers of Cytotoxic Agents in Cancer Therapy: A Review," in Monoclonal Antibodies '84: Biological and Clinical Applications, 475-506 (Pinchera et al. eds., 1985).
Todorovska et al., "Design and application of diabodies, triabodies and tetrabodies for cancer targeting," J Immunol Methods 248(1-2):47-66 (2001).
Tomkinson et al., "Inhaled vs subcutaneous effects of a dual IL-4/IL-13 antagonist in a monkey model of asthma." Allergy 65(1):69-77 (2010).
Traunecker et al., "Bispecific single chain molecules (Janusins) target cytotoxic lymphocytes on HIV infected cells," 10(12) EMBO J 3655-9 (1991).
Treat et al., "Liposome Encapsulated Doxorubicin Preliminary Reuslts of Phase I and Phase II Trials," in Liposomes in the Therapy of Infectious Disease and Cancer, 353-65 (Lopez-Berestein et al., eds., 1989).
Trkola et al., "In Vivo Efficacy of Human Immunodeficiency Virus Neutralizing Antibodies: Estimates for Protective Titers-" Journal of Virology 82(3):1591-99 (2008).
Unek et al., The levels of soluble CD40 ligand and C-reactive protein in normal weight, overweight and obese people. Clin Med. Res. 8(2):89-95 (2010).
Urlaub & Chasin, "Isolation of Chinese hamster cell mutants deficient in dihydrofolate reductase activity," 77(7) Proc Nat'l Acad Sci USA 4216-20 (1980).
U.S. Appl. No. 14/619,975 to Hiulle et al., filed Feb. 11, 2015.
Valadon et al., "Screening phage display libraries for organ-specific vascular immunotargeting in vivo," Proc. Nat'l Acad_ Sci. 103(2):407-12 (2006).
Vaughan et al., "Human antibodies by design," 16(6) Nature Biotechnology 535-9 (1998).
Verhoeyen et al., "Reshaping human antibodies: grafting an antilysozyme activity," 239(4847) Science 1534-6 (1988).
Verma et al., "Bispecific antibodies and their use in applied research." Vet. World 5(12):775-80 (2012).
Vita et al., "Characterization and comparison of the interleukin 13 receptor with the interleukin 4 receptor on several cell types," J Biol Chem 270(8):3512-17 (1995).
Wang et al., "Antibody Structure, Instability, and Formulation", Journal of Pharmaceutical Sciences, 96(1):1-26 (Jan. 2007).
Ward et al., "Binding activities of a repertoire of single immunoglobulin variable domains secreted from *Escherichia coli*," 341(6242) Nature 544-6 (1989).
Watts et al., "Development and validation of a consensus methodology for the classification of the AN CA-associated vasculitides and polyarteritis nodosa for epidemiological studies-" Ann Rheum Dis. 66(2):222-27 (2007).
Watis and Ravindran "Pulmonary haemorrhage in ANCA-associated vasculitis." Rheumatology 49(7): 1410-12 (2010).
Waterhouse et al., "Combinatorial infection and in vivo recombination: a strategy for making large phage antibody repertoires," 21(9) Nucl Acids Res 2265-6 (1993).
Wells & Lowman, "Rapid evolution of peptide and protein binding properties in vitro," 2 Curr Opin Struct Biol 597-604 (1992).
Wigler et al., Transfer of purified herpes virus thymidine kinase gene to cultured mouse cells 11(1) Cell 223-32 (1977).
Wigler et al., Transformation of mammalian cells with an amplifiable dominant-acting gene, 77(6) Proc Nat' l Acad Sci USA 3567-70 (1980).
Wiik, "Drug-induced vasculitis." Curr Opin Rheumatol 20(1)35-39 (2008).
Williams et al., Translating basic science into patient therapy for AN CA-associated small vessel vasculitis. Clin Sci (Land). 108(2):101-12 (2005).

(56) References Cited

OTHER PUBLICATIONS

Wilson et al., "The structure of an antigenic determinant in a protein," 37(3) Cell 767-78 (1984).
Winter & Milstein, "Man-made antibodies," Nature 349(6307):293-9 (1991).
Worn & Pluckthun, "Stability engineering of antibody single-chain Fv fragments," 305(5) J Mal Biol 989-1010 (2001).
The Written Opinion of the International Searching Authority for International Application No. PCT/US2012/029147 completed on Jun. 29, 2012, pp. 1-6.
Wu et al., "National Academy of Clinical Biochemistry laboratory medicine practice guidelines: use of cardiac troponin and B-type natriuretic peptide or N-terminal proB-type natriuretic peptide for etiologies other than acute coronary syndromes and heart failure." Clin Chem. 53(12):2086-96 (2007).
Wu & Wu, "Delivery systems for gene therapy," 3(1) Biotherapy 87-95 (1991).
Wu et al., "Multimerization of a chimeric anti-CD20 single-chain Fv-Fc fusion protein is mediated through variable domain exchange," 14(12) Protein Eng 1025-33 (2001).
Wu & Wu, "Receptor-mediated in-vitro gene transformation by a soluble DNA carrier system," 262(10) J Biol Chem 4429-32 (1987).
Wu, "Simultaneous Humanization and Affinity Optimization of Monoclonal Antibodies" Methods in Molecular Biology, 207(1):197-212 (2003).
Wynn, "Fibrotic disease and the T(H)1/T(H)2 paradigm." Nat Rev. Immunol. 4(8):583-94 (2004).
Xiang et al., "Modification in Framework Region I Results in a Decreased Affinity of Chimeric Anti-TAG72 Antibody" Molecular Immunology 28(1/2):141-48 (1998).
Yamamoto et al., "Phase I Study of KW-0761. A Defucosylated Anti-CCR4 Antibody in Relapsed Patients (Pts) with Adult T-Cell Leukemia-Lymphoma (ATL) or Peripheral T-Cell Lymphoma (PTCL): Updated Results." Blood (ASH Annual Meeting Abstracts) 112(11):370-71 (2008).
Yamamoto, K. et al. (Mar. 20, 2010, e-published on Feb. 22, 2010). "Phase I Study of KW-0761. A Defucosylated Humanized Anti-CCR4 Antibody in Related Patients with Adult T-Cell Leukemia-Lymphoma and Peripheral T-Cell Lymphoma," *J. Clin Oncol.* 28(9):1591-1598.
Yang et al., "CDR walking mutagenesis for the affinity maturation of a potent human anti-HIV-1 antibody into the picomolar range," 254(3) J Mol Biol 392-403 (1995).
Zuo et al., "An efficient route to the production of an IgG-like bispecific antibody," Protein Engineering 13(5):361-67 (2000).
Zurawski et al., "Receptors for interleukin-13 and interleukin-4 are complex and share a novel component that functions in signal transduction," EMBO J 12(7):2663-70 (1993).
Zurawski et al., "Continuously Proliferating Human Cell Lines Synthesizing Antibody of Predetermined Specificity," in Monoclonal Antibodies Chapter2:19-33 (Kennett et al., eds. 1980).
Zurawski & De Vries, "Interleukin 13, an interleukin 4-like cytokine that acts on monocytes and B cells, but not on T cells," Immunol Today 15(1):19-26 (1994).
Kurzrock, R. et al. (Nov. 2008). "A Phase I Study of CNTO 328, An Anti-Interelukin-6 Monoclonal Antibody in Patients with B-Cell Non-Hodgkin's Lymphoma Multiple Myeloma, or Castleman's Disease," Blood 112(11):Abstract 1009, two pages.
European Search Report dated Jul. 26, 2017, for EP Application No. 17151270.0, filed on Jan. 12, 2017, eleven pages.
Ich. (May 12, 2005). "The Clinical Evaluation of QT/QTC Interval Prolongation and Proarrhythmic Potential for Non-Antiarrhythmic Drugs," International Conference on Harmonisation of Technical Requirements for Registration of Pharmaceuticals for Human Use, 18 pages.
Nanzando Medical Dictionary. (Jan. 16, 1998). "Acute Phase Protein—C Rectification Quality Trails (C-Reactive Protein Test)," Nanzando Medical Dictionary, 18$^{th}$ edition, Nanzando Co., Ltd., Japan, pp. 453, and 892, (with English translation), 11 pages.
Akers, M.J. et al. (2002) "Formulation Development of Protein Dosage Forms" Chapter 2 in Development and Manufacture of Protein Pharmaceuticals (Pharmaceutical Biotechnology), Kluver Academic/Plenum Pub., New York, pp. 47-127.
Creative Biolabs, (2007-2017); bispecific Antibody (Tand-L033), 2 pages.
International Preliminary Report on Patentability dated Nov. 3, 2015, for PCT Application No. PCT/EP2014/058733, dated Apr. 29, 2014, 9 pages.
International Search Report dated Aug. 6, 2014, for PCT Application No. PCT/ EP2014/058733, filed on Apr. 29, 2014, 8 pages.
Jones, A. (1993). "Analysis of Polypeptides and Proteins," Adv. Drug Delivery Rev. 10:29-90.
Kabat, E. A. et al. (1971). "Attempts to Locate Complementary-determining Residues in the Variable Positions of Light and Heavy Chains," Ann. NY Acad. Sci. 190:382-393.
Kabat, E. A. et al. (1976). "Attempts to Locate Residues in Complementarity Determining Regions of Antibody Combining Sites that Make Contact with Antigen," Proc. Nat Acad. Sci. USA 73(2):617-619.
Kabat, E. A. et al. (1991). "Sequences of Proteins of Immunological Interest," Fifth Edition, U.S. Department of Health and Human Services, NIH Publication No. 91/3242, 84 pages.
Karlin, S. et al. (1993). "Applications and statistics for multiple high-scoring segments in molecular sequences," Proc. Natl.Acad. Sci. USA 90:5873-5877.
Karlin, S. et al. (Mar. 1990). "Methods for Assessing the Statistical Significance of Molecular Sequence Features by Using General Scoring Schemes," Proc. Nall. Acad. Sci. U.S.A. 87:2264-2268.
Kasaian, M.T. et al. (Jul. 2013). "An IL-4/IL-13 Dual Antagonist Reduces Lung Inflammation, Airway Hyperresponsiveness, and IgE Production in Mice," American Journal of Respiratory Cell And Molecular Biology, Jul. 2013; vol. 49; pp. 37-46.
Myers, E. W. et al. (Mar 1988). "Optimal Alignments in Linear Space," Comput Appl Biosci. 4(1):11-17.
Paul, W.E. ed. (1989). Fundamental Immunology: Second Edition, Raven Press, New York, pp.
Pearlman, R. et al. (1991). "6: Analysis of Protein Drugs," in Peptide and Protein Drug Delivery, Vincent H. L Lee Ed., Marcel Dekker, Inc., New York, N. Y., Pubs. pp. 247-301.
Spiess, C. et al. (Sep. 13, 2013). "Development of a Human IgG3 Bispecific Antibody for Dual Targeting of Interleukin-4 (IL-4) and Interleukin-13 (1L-13) Cytokines," The Journal of Biological Chemistry 288(37):26583-26593.
Taylor, L. D. et al. (1992). "A Transgenic Mouse that Expresses a Diversity of Human Sequence Heavy and Light Chain Immunoglobulins," Nucl. Acids Res. 20(23):6287-6295.
Wang, W. et al (1999). "Instability, Stabilization, and Formulation of Liquid Protein Pharmaceutical," Int J Pharmaceuticals 185:129-188.
Written Opinion of the International Searching Authority dated Aug. 6, 2014, for PCT Application No. PCT/EP2014/058733, dated Apr. 29, 2014, 8 pages.
Daugherty, A.L et al. (2010). "Formulation and Delivery Issues for Monoclonal Antibody Therapeutics," Chapter 8 in Current Trends in Monoclonal Antibody Development and Manufacturing, Biotechnology: Pharmaceutical Aspects, S.J. Shrine (ed.) et al., Springer, pp. 103-129.

\* cited by examiner

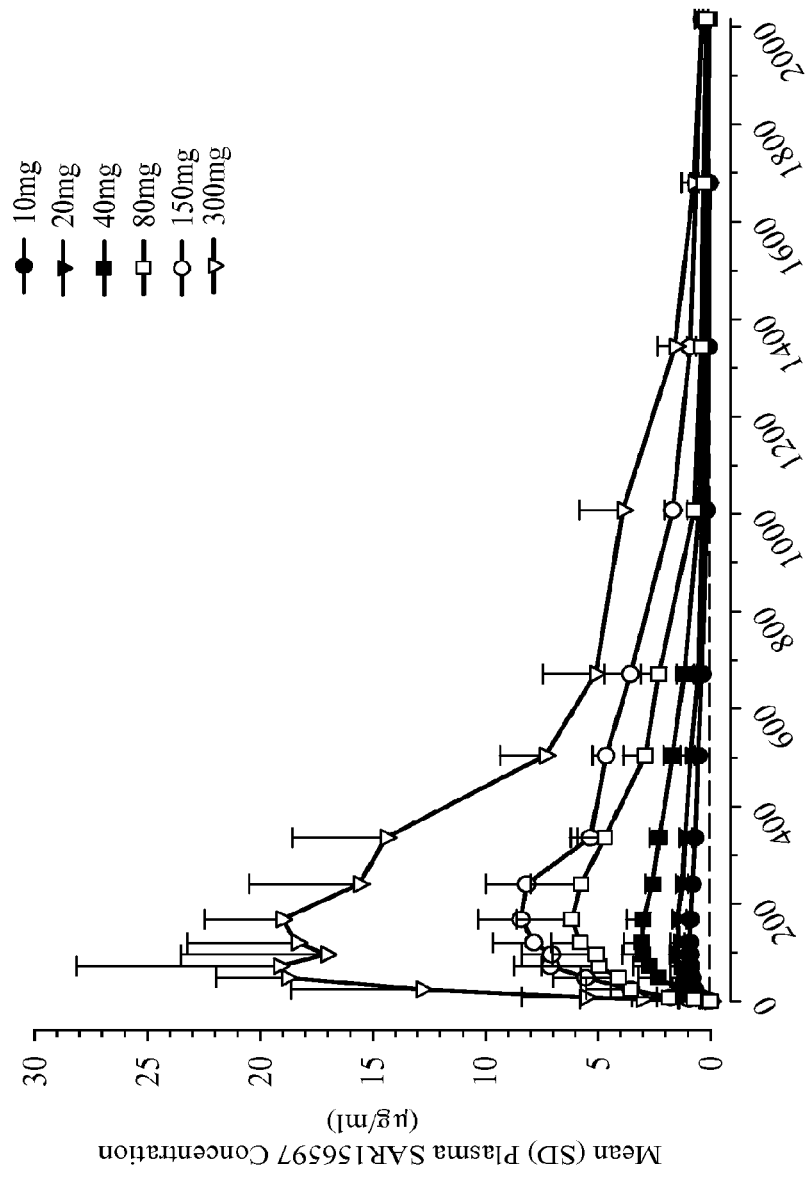

SEQUENCE LISTING

<160> NUMBER OF SEQ ID NOS: 22

<210> SEQ ID NO 1
<211> LENGTH: 111
<212> TYPE: PRT
<213> ORGANISM: Artificial Sequence
<220> FEATURE:
<223> OTHER INFORMATION: humanized mouse/ mouse VL3 region

<400> SEQUENCE: 1

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys
            100                 105                 110
```

<210> SEQ ID NO 2
<211> LENGTH: 118
<212> TYPE: PRT
<213> ORGANISM: Artificial Sequence
<220> FEATURE:
<223> OTHER INFORMATION: humanized mouse/mouse VH2 region

<400> SEQUENCE: 2

```
Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45
```

```
Gly Met Ile Trp Gly Asp Gly Arg Ile Asp Tyr Ala Asp Ala Leu Lys
        50                  55                  60

Ser Arg Leu Ser Ile Ser Lys Asp Ser Ser Lys Ser Gln Val Phe Leu
 65                  70                  75                  80

Glu Met Thr Ser Leu Arg Thr Asp Asp Thr Ala Thr Tyr Tyr Cys Ala
                 85                  90                  95

Arg Asp Gly Tyr Phe Pro Tyr Ala Met Asp Phe Trp Gly Gln Gly Thr
                100                 105                 110

Ser Val Thr Val Ser Ser
            115

<210> SEQ ID NO 3
<211> LENGTH: 108
<212> TYPE: PRT
<213> ORGANISM: Artificial Sequence
<220> FEATURE:
<223> OTHER INFORMATION: humanized mouse/mouse VL1 region

<400> SEQUENCE: 3

Asp Ile Gln Met Thr Gln Ser Pro Ala Ser Leu Ser Val Ser Val Gly
 1               5                  10                  15

Asp Thr Ile Thr Leu Thr Cys His Ala Ser Gln Asn Ile Asp Val Trp
                 20                  25                  30

Leu Ser Trp Phe Gln Gln Lys Pro Gly Asn Ile Pro Lys Leu Leu Ile
             35                  40                  45

Tyr Lys Ala Ser Asn Leu His Thr Gly Val Pro Ser Arg Phe Ser Gly
     50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Ala His Ser Tyr Pro Phe
                 85                  90                  95

Thr Phe Gly Gly Gly Thr Lys Leu Glu Ile Lys Arg
                100                 105

<210> SEQ ID NO 4
<211> LENGTH: 124
<212> TYPE: PRT
<213> ORGANISM: Artificial Sequence
<220> FEATURE:
<223> OTHER INFORMATION: humanized mouse/mouse VH1 region

<400> SEQUENCE: 4

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Ser Tyr
                 20                  25                  30

Trp Ile His Trp Ile Lys Gln Arg Pro Gly Gln Gly Leu Glu Trp Ile
             35                  40                  45

Gly Met Ile Asp Pro Ser Asp Gly Glu Thr Arg Leu Asn Gln Arg Phe
     50                  55                  60

Gln Gly Arg Ala Thr Leu Thr Val Asp Glu Ser Thr Ser Thr Ala Tyr
 65                  70                  75                  80

Met Gln Leu Arg Ser Pro Thr Ser Glu Asp Ser Ala Val Tyr Tyr Cys
                 85                  90                  95

Thr Arg Leu Lys Glu Tyr Gly Asn Tyr Asp Ser Phe Tyr Phe Asp Val
                100                 105                 110

Trp Gly Ala Gly Thr Leu Val Thr Val Ser Ser Ala
            115                 120
```

<210> SEQ ID NO 5
<211> LENGTH: 124
<212> TYPE: PRT
<213> ORGANISM: Artificial Sequence
<220> FEATURE:
<223> OTHER INFORMATION: humanized mouse/mouse VH2 region

<400> SEQUENCE: 5

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Ala Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 6
<211> LENGTH: 10
<212> TYPE: PRT
<213> ORGANISM: Artificial Sequence
<220> FEATURE:
<223> OTHER INFORMATION: linker

<400> SEQUENCE: 6

Gly Gly Gly Gly Ser Gly Gly Gly Gly Ser
1               5                   10

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
ggaggcggag ggtccggagg cggaggatcc                                    30

<210> SEQ ID NO 8
<211> LENGTH: 15
<212> TYPE: PRT
<213> ORGANISM: Artificial Sequence
<220> FEATURE:
<223> OTHER INFORMATION: CDR1

<400> SEQUENCE: 8

Arg Ala Ser Glu Ser Val Asp Ser Tyr Gly Gln Ser Tyr Met His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: CDR2

```
<400> SEQUENCE: 9

Leu Ala Ser Asn Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: CDR3

<400> SEQUENCE: 10

Gln Gln Asn Ala Glu Asp Ser Arg Thr
1               5

<210> SEQ ID NO 11
<211> LENGTH: 10
<212> TYPE: PRT
<213> ORGANISM: Artificial Sequence
<220> FEATURE:
<223> OTHER INFORMATION: CDR1

<400> SEQUENCE: 11

Gly Phe Ser Leu Thr Asp Ser Ser Ile Asn
1               5                   10

<210> SEQ ID NO 12
<211> LENGTH: 5
<212> TYPE: PRT
<213> ORGANISM: Artificial Sequence
<220> FEATURE:
<223> OTHER INFORMATION: CDR2

<400> SEQUENCE: 12

Asp Gly Arg Ile Asp
1               5

<210> SEQ ID NO 13
<211> LENGTH: 10
<212> TYPE: PRT
<213> ORGANISM: Artificial Sequence
<220> FEATURE:
<223> OTHER INFORMATION: CDR3

<400> SEQUENCE: 13

Asp Gly Tyr Phe Pro Tyr Ala Met Asp Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: CDR1

<400> SEQUENCE: 14

His Ala Ser Gln Asn Ile Asp Val Trp Leu Ser
1               5                   10

<210> SEQ ID NO 15
<211> LENGTH: 8
<212> TYPE: PRT
<213> ORGANISM: Artificial Sequence
<220> FEATURE:
<223> OTHER INFORMATION: CDR2
```

```
<400> SEQUENCE: 15

Lys Ala Ser Asn Leu His Thr Gly
1               5

<210> SEQ ID NO 16
<211> LENGTH: 9
<212> TYPE: PRT
<213> ORGANISM: Artificial Sequence
<220> FEATURE:
<223> OTHER INFORMATION: CDR3

<400> SEQUENCE: 16

Gln Gln Ala His Ser Tyr Pro Phe Thr
1               5

<210> SEQ ID NO 17
<211> LENGTH: 10
<212> TYPE: PRT
<213> ORGANISM: Artificial Sequence
<220> FEATURE:
<223> OTHER INFORMATION: CDR1

<400> SEQUENCE: 17

Gly Tyr Ser Phe Thr Ser Tyr Trp Ile His
1               5                   10

<210> SEQ ID NO 18
<211> LENGTH: 9
<212> TYPE: PRT
<213> ORGANISM: Artificial Sequence
<220> FEATURE:
<223> OTHER INFORMATION: CDR2

<400> SEQUENCE: 18

Ile Asp Pro Ser Asp Gly Glu Thr Arg
1               5

<210> SEQ ID NO 19
<211> LENGTH: 14
<212> TYPE: PRT
<213> ORGANISM: Artificial Sequence
<220> FEATURE:
<223> OTHER INFORMATION: CDR3

<400> SEQUENCE: 19

Leu Lys Glu Tyr Gly Asn Tyr Asp Ser Phe Tyr Phe Asp Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: CDR1

<400> SEQUENCE: 20

Gly Tyr Ser Phe Thr Ser Tyr Trp Ile His
1               5                   10

<210> SEQ ID NO 21
<211> LENGTH: 9
<212> TYPE: PRT
<213> ORGANISM: Artificial Sequence
<220> FEATURE:
<223> OTHER INFORMATION: CDR2
```

```
<400> SEQUENCE: 21

Ile Asp Ala Ser Asp Gly Glu Thr Arg
1               5

<210> SEQ ID NO 22
<211> LENGTH: 14
<212> TYPE: PRT
<213> ORGANISM: Artificial Sequence
<220> FEATURE:
<223> OTHER INFORMATION: CDR3

<400> SEQUENCE: 22

Leu Lys Glu Tyr Gly Asn Tyr Asp Ser Phe Tyr Phe Asp Val
1               5                   10
```

USES OF A DUAL V REGION ANTIBODY-LIKE PROTEIN

CROSS-REFERENCE TO RELATED APPLICATIONS

This application is a continuation of U.S. patent application Ser. No. 14/003,496, which adopts the international filing date of Mar. 15, 2012 and is a National Phase application under 35 U.S.C. § 371 of International Application No. PCT/US2012/029147, filed Mar. 15, 2012, which claims the priority benefit of US Provisional Application Nos. 61/557,635, filed Nov. 9, 2011, 61/537,243, filed Sep. 21, 2011, and 61/453,275, filed Mar. 16, 2011, and claims priority benefit of FR Application No. 1162177, filed Dec. 21, 2011, the disclosures of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952026101SeqList.txt, date recorded: Jul. 8, 2016, size: 10 KB).

BACKGROUND OF THE INVENTION

Interleukin-4 (IL-4) is a pleiotropic cytokine that has a broad spectrum of biological effects on lymphoid B and T cells, and many non-lymphoid cells including monocytes, endothelial cells and fibroblasts. For example, IL-4 stimulates the proliferation of several IL-2- and IL-3-dependent cell lines, induces the expression of class II major histocompatability complex molecules on resting B cells, and enhances the secretion of IgG4 and IgE by human B cells. IL-4 is associated with a Th2-type immune response, and is produced by and promotes differentiation of Th2 cells. IL-4 has been implicated in a number of disorders, such as allergy and asthma.

IL-13 is a recently identified (Minty, A. et al., Nature, 1993, 362, 248-250, and McKenzie, A. N. et al., Proc. Natl. Acad. Sci. U.S.A, 1993, 90, 3735-3739) cytokine of 112 amino acids secreted by the activated T lymphocytes, the B lymphocytes and the mastocytes after activation. By virtue of its numerous biological properties shared with IL-4, IL-13 has been described as an IL-4-like cytokine. Its activities are indeed similar to those of IL-4 on the B cells (Defrance, T. et al., J. Exp. Med., 1994, 179, 135-143, Punnonen, J. et al., Proc. Natl. Acad. Sci. (USA), 1993, 90, 3730-3734, Fior, R. et al., Eur. Cytokine Network, 1994, 5, 593-600), the monocytes (Muzio, M. R. F. et al., Blood, 1994, 83, 1738-1743, De Waal Malefyt, R. et al., J. Immunol, 1993, 151, 6370-6381, Doyle, A. et al., Eur. J. Immunol. 1994, 24, 1441-1445, Montaner, L. J. et al., J. Exp. Med., 1993, 178, 743-747, Sozzani, P. et al., J. Biol. Chem., 1995, 270, 5084-5088) and other non-haematopoietic cells (Herbert, J. M. et al., Febs Lett., 1993, 328, 268-270, and Derocq, J. M. et al., Febs Lett. 1994, 343, 32-36). On the other hand, contrary to IL-4, it does not exert a specific effect on resting or activated T cells (Zurawuki, G. et al., Immunol. Today, 1994, 15, 19-26).

Various biological activities of IL-13 on the monocytes/macrophages, the B lymphocytes and certain haematopoietic precursors have been described in detail by A. J. Minty as well as in review articles on IL-13. Several data indicate, in addition, that this cytokine has a pleiotropic effect on other cell types. These non-haematopoietic cells which are directly affected by IL-13 are endothelial and microglial cells, keratinocytes and kidney and colon carcinomas.

One of the stages in the analysis of the signal transmitted by a biological molecule within a cell consists in identifying its membrane receptor. The research studies carried out to this end on the IL-13 receptor have shown that IL-13 and IL-4 have a common receptor, or at the very least some of the components of a common receptor complex, as well as common signal transduction elements (Zurawski S. M. et al., Embo Journal, 1993, 12, 2663-2670, Aversa, G. et al., J. Exp. Med., 1993, 178, 2213-2218, Vita, N. et al., Biol. Chem., 1995, 270, 3512-3517, Lefort, S. et al., Febs Lett., 1995, 366, 122-126). This receptor is present at the surface of various cell types, in a variable number according to the cell type considered. The comparative distribution of the IL-13 and IL-4 receptors has been indicated by A. J. Minty (Interleukin-13 for Cytokines in Health and Disease. Eds D. G. Remick and J. S. Frie, Marcel Decker, N.Y. 1996).

The cell surface receptors and receptor complexes bind IL-4 and/or IL-13 with different affinities. The principle components of receptors and receptor complexes that bind IL-4 and/or IL-13 are IL-4Rα, IL-13Rα1 and IL-13Rα2. These chains are expressed on the surface of cells as monomers or heterodimers of IL-4Rα/IL-13Rα1 (Type II IL-4R) or IL-4Rα/c (Type I IL-4R). IL-4Rα monomer and IL-4R/c heterodimer bind IL-4, but not IL-13. IL-13Rα1 and IL-13Rα2 monomers bind IL-13, but do not bind IL-4. IL-4Rα/IL-13Rα1 heterodimer binds both IL-4 and IL-13 (Murata et al., Int. J. Hematol., 1999, 69, 13-20).

Th2-type immune responses promote antibody production and humoral immunity, and are elaborated to fight off extracellular pathogens. Th2 cells are mediators of Ig production (humoral immunity) and produce IL-4, IL-5, IL-6, IL-9, IL-10 and IL-13 (Tanaka, et, al., Cytokine Regulation of Humoral Immunity, 251-272, Snapper, ed., John Wiley and Sons, New York (1996)). Th2-type immune responses are characterized by the generation of certain cytokines (e.g., IL-4, IL-13) and specific types of antibodies (IgE, IgG4) and are typical of allergic reactions, which may result in watery eyes and asthmatic symptoms, such as airway inflammation and contraction of airway muscle cells in the lungs.

Both IL-4 and IL-13 are therapeutically important cytokines based on their biological functions and play critical roles in many diseases, including asthma (Curr Opin Allergy Clin Immunol 2005, Vo. 5, 161-166). IL-4 has been shown to be able to inhibit autoimmune disease and IL-4 and IL-13 have both shown the potential to enhance anti-tumor immune responses. Elevations in IL-4 and IL-13 and their receptors have been linked to the pathogenesis of idiopathic pulmonary fibrosis (IPF) (Jakubzick C. et al., Am J Pathol. 2004:164(6):1989-2001; Murray L A et al. Int J Biochem Cell Biol. 2008:40(10):2174-82. Evidence in the literature demonstrate that the TH2 cytokines IL-4 and IL-13 play multiple roles in the pathogenesis of IPF as mediators of this lung tissue remodeling and fibrosis. Although the Th2-type CD4+ t cells in the lung are likely the predominant sources of IL-4 and IL-13, and are implicated as important regulators of extracellular matrix remodeling (Wynn, T A, Naat. Rev. Immunol, 4:583-594, 2004), other cell types including mast cells, basophils, eosinophils, macrophages and epithelial cells may also be potential sources of these cytokines (Gordon S and Martinez F O, Immunity Rev. 32:593-604, 2010). In IPF patients, IL-13 and IL-4 levels in bronchial alveolar lavage fluid are elevated compared to normal controls. Such evidence suggests that therapies capable of suppressing or neutralizing these cytokines have the potential for delaying the progression of fibrosis in IPF patients. Since both cytokines are involved in the pathogenesis of allergic diseases or fibrotic diseases, inhibitors of these cytokines could provide therapeutic benefits.

Accordingly, a need exists for improved agents that inhibit IL-4, inhibit IL-13, and single agents that inhibit both IL-4 and IL-13 that are non-immunogenic and safe for use in humans. We previously reported on a dual V region antibody like binding peptide having four binding sites that specifically bind to IL-4 and IL-13 (WO2009/052081 (PCT/US2008/079787), which is incorporated by reference in its entirety.

SUMMARY OF THE INVENTION

An embodiment of the invention is a maximal safe therapeutic dose of a dual V region antibody-like protein or a fragment of a dual V region antibody-like region that specifically binds to IL-4 and IL-13 to a human subject having an area under the plasma concentration versus time curve calculated using the trapezoidal method from time zero to real time ($AUC_{last}$) from about 433 ug·h/ml to about 14200 ug·h/ml. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a maximal safe therapeutic dose of a dual V region antibody-like protein or a fragment of a dual V region antibody-like region that specifically binds to IL-4 and IL-13 to a human subject having an area under the plasma concentration versus time curve extrapolated to infinity (AUC) from about 459 ug·h/ml to about 670014500 ug·h/ml. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a maximal safe therapeutic dose of a dual V region antibody-like protein or a fragment of a dual V region antibody-like region that specifically binds to IL-4 and IL-13 to a human subject having a maximum plasma concentration observed ($C_{max}$) from about 0.717 ug/ml to about 28.7 ug/ml. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a maximal safe therapeutic dose of a dual V region antibody-like protein or a fragment of a dual V region antibody-like region that specifically binds to IL-4 and IL-13 to a human subject having a first time to reach a maximum plasma concentration ($t_{max}$) from about 96 hr to about 168 hr. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a maximal safe therapeutic dose of a dual V region antibody-like protein or a fragment of a dual V region antibody-like region that specifically binds to IL-4 and IL-13 to a human subject having $t_{last}$ from about 1679 hr to about 2020 hr. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a maximal safe therapeutic dose of a dual V region antibody-like protein or a fragment of a dual V region antibody-like region that specifically binds to IL-4 and IL-13 to a human subject having $t_{1/2Z}$ from about 244 hr to about 536 hr. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a maximal safe therapeutic dose of a dual V region antibody-like protein or a fragment of a dual V region antibody-like region that specifically binds to IL-4 and IL-13 to a human subject having Vss/F from about 6830 ml to about 18770 ml. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a maximal safe therapeutic dose of a dual V region antibody-like protein or a fragment of a dual V region antibody-like region that specifically binds to IL-4 and IL-13 to a human subject having CL/F from about 12.1 ml/hr to about 38.4 ml/hr. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a method of identifying or monitoring the occurrence of a safe therapeutic dose of a dual V region antibody-like protein or a fragment of a dual V region antibody-like region that specifically binds to IL-4 and IL-13 having been administered to a human subject, said method comprising (a) administering a dose of said dual V region antibody-like protein or a fragment of a dual V region antibody-like region to said human subject; (b) measuring one or more events selected from the group consisting of intensive treatment in an emergency room or at home for allergic bronchospasm, blood dyscrasias, convulsions, alanine aminotransferase (ALT)>3× upper limit of normal range (ULN) associated with total bilirubin>2×ULN, asymptomatic ALT increase>10×ULN, development of drug dependency or drug abuse, ALT increase≥2×ULN, hsCRP>10 mg/L for ≥72 hours, cardiac troponin I (cTnI)>2×ULN, a ventricular depolarization and repolarization time (QT) on an electrocardiogram (ECG) machine wherein the QT is automatically corrected by the ECG machine (QTc) that is QTc≥500 ms and severe skin reactions local to the site of IP injection; and (c) determining one or more said events as measured in (b) has not occurred wherein said dose is identified as said safe therapeutic dose having been administered to said human subject. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a method monitoring whether a therapeutic dose of a dual V region antibody-like protein or a fragment of a dual V region antibody-like region that specifically binds to IL-4 and IL-13 administered to a human subject is safe, said method comprising (a) administering said therapeutic dose of said dual V region antibody-like protein or a fragment of a dual V region antibody-like region to said human subject; (b) measuring one or more events selected from the group consisting of intensive treatment in an emergency room or at home for allergic bronchospasm, blood dyscrasias, convulsions, alanine aminotransferase (ALT)>3× upper limit of normal range (ULN) associated with total bilirubin>2×ULN, asymptomatic ALT increase>10×ULN, development of drug dependency or drug abuse, ALT increase≥2×ULN, hsCRP>10 mg/L for ≥72 hours, cardiac troponin I (cTnI)>2×ULN, a ventricular depolarization and repolariztion time (QT) on an electrocardiogram (ECG) machine wherein the QT is automatically corrected by the ECG machine (QTc) that is QTc≥500 ms and severe skin reactions local to the site of IP injection; and (c) determining one or more said events as measured in (b) has occurred wherein said therapeutic dose is identified as not safe and the therapeutic dose is discontinued or lowered. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutic dose is equal to or less than about 300 mg. In a further embodiment, the therapeutic dose is selected from the group consisting of 10 mg, 20 mg, 40 mg, 80 mg, 150 mg and 300 mg.

An embodiment of the invention is a method of selecting a safe therapeutic dose or of monitoring the safe use of a therapeutic dose of dual V region antibody-like protein or a fragment of a dual V region antibody-like region that specifically binds to IL-4 and IL-13 to a human subject, said method comprising (a) administering a dose of said dual V region antibody-like protein or a fragment of a dual V region antibody-like region to said human subject; (b) measuring a level of C-reactive protein (CRP) in a blood sample from said human subject; and (c) determining said level of C-reactive protein (CRP) is less than 20 mg/L as measured in (b) wherein said dose is selected as said safe therapeutic dose to be administered to said human subject. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a method of selecting a safe therapeutic dose or of monitoring the safe use of a therapeutic dose of a dual V region antibody-like protein or a fragment of a dual V region antibody-like region that specifically binds to IL-4 and IL-13 to a human subject, said method comprising (a) administering a dose of said dual V region antibody-like protein or a fragment of a dual V region antibody-like region to said human subject; (b) measuring a ventricular depolarization and repolariztion time (QT) on an electrocardiogram (ECG) machine wherein the QT is automatically corrected by the ECG machine (QTc) of said human subject; and (c) determining said QTC is less than 500 ms as measured in (b) wherein said dose is selected as said safe therapeutic dose to be administered to said human subject. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the safe therapeutic dose is equal to or less than about 300 mg. In a further embodiment, the safe therapeutic dose is selected from the group consisting of 10 mg, 20 mg, 40 mg, 80 mg, 150 mg and 300 mg.

An embodiment of the invention is a method of determining whether a therapeutic dose of a dual V region antibody-like protein or a fragment of a dual V region antibody-like region is safe and tolerable for administration to humans, the method comprising (a) perform a non-immunogenicity study in a non-human primate; and (b) determine a safe therapeutic dose in a human patient based on the non-immunogenicity study in the non-human primate. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutic dose is equal to or less than about 300 mg. In a further embodiment, the therapeutic dose is selected from the group consisting of 10 mg, 20 mg, 40 mg, 80 mg, 150 mg and 300 mg.

An embodiment of the invention is a method of measuring total amount of human antibody in a test sample, the method comprising (a) providing a monoclonal anti-human kappa chain; (b) adding a test sample to the monoclonal anti-human kappa chain; (c) adding sulfo-tag labeled anti-human antibody to the monoclonal anti-human kappa chain and the sample; and (d) quantifying the amount of the tag-labeled anti-human antibody that is bound to the sample wherein the amount of the tag-labeled anti-human antibody bound to the test sample determines the total amount of human antibody in the test sample. In further embodiment of the invention, the anti-human kappa chain is attached to a capture device.

An embodiment of the invention is a method of measuring a proportion of bispecific antibody capable of binding IL-4 and IL13 present in a test sample, the method comprising (a) providing a anti-human IL-4 antibody; (b) adding human IL-4 to the anti-human IL-4 antibody; (c) adding a test sample comprising a bispecific antibody capable of binding IL-4 and IL-13 to the human IL-4 and the anti-human IL-4 antibody; (d) adding human IL-13 to the test sample comprising a bispecific antibody capable of binding IL-4 and IL-13 and the human IL-4 and the anti-human IL-4 antibody; (e) adding biotinylated anti-human IL-13 antibody to the test sample comprising a bispecific antibody capable of binding IL-4 and IL-13 and the human IL-4 and the anti-human IL-4 antibody; and (f) adding tag-labeled streptavidin to the biotinylated anti-human IL-13 antibody and the test sample comprising a bispecific antibody capable of binding IL-4 and IL-13 and the human IL-4 and the anti-human IL-4 antibody; and (g) quantifying the amount of the tag-labeled streptavidin that is bound to the biotinylated anti-human IL-13 antibody wherein the amount of the tag-labeled streptavidin bound determines the proportion of bispecific antibody capable of binding IL-4 and IL13 present in the test sample. In a further embodiment of the invention, the anti-human IL-4 antibody is attached to a capture device. In a further embodiment of the invention, the bispecific antibody comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6.

An embodiment of the invention is a method of measuring a proportion of bispecific antibody capable of binding IL-4 and IL13 present in a test sample, the method comprising: (a) providing a anti-human IL-13 antibody; (b) adding human IL-13 to the anti-human IL-13 antibody; (c) adding a test sample comprising a bispecific antibody capable of binding IL-4 and IL-13 to the human IL-13 and the anti-human IL-13 antibody; (d) adding human IL-4 to the test sample comprising a bispecific antibody capable of binding IL-4 and IL-13 and the human IL-13 and the anti-human IL-13 antibody; (e) adding biotinylated anti-human IL-4 antibody to the test sample comprising a bispecific antibody capable of binding IL-4 and IL-13 and the human IL-13 and the anti-human IL-13 antibody; and (f) adding tag-labeled streptavidin to the biotinylated anti-human IL-4 antibody and the test sample comprising a bispecific antibody capable of binding IL-4 and IL-13 and the human IL-13 and the anti-human IL-13 antibody; and (g) quantifying the amount of the tag-labeled streptavidin that is bound to biotinylated anti-human IL-4 antibody wherein the amount of the tag-labeled streptavidin bound determines the proportion of bispecific antibody capable of binding IL-4 and IL13 present in the test sample. In a further embodiment of the invention, the anti-human IL-13 antibody is attached to a capture device. In a further embodiment of the invention, the bispecific antibody comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6.

An embodiment of the invention is a method of measuring anti-drug antibodies in a test sample, the method comprising (a) combining a test sample with a biotinylated bispecific antibody capable of binding IL-4 and IL-13 and a tag-labeled bispecific antibody capable of binding IL-4 and IL-13; (b) adding streptavidin to the test sample and the biotinylated bispecific antibody capable of binding IL-4 and IL-13 and the tag-labeled bispecific antibody capable of binding IL-4 and IL-13; and (c) quantifying the amount of the tag-labeled bispecific antibody capable of binding IL-4 and IL-13 is bound wherein the amount of the tag-labeled bispecific antibody capable of binding IL-4 and IL-13 bound determines the amount of anti-drug antibodies human antibody in the test sample. In a further embodiment of the invention, the streptavidin is attached to a capture device.

An embodiment of the invention is a method of quantifying or monitoring an amount of anti-drug antibodies in blood serum of a human subject or a non-human primate following administration of drug wherein the drug is a dual V region antibody-like protein or a fragment of a dual V region antibody-like region that specifically binds to IL-4 and IL-13, said method comprising: (a) administering a dose of said dual V region antibody-like protein or a fragment of a dual V region antibody-like region to said human subject or said non-human primate; (b) obtaining a sample of said blood serum from said human subject or said non-human primate; and (b) determining the amount of anti-drug antibodies in said serum sample. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6.

An embodiment of the invention is a method of quantifying or monitoring a total amount of a dual V region antibody-like protein or a fragment of a dual V region antibody-like region that specifically binds to IL-4 and IL-13 in blood serum of a human subject or a non-human primate, said method comprising (a) administering a dose of said dual V region antibody-like protein or a fragment of a dual V region antibody-like region to said human subject or said non-human primate; (b) obtaining a sample of said blood serum from said human subject or said non-human primate; and (c) determining said total amount of said dual V region antibody-like protein or a fragment of a dual V region antibody-like region in said sample. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6.

An embodiment of the invention is a method of quantifying or monitoring a proportion of a dual V region antibody-like protein or a fragment of a dual V region antibody-like region that specifically binds to IL-4 and IL-13 that is functionally available to bind IL-4 and IL-13 in blood serum of a human subject or a non-human primate, said method comprising (a) administering a dose of said dual V region antibody-like protein or a fragment of a dual V region antibody-like region to said human subject or said non-human primate; (b) obtaining a sample of said blood serum from said human subject or said non-human primate; and (c) determining said proportion of said dual V region antibody-like protein or a fragment of a dual V region antibody-like region that is functionally available to bind IL-4 and IL-13 in said sample. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6.

An embodiment of the invention is a method of treating asthma in a mammal comprising the step of administering to said mammal a therapeutically effective amount of a dual V region antibody-like protein or a fragment of a dual V region antibody-like region that specifically binds to IL-4 and IL-13. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutically effective amount is equal to or less than about 300 mg. In a further embodiment, the therapeutically effective amount is selected from the group consisting of 10 mg, 20 mg, 40 mg, 80 mg, 150 mg and 300 mg.

An embodiment of the invention is a method of treating idiopathic pulmonary fibrosis in a mammal comprising the step of administering to said mammal a therapeutically effective amount of a dual V region antibody-like protein or a fragment of a dual V region antibody-like region that specifically binds to IL-4 and IL-13. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutically effective amount is equal to or less than about 300 mg. In a further embodiment, the therapeutically effective amount is selected from the group consisting of 10 mg, 20 mg, 40 mg, 80 mg, 150 mg and 300 mg.

An embodiment of the invention is a method of treating a disease mediated by IL-4 or IL-13 or IL-4 and IL-13-induced STAT6 phosphorylation in a mammal which comprises administering a therapeutically effective amount of a dual V region antibody-like protein or a fragment of a dual V region antibody-like region that specifically binds to IL-4 and IL-13. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutically effective amount is equal to or less than about 300 mg. In a further embodiment, the therapeutically effective amount is selected from the group consisting of 10 mg, 20 mg, 40 mg, 80 mg, 150 mg and 300 mg.

An embodiment of the invention is a method of treating a disease mediated by IL-4 or IL-13 or IL-4 and IL-13- induced IL-6 release in a mammal which comprises administering a therapeutically effective amount of a dual V region antibody-like protein or a fragment of a dual V region antibody-like region that specifically binds to IL-4 and IL-13. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutically effective amount is equal to or less than about 300 mg. In a further embodiment, the therapeutically effective amount is selected from the group consisting of 10 mg, 20 mg, 40 mg, 80 mg, 150 mg and 300 mg.

An embodiment of the invention is a method of treating a disease mediated by IL-4 or IL-13 or IL-4 and IL-13- induced eotaxin release in a mammal which comprises administering a therapeutically effective amount of a dual V region antibody-like protein or a fragment of a dual V region antibody-like region that specifically binds to IL-4 and IL-13. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutically effective amount is equal to or less than about 300 mg. In a further embodiment, the therapeutically effective amount is selected from the group consisting of 10 mg, 20 mg, 40 mg, 80 mg, 150 mg and 300 mg.

An embodiment of the invention is a method of treating a disease mediated by IL-4 or IL-13 or IL-4 and IL-13- induced LOX expression in a mammal which comprises administering a therapeutically effective amount of a dual V region antibody-like protein or a fragment of a dual V region antibody-like region that specifically binds to IL-4 and IL-13. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutically effective amount is equal to or less than about 300 mg. In a further embodiment, the therapeutically effective amount is selected from the group consisting of 10 mg, 20 mg, 40 mg, 80 mg, 150 mg and 300 mg.

An embodiment of the invention is a method of treating a disease mediated by IL-4 or IL-13 or IL-4 and IL-13- induced erythrocyte proliferation in a mammal which comprises administering a therapeutically effective amount of a dual V region antibody-like protein or a fragment of a dual V region antibody-like region that specifically binds to IL-4 and IL-13. In a further embodiment of the invention, the dual V region antibody-like protein or the fragment of a dual V region antibody-like region comprises a variable light chain comprising amino acid sequences SEQ ID NO:1 and SEQ ID NO: 3 and a variable heavy chain comprising amino acid sequences SEQ ID NO:2 and SEQ ID NO: 4. In a further embodiment, SEQ ID NO:1 and SEQ ID NO:3 are linked together with a peptide linker and SEQ ID NO:2 and SEQ ID NO:4 are linked together with the peptide linker. In a further embodiment, the peptide linker consists of SEQ ID NO: 6. In another embodiment, the therapeutically effective amount is equal to or less than about 300 mg. In a further embodiment, the therapeutically effective amount is selected from the group consisting of 10 mg, 20 mg, 40 mg, 80 mg, 150 mg and 300 mg.

BRIEF DESCRIPTION OF THE DRAWINGS

FIG. 11 shows the mean of SAR156597 plasma concentrations after a single subcutaneous dose from 10 to 300 mg from TDU11325.

DETAILED DESCRIPTION OF THE INVENTION

Figure 1:
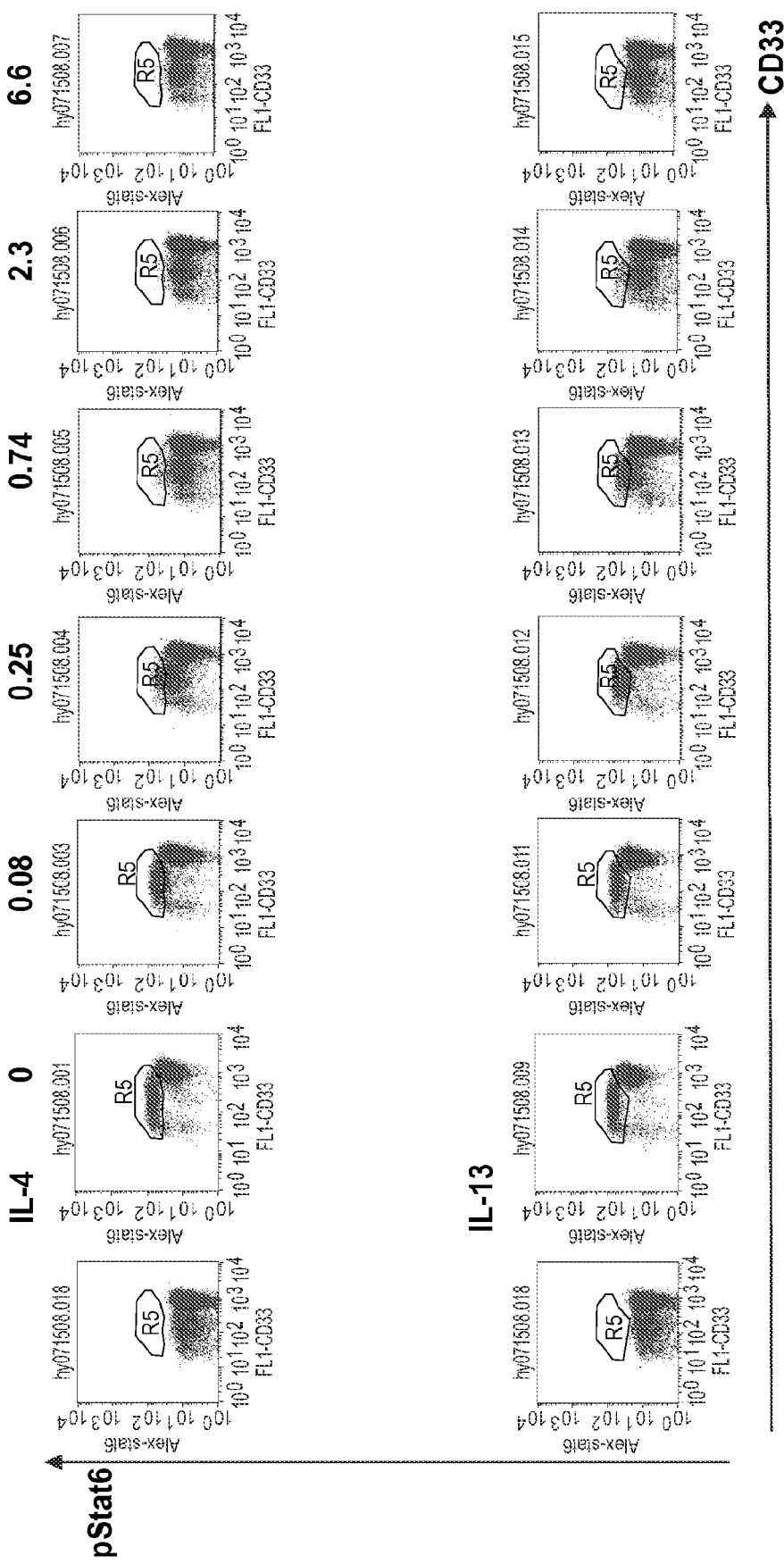
FIG. 1 shows the effects of huTBTI3_2_1 on IL-4- induced or IL-13-induced Stat6 phosphorylation in IL-4- or IL-13-stimulated monocytes.

Unless otherwise defined, all technical and scientific terms used herein have the same meaning as commonly understood by one of ordinary skill in the art to which this invention belongs.

Each publication, patent application, patent, and other reference cited herein is incorporated by reference in its entirety to the extent that it is not inconsistent with this present disclosure.

It is noted here that, as used in this specification and the appended claims, the singular forms "a," "an," and "the" include plural reference unless the context clearly dictates otherwise.

Furthermore, in accordance with the present invention there may be employed conventional molecular biology, microbiology, and recombinant DNA techniques within the skill of the art. Such techniques are explained fully in the literature. See, e.g., Sambrook, Fritsch & *Maniatis, Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Flames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology, John* Wiley & Sons, Inc. (1994).

The following non-limiting definitions of some terms and phrases are provided to guide the artisan.

"Interleukin-4" (IL-4) relates to the naturally occurring, or endogenous mammalian IL-4 proteins and to proteins having an amino acid sequence which is the same as that of a naturally occurring or endogenous corresponding mammalian IL-4 protein {e.g., recombinant proteins, synthetic proteins (i.e., produced using the methods of synthetic organic chemistry)). Accordingly, as defined herein, the term includes mature IL-4 protein, polymorphic or allelic variants, and other isoforms of an IL-4 and modified or unmodified forms of the foregoing (e.g., lipidated, glycosylated). Naturally occurring or endogenous IL-4 includes wild type proteins such as mature IL-4, polymorphic or allelic variants and other isoforms and mutant forms which occur naturally in mammals (e.g., humans, non-human primates). Such proteins can be recovered or isolated from a source which naturally produces IL-4, for example. These proteins and proteins having the same amino acid sequence as a naturally occurring or endogenous corresponding IL-4, are referred to by the name of the corresponding mammal. For example, where the corresponding mammal is a human, the protein is designated as a human IL-4. Several mutant IL-4 proteins are known in the art, such as those disclosed in WO 03/038041.

"Interleukin-13" (IL-13) refers to naturally occurring or endogenous mammalian IL-13 proteins and to proteins having an amino acid sequence which is the same as that of a naturally occurring or endogenous corresponding mammalian IL-13 protein (e.g., recombinant proteins, synthetic proteins (i.e., produced using the methods of synthetic organic chemistry)). Accordingly, as defined herein, the term includes mature IL-13 protein, polymorphic or allelic variants, and other isoforms of IL-13 (e.g., produced by alternative splicing or other cellular processes), and modified or unmodified forms of the foregoing (e.g., Hpidated, glycosylated). Naturally occurring or endogenous IL-13 include wild type proteins such as mature IL-13, polymorphic or allelic variants and other isoforms and mutant forms which occur naturally in mammals (e.g., humans, non-human primates). For example, as used herein IL-13 encompasses the human IL-13 variant in which Arg at position 110 of mature human IL-13 is replaced with Gin (position 110 of mature IL-13 corresponds to position 130 of the precursor protein) which is associated with asthma (atopic and nonatopic asthma) and other variants of IL-13. (Heinzmann el al, Hum Mol Genet. 9:549-559 (2000).) Such proteins can be recovered or isolated from a source which naturally produces IL-13, for example. These proteins and proteins having the same amino acid sequence as a naturally occurring or endogenous corresponding IL-13 are referred to by the name of the corresponding mammal. For example, where the corresponding mammal is a human, the protein is designated as a human IL-13. Several mutant IL-13 proteins are known in the art, such as those disclosed in WO 03/035847.

The phrase "substantially identical" with respect to an antibody chain polypeptide sequence may be construed as an antibody chain exhibiting at least 70%, 80%, 90%, 95%, 96%, 97%, 98%, 99% or more sequence identity to the reference polypeptide sequence. The term with respect to a nucleic acid sequence may be construed as a sequence of nucleotides exhibiting at least about 85%, 90%, 95%, 96%, 97%, 98%, 99% or more sequence identity to the reference nucleic acid sequence. Identity can be determined by using any bioinformatics tool available to one skilled in the art. For example, Basic Local Alignment Search Tool (BLAST) is commonly employed to determine sequence identity (Altschul et al., Journal of Molecular Biology 215(3):403-410, 1990).

The terms, "identity" or "homology" may mean the percentage of nucleotide bases or amino acid residues in the candidate sequence that are identical with the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are available and well known in the art. Sequence identity may be measured using sequence analysis software.

The phrases and terms "functional fragment, variant, derivative or analog" and the like, as well as forms thereof, of an antibody or antigen is a compound or molecule having qualitative biological activity in common with a full-length antibody or antigen of interest. For example, a functional fragment or analog of an anti-IL-4 antibody is one which can bind to an IL-4 molecule or one which can prevent or substantially reduce the ability of a ligand, or an agonistic or antagonistic antibody, to bind to IL-4.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "antibody" is used in the broadest sense, and specifically covers monoclonal antibodies (including full length monoclonal antibodies), polyclonal antibodies, multispecific antibodies (e.g., bispecific antibodies), antibody fragments or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules which lack target specificity. The antibodies of the invention can be of any class (e.g., IgG, IgE, IgM, IgD, IgA and so on), or subclass (e.g., $IgG_1$, $IgG_2$, $IgG_{2a}$, $IgG_3$, $IgG_4$, $IgA_1$, $IgA_2$ and so on) ("type" and "class", and "subtype" and "subclass", are used interchangeably herein). Native or wildtype, that is, obtained from a non-artificially manipulated member of a population, antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at the other end. By "non-artificially manipulated" is meant not treated to contain or express a foreign antigen binding molecule. Wildtype can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-IL-4 antibody" means an antibody or polypeptide derived therefrom (a derivative) which binds specifically to IL-4 as defined herein, including, but not limited to, molecules which inhibit or substantially reduce the binding of IL-4 to its receptor or inhibit IL-4 activity.

As used herein, "anti-IL-13 antibody" means an antibody or polypeptide derived therefrom (a derivative) which binds specifically to IL-13 as defined herein, including, but not limited to, molecules which inhibit or substantially reduce the binding of IL-13 to its receptor or inhibit IL-13 activity.

The term "variable" in the context of a variable domain of antibodies refers to certain portions of the pertinent molecule which differ extensively in sequence between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) also known as hypervariable regions, both in the light chain and the heavy chain variable domains. The more highly conserved portions of variable domains are called the framework (FR) regions or sequences. The variable domains of native heavy and light chains each comprise four FR regions, largely adopting a β-sheet configuration, connected by three CDRs, which form loops connecting, and in some cases forming part of, the β-sheet structure. The CDRs in each chain are held together often in proximity by the FR regions and, with the CDRs from the other chain, contribute to the formation of the target (epitope or determinant) binding site of antibodies (see Kabat et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat et al., unless otherwise indicated. One CDR can carry the ability to bind specifically to the cognate epitope.

The term "hinge" or "hinge region" as used in the present invention refers to the flexible polypeptide comprising the amino acids between the first and second constant domains of an antibody.

The term "antibody fragment" refers to a portion of an intact or a full-length chain or an antibody, generally the target binding or variable region. Examples of antibody fragments include, but are not limited to, $F_{ab}$, $F_{ab'}$, $F_{(ab')2}$ and $F_v$ fragments. A "functional fragment" or "analog of an anti-IL-4 and/or IL-13 antibody" is one which can prevent or substantially reduce the ability of the receptor to bind to a ligand or to initiate signaling. As used herein, functional fragment generally is synonymous with, "antibody fragment" and with respect to antibodies, can refer to fragments, such as $F_v$, $F_{ab}$, $F_{(ab')2}$ and so on which can prevent or substantially reduce the ability of the receptor to bind to a ligand or to initiate signaling. An "$F_v$" fragment consists of a dimer of one heavy and one light chain variable domain in a non-covalent association ($V_H$-$V_L$ dimer). In that configuration, the three CDRs of each variable domain interact to define a target binding site on the surface of the $V_H$-$V_L$ dimer, as in an intact antibody. Collectively, the six CDRs confer target binding specificity on the intact antibody. However, even a single variable domain (or half of an $F_v$ comprising only three CDRs specific for a target) can have the ability to recognize and to bind target.

"Single-chain $F_v$," "s$F_v$," or "scAb" antibody fragments comprise the $V_H$ and $V_L$ domains of an antibody, wherein these domains are present in a single polypeptide chain. Generally, the $F_v$ polypeptide further comprises a polypeptide linker, often a flexible molecule, between the $V_H$ and $V_L$ domains, which enables the sFv to form the desired structure for target binding.

The term "diabodies" refers to antibody fragments with two antigen-binding sites, which fragments can comprise a heavy chain variable domain ($V_H$) connected to a light chain variable domain ($V_L$) in the same polypeptide chain. By using a linker that is too short to allow pairing between the two variable domains on the same chain, the diabody domains are forced to pair with the binding domains of another chain to create two antigen-binding sites.

The $F_{ab}$ fragment contains the variable and constant domains of the light chain and the variable and first constant domain ($C_{H1}$) of the heavy chain. $F_{ab'}$ fragments differ from $F_{ab}$ fragments by the addition of a few residues at the carboxyl terminus of the $C_{H1}$ domain to include one or more cysteines from the antibody hinge region. $F_{ab'}$ fragments can be produced by cleavage of the disulfide bond at the hinge cysteines of the $F_{(ab')2}$ pepsin digestion product. Additional enzymatic and chemical treatments of antibodies can yield other functional fragments of interest.

The term "linear Fab" refers to a tetravalent antibody as described by Miller et al. (2003), J Immunol. 170: 4854-4861. The "linear Fab" is composed of a tandem of the same CH1-VH domain, paired with the identical light chain at each CH1-VH position. These molecules have been developed in order to increase the valency of an antibody to enhance its functional affinity through the avidity effect, but they are monospecific.

The term "bispecific antibodies (BsAbs)" refers to molecules which combine the antigen-binding sites of two antibodies within a single molecule. Thus, a bispecific antibody is able to bind two different antigens simultaneously. Besides applications for diagnostic purposes, BsAbs pave the way for new therapeutic applications by redirecting potent effector systems to diseased areas or by increasing neutralizing or stimulating activities of antibodies.

Monoclonal antibodies herein specifically include "chimeric" antibodies in which a portion of the heavy and/or light chain is identical with or homologous to corresponding sequences in antibodies derived from a particular species or belonging to a particular antibody class or subclass (type or subtype), with the remainder of the chain(s) identical with or homologous to corresponding sequences in antibodies derived from another species or belonging to another antibody class or subclass, as well as fragments of such antibodies, so long as they exhibit the desired biological activity of binding to IL-4 and/or IL-13 or impacting IL-4 and/or IL-13 activity or metabolism (U.S. Pat. No. 4,816,567; and Morrison et al., Proc Natl Acad Sci USA 81:6851 (1984)). Thus, CDRs from one class of antibody can be grafted into the FR of an antibody of different class or subclass.

Monoclonal antibodies are highly specific, being directed against a single target site, epitope or determinant. Furthermore, in contrast to conventional (polyclonal) antibody preparations which typically include different antibodies directed against different determinants (epitopes) of an antigen, each monoclonal antibody is directed against a single determinant on the target. In addition to their specificity, monoclonal antibodies are advantageous being synthesized by a host cell, uncontaminated by other immunoglobulins, and provides for cloning the relevant gene and mRNA encoding the antibody of chains thereof. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using well known techniques or can be purified from a polyclonal preparation. The parent monoclonal antibodies to be used in accordance with the present invention may be made by the hybridoma method described by Kohler et al., Nature 256:495 (1975), or may be made by recombinant methods well known in the art.

The term "polyvalent antibody" as used in the present invention refers to an antibody comprising two or more antigen binding sites, thus being able to bind two or more antigens, which may have the same or a different structure, simultaneously. The term "bivalent" means that the antibody comprises two antigen binding sites. The term "tetravalent" means that the antibody comprises four antigen binding sites.

The term "antigen binding site" as used in the present invention refers to the part of the antibody which comprises the area which specifically binds to and is complementary to part or all of an antigen. Where an antigen is large, an antibody may only bind to a particular part of the antigen, which part is termed on epitope. An antigen binding domain may be provided by one or more antibody variable domains. Preferably, an antigen binding domain is made of the association of an antibody light chain variable domain (VL) and an antibody heavy chain variable domain (VH).

The term "antigen" as used in the present invention refers to a molecule or a portion of a molecule capable of being bound by the antibodies of the present invention. An antigen can have one or more than one epitope. Examples of antigens recognized by the antibodies of the present invention include, but are not limited to, serum proteins, e.g. cytokines such as IL-4, IL-5, IL-9 and IL-13, bioactive peptides, cell surface molecules, e.g. receptors, transporters, ion-channels, viral and bacterial proteins.

The term "monospecific" as used in the present invention means that the polyvalent antibody of the present invention recognizes only one antigen, all the antigen binding sites being identical.

The term "bispecific" as used in the present invention means that the polyvalent antibody of the present invention recognizes two different epitopes on the same or on two different antigens.

It has been of interest to produce bispecific antibodies (BsAbs) which combine the antigen-binding sites of two antibodies within a single molecule. Thus, such a molecule would be able to bind two different antigens simultaneously. Besides applications for diagnostic purposes, they pave the way for new therapeutic applications, e.g. by redirecting potent effector systems to diseased areas (where cancerous cells often develop mechanisms to suppress normal immune responses triggered by monoclonal antibodies, like antibody-dependent cellular cytotoxicity (ADCC) or complement-dependent cytotoxicity (CDC)), or by increasing neutralizing or stimulating activities of antibodies. Initial attempts to couple the binding specificities of two whole antibodies against different target antigens for therapeutic purposes utilized chemically fused heteroconjugate molecules (Staerz et al. (1985), Nature 314: 628-631).

Bispecific antibodies were originally made by fusing two hybridomas, each capable of producing a different immunoglobulin (Milstein and Cuello, 1983, 1984), but the complexity of species (up to ten different species) produced in cell culture makes purification difficult and expensive (George and Huston, 1997). Despite the promising results obtained using heteroconjugates or bispecific antibodies produced from cell fusions as cited above, several factors made them impractical for large scale therapeutic applications. Such factors include: rapid clearance of heteroconjugates in vivo, the laboratory intensive techniques required for generating either type of molecule, the need for extensive purification of heteroconjugates away from homoconjugates or mono-specific antibodies and generally low yields.

Genetic engineering has been used with increasing frequency to design, modify, and produce antibodies or antibody derivatives with a desired set of binding properties and effector functions. A variety of recombinant methods have been developed for efficient production of BsAbs, both as antibody fragments (Carter et al. (1995), J. Hematotherapy 4:463-470; Pluckthun et al. (1997) Immunotechology 3: 83-105; Todorovska et al. (2001) J. Immunol. Methods 248: 47-66) and full length IgG formats (Carter (2001) J. Immunol. Methods 248: 7-15).

Abbott described in U.S. Pat. No. 7,612,181 a murine Dual-Variable-Domain IgG (DVD-IgG) bispecific antibody, which is based on the dual-Fv format described in Unilever patent (U.S. Pat. No. 5,989,830). A humanized bispecific format was described in WO2009/052081 (TBTI) which is incorporated herein by reference in its entirety. The addition of constant domains to respective chains of the Dual-Fv (CH1-Fc to the heavy chain and kappa or lambda constant domain to the light chain) led to functional bispecific dual V region antibody like binding proteins.

An embodiment of the invention is a bispecific antibody that has been engineered to comprise a dual V region antibody-like protein or fragment thereof that specifically binds to two different epitopes on the same or on two different antigens. An embodiment of the invention a bispecific antibody or bispecific antibody fragment thereof that specifically binds to IL-13 and IL-4, wherein said bispecific antibody or bispecific antibody fragment thereof comprises a variable light chain domain and a variable heavy chain domain, wherein said variable light chain domain comprises amino acid sequences SEQ ID NO:1 and SEQ ID NO:3. A further embodiment of the invention is a bispecific antibody or bispecific antibody fragment thereof that specifically binds to IL-13 and IL-4, wherein said bispecific antibody or bispecific antibody fragment thereof comprises a variable light chain domain and a variable heavy chain domain, wherein said variable heavy chain domain comprises amino acid sequences SEQ ID NO:2 and SEQ ID NO:5. Another embodiment of the invention is a bispecific antibody or bispecific antibody fragment thereof that specifically binds to IL-13 and IL-4, wherein said bispecific antibody or bispecific antibody fragment thereof comprises a variable light chain domain and a variable heavy chain domain, wherein said variable heavy chain domain comprises amino acid sequences SEQ ID NO:2 and SEQ ID NO:4. An embodiment of the invention is a bispecific antibody or bispecific antibody fragment thereof that specifically binds to IL-13 and IL-4, wherein said bispecific antibody or bispecific antibody fragment thereof comprises a variable light chain domain comprising amino acid sequences SEQ ID NO:1 and SEQ ID NO:3, and a variable heavy chain domain comprising amino acid sequences SEQ ID NO:2 and SEQ ID NO:4. A further embodiment of the invention is a bispecific antibody or bispecific antibody fragment thereof that specifically binds to IL-13 and IL-4, wherein said bispecific antibody or bispecific antibody fragment thereof comprises a variable light chain domain comprising amino acid sequences SEQ ID NO:1 and SEQ ID NO:3, and a variable heavy chain domain comprising amino acid sequences SEQ ID NO:2 and SEQ ID NO:4, wherein a peptide linker links SEQ ID NO:1 to SEQ ID NO:3, and a peptide linker links SEQ ID NO:2 to SEQ ID NO:4. An embodiment of the invention is huTBTI3_2_1 or SAR156597 comprising a bispecific antibody or bispecific antibody fragment thereof that specifically binds to IL-13 and IL-4, comprising (a) variable light chain domain comprising the amino acid sequences of SEQ ID NO:1 and SEQ ID NO:3; (b) a variable heavy chain domain comprising the amino acid sequences of SEQ ID NO:2 and SEQ ID NO:4; (c) a peptide linker linking SEQ ID NO:1 to SEQ ID NO:3, and a peptide linker linking SEQ ID NO:2 to SEQ ID NO:4 wherein the peptide linker has an amino acid sequence consisting of SEQ ID NO:6; and (d) constant region domains.

The term "multispecific" as used in the present invention means that the polyvalent antibody of the present invention recognizes multiple different epitopes on the same or on multiple different antigens.

The term "linker" as used in the present invention refers to a peptide adapted to connect the variable domains of the antibody constructs of the present invention. The peptide linker may contain any amino acids, the amino acids glycine (G) and serine (S) being preferred. The linkers may be equal or differ from each other between and within the heavy chain polypeptide and the light chain polypeptide. Furthermore, the linker may have a length of 1, 2, 3, 4, 5, 6, 7, 8, 9, 10, 11, 12, 13, 14, 15, 16, 17, 18, 19 or 20 amino acids. A preferred peptide linker unit for the heavy chain domains as for the light chain domains is GGGGS. The numbers of linker units of the heavy chain and of the light chain may be equal (symmetrical order) or differ from each other (asymmetrical order).

A peptide linker is preferably long enough to provide an adequate degree of flexibility to prevent the antibody moieties from interfering with each others activity, for example by steric hindrance, to allow for proper protein folding and, if necessary, to allow the antibody molecules to interact with two or more, possibly widely spaced, receptors on the same cell; yet it is preferably short enough to allow the antibody moieties to remain stable in the cell.

Therefore, the length, composition and/or conformation of the peptide linkers can readily be selected by one skilled in the art in order to optimize the desired properties of the polyvalent antibody.

"Humanized" forms of non-human (e.g., murine) antibodies are chimeric immunoglobulins, immunoglobulin chains or fragments thereof (such as $F_v$, $F_{ab}$, $F_{ab'}$, $F_{(ab')2}$ or other target-binding subsequences of antibodies) which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region ($F_c$), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to IL-4 and/or IL-13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., Prot Eng 7(6)805-814, 1994; Mol Imm 44:1986-1988, 2007; Sims et al., J Immunol 151:2296 (1993); Chothia et al., J Mol Biol 196:901 (1987); Carter et al., Proc Natl Acad Sci USA 89:4285 (1992); Presta et al., J Immunol 151:2623 (1993), WO 2006/042333 and U.S. Pat. No. 5,869,619.

"Antibody homolog" or "homolog" refers to any molecule which specifically binds IL-4 and/or IL-13 as taught herein. Thus, an antibody homolog includes native or recombinant antibody, whether modified or not, portions of antibodies that retain the biological properties of interest, such as binding IL-4 or IL-13, such as an $F_{ab}$ or $F_v$ molecule, a single chain antibody, a polypeptide carrying one or more CDR regions and so on. The amino acid sequence of the homolog need not be identical to that of the naturally occurring antibody but can be altered or modified to carry substitute amino acids, inserted amino acids, deleted amino acids, amino acids other than the twenty normally found in proteins and so on to obtain a polypeptide with enhanced or other beneficial properties.

Antibodies with homologous sequences are those antibodies with amino acid sequences that have sequence homology with the amino acid sequence of a IL-4, IL-13 or bispecific IL-4/IL-13 antibody of the present invention. Preferably, homology is with the amino acid sequence of the variable regions of an antibody of the present invention. "Sequence homology" as applied to an amino acid sequence herein is defined as a sequence with at least about 90%, 91%, 92%, 93%, 94%, 95%, 96%, 97%, 98% or 99% sequence homology to another amino acid sequence, as determined, for example, by the FASTA search method in accordance with Pearson & Lipman, Proc Natl Acad Sci USA 85, 2444-2448 (1988).

A chimeric antibody is one with different portions of an antibody derived from different sources, such as different antibodies, different classes of antibody, different animal species, for example, an antibody having a variable region derived from a murine monoclonal antibody paired with a human immunoglobulin constant region and so on. Thus, a humanized antibody is a species of chimeric antibody. Methods for producing chimeric antibodies are known in the art, see, e.g., Morrison, 1985, Science 229:1202; Oi et al., 1986, BioTechniques 4:214; Gillies et al., 1989, J Immunol Methods 125:191-202; and U.S. Pat. Nos. 5,807,715, 4,816,567, and 4,816,397.

Artificial antibodies include scFv fragments, chimeric antibodies, diabodies, triabodies, tetrabodies and mru (see reviews by Winter & Milstein, 1991, Nature 349:293-299; and Hudson, 1999, Curr Opin Imm 11:548-557), each with antigen-binding or epitope-binding ability. In the single chain $F_v$ fragment (scF$_v$), the $V_H$ and $V_L$ domains of an antibody are linked by a flexible peptide. Typically, the linker is a peptide of about 15 amino acids. If the linker is much smaller, for example, 5 amino acids, diabodies are formed. The smallest binding unit of an antibody is a CDR, typically the CDR2 of the heavy chain which has sufficient specific recognition and binding capacity. Such a fragment is called a molecular recognition unit or mru. Several such mrus can be linked together with short linker peptides, therefore forming an artificial binding protein with higher avidity than a single mru.

Also included within the scope of the invention are functional equivalents of an antibody of interest. The term "functional equivalents" includes antibodies with homologous sequences, antibody homologs, chimeric antibodies, artificial antibodies and modified antibodies, for example, wherein each functional equivalent is defined by the ability to bind to IL-4 and/or IL-13, inhibiting IL-4 and/or IL-13 signaling ability or function, or inhibiting binding of IL-4 and/or IL-13 to its receptor. The skilled artisan will understand that there is an overlap in the group of molecules termed "antibody fragments" and the group termed "functional equivalents." Methods of producing functional equivalents which retain IL-4 and/or IL-13 binding ability are known to the person skilled in the art and are disclosed, for example, in WO 93/21319, EPO Ser. No. 239,400, WO 89/09622, EPO Ser. No. 338,745 and EPO Ser. No. 332,424.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, deamidation, phosphorylation, amidation, derivatization by known protecting/blocking groups, proteolytic cleavage, linkage to a cellular ligand, linkage to a toxin or cytotoxic moiety or other protein etc. The covalent attachment need not yield an antibody that is immune from generating an anti-idiotypic response. The modifications may be achieved by known techniques, including, but not limited to, specific chemical cleavage, acetylation, formylation, metabolic synthesis etc. Additionally, the modified antibodies may contain one or more non-classical amino acids.

"Mammal" for purposes of treatment refers to any animal classified as a mammal, including human, domestic and farm animals, nonhuman primates, and zoo, sports or pet animals, such as dogs, horses, cats, cows etc.

The term "treatment", "therapeutic dose" or "administering a therapeutically effective amount" as used in the present invention refers to both therapeutic treatment and prophylactic or preventative measures as a course of therapy. It refers to preventing, curing, reversing, attenuating, alleviating, minimizing, suppressing or halting deleterious effects of a disease state, disease progression, disease causative agent (e.g., bacteria or viruses) or other abnormal condition.

An embodiment of the invention is the treatment of asthma and idiopathic pulmonary fibrosis. IL-4 and IL-13 are therapeutically important cytokines based on their biological functions and play critical roles in many diseases, including asthma (Curr Opin Allergy Clin Immunol 2005, Vo. 5, 161-166). IL-4 has been shown to be able to inhibit autoimmune disease and IL-4 and IL-13 have both shown the potential to enhance anti-tumor immune responses. Elevations in IL-4 and IL-13 and their receptors have been linked to the pathogenesis of idiopathic pulmonary fibrosis (IPF) (Jakubzick C. et al., Am J Pathol. 2004:164(6):1989-2001; Murray L A et al. Int J Biochem Cell Biol. 2008:40(10):2174-82. Evidence in the literature demonstrate that the TH2 cytokines IL-4 and IL-13 play multiple roles in the pathogenesis of IPF as mediators of this lung tissue remodeling and fibrosis (Wynn, T A, Naat. Rev. Immunol, 4:583-

594, 2004) and other cell types including mast cells, basophils, eosinophils, macrophages and epithelial cells may also be potential sources of these cytokines (Gordon S and Martinez F O, Immunity Rev. 32:593-604, 2010). In IPF patients, IL-13 and IL-4 levels in bronchial alveolar lavage fluid are elevated compared to normal controls. Such evidence suggests that therapies capable of suppressing or neutralizing these cytokines have the potential for delaying the progression of fibrosis in IPF patients. Since both cytokines are involved in the pathogenesis of allergic diseases or fibrotic diseases, inhibitors of these cytokines could provide therapeutic benefits.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 30%, 20%, 10%, 5%, 2.5% or 1%, (by dry weight) of contaminating protein. When the antibody is recombinantly produced, it is also preferably substantially free of culture medium, i.e., culture medium represents less than about 20%, 10%, 5%, 2.5% or 1% of the volume of the protein preparation. When antibody is produced by chemical synthesis, it is preferably substantially free of chemical precursors or other chemicals and reagents, i.e., the antibody of interest is separated from chemical precursors or other chemicals which are involved in the synthesis of the protein. Accordingly, such preparations of the antibody have less than about 30%, 20%, 10%, 5% or 1% (by dry weight) of chemical precursors or compounds other than antibody of interest. In a preferred embodiment of the present invention, antibodies are isolated or purified.

As used herein, the terms "therapeutic agent" and "therapeutic agents" refer to any agent(s) which can be used in the treatment, management or amelioration of a disease, disorder, malady and the like associated with aberrant IL-4 and/or IL-13 metabolism and activity.

As used herein, "therapeutic dose" refers to the quantity of any agent(s) which can be used in the treatment, management or amelioration of a disease, disorder, malady and the like associated with aberrant IL-4 and/or IL-13 metabolism and activity.

As used herein, "safe therapeutic dose" refers to any agent(s) or dose of any agent(s) which can be used in the treatment, management or amelioration of a disease, disorder, malady and the like associated with aberrant IL-4 and/or IL-13 metabolism and activity while maintaining a clinically acceptable benefit/risk profile. A safe therapeutic dose is selected form the group consisting of 10 mg, 20 mg, 40 mg, 80 mg, 150 mg and 300 mg. An embodiment of a safe therapeutic dose is about 10 mg to about 300 mg. A further embodiment of a safe therapeutic dose is any dose that is about 300 mg or less than about 300 mg.

An embodiment of the invention is identifying or monitoring a safe therapeutic dose by measuring one or more events selected from the group consisting of intensive treatment in an emergency room or at home for allergic bronchospasm, blood dyscrasias, convulsions, alanine aminotransferase (ALT)>3× upper limit of normal range (ULN) associated with total bilirubin>2×ULN, asymptomatic ALT increase>10×ULN, development of drug dependency or drug abuse, ALT increase≥2×ULN, hsCRP>10 mg/L for ≥72 hours, cardiac troponin I (cTnI)>2×ULN, a ventricular depolarization and repolarization time (QT) on an electrocardiogram (ECG) machine wherein the QT is automatically corrected by the ECG machine (QTc) that is QTc≥500 ms, severe skin reactions local to the site of IP injection and a level of C-reactive protein (CRP) is less than 20 mg/L. The methods used to calculate the afore-mentioned events are discussed in detail in the examples presented below. Methods used to calculate the afore-mentioned events are commonly know to those skilled in the art.

Intracellular signaling after ligation of IL-4 and IL-13 with their cell surface receptors is mediated in part by phosphorylation of the signaling molecule signal transducer and activator of transcription 6 (Stat6). Therefore, inhibition of Stat6 phosphorylation (pStat6) can be used to test the ability of a molecule to inhibit activation of the IL-4 and IL-13 receptors.

IL-4 and IL-13 stimulate the release of IL-6 and eotaxin from human idiopathic pulmonary fibrosis lung fibroblasts. Therefore, inhibition of IL-6 and eotaxin release can be used to test the ability of a molecule to inhibit activation of the IL-4 and IL-13 receptors.

An embodiment of the invention is an antibody that inhibits IL-4- or IL-13-induced STAT6 phophorylation, IL-6 release or eotaxin with an IC50 about 0.01 nM to about 100 nM. A further embodiment encompasses an IC50 about 0.1 nM to about 10 nM. A further embodiment encompasses an IC50 about 0.1 nM to about 10 nM. Additional embodiments of the invention are IC50 values about 0.1, 0.2, 0.3, 0.4, 0.5, 0.6, 0.7, 0.8, 0.9, 1.0, 1.1, 1.2, 1.3, 1.4 1.5, 1.6, 1.7, 1.8, 1.9, 2.0, 2.2., 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0 nM.

The term "about" when used in connection with a numerical value is meant to encompass numerical values within a range having a lower limit that is 5%, 10% or 15% smaller than the indicated numerical value and having an upper limit that is 5%, 10% or 15% larger than the indicated numerical value.

An embodiment of the invention is detection methods to measure total human antibody levels or the proportion of a specific antibody (for example, a bispecific antibody) or to measure anti-drug antibodies in a test sample. The test sample can be any bodily sample from a mammal. Nonlimiting examples include blood samples, serum samples or tissue samples. Detection methods may involve using a "capture device" in which one or more antibodies are attached to the capture device. Nonlimiting examples of "capture devices" include wells of a plate wherein the plate may include any number of wells such as a 12 well plate or a 96 well plate. However, capture devices are not limited to plates but may include any substrate that an antibody may attach to, for example, an elution column. An embodiment of the invention utilizes tag-labeled antibodies. The tag can be any tag capable of detection. Nonlimiting examples include fluorescent tags such as rhodamine, enzymatic tags such as luciferase or sulfo-tags.

EXAMPLES

The instant invention may be better understood by reference to the following non-limiting Examples, which are exemplary of the invention. The Examples presented below should in no way be construed as limiting the broad scope of the invention.

The terms "huTBTI3_2_1" and "SAR156597" are interchangeable and refer to the same dual V region antibody-like protein comprising a variable light chain comprising amino acid sequences SEQ ID NO:1 and SEQ ID NO:3 and a variable heavy chain comprising amino acid sequences SEQ ID NO:2 and SEQ ID NO:4.

Example 1

Cloning and Generation of Humanized Anti-IL-4/IL-13 Bispecific Antibodies

The cloning and generation of humanized anti-IL-4/IL-13 bispecific antibodies is described in WO2009/052081 (PCT/US2008/079787), herein incorporated by reference in its entirety. For ease of reference, a brief description follows.

The format used for the expression of bispecific antibodies (BsAb) is an IgG variant of the dual domain double head format described in U.S. Pat. No. 5,989,830. In this format an IgG molecule is elongated at its N-terminus on the corresponding heavy and light chains, by an additional variable domain of a second antibody. Thus, the resulting IgG molecule is a heterotetramer composed of two heavy and two light chains. The heavy chains consist of two variables heavy domains (VH1-VH2) deriving from two different antibodies joined together by a linker composed of ten amino acids (G4S)$_2$ and fused to the IgG4 constant domain. The light chains consist of two variables light domains (VL1-VL2) deriving from two different antibodies joined together by a linker composed of ten amino acids (G4S)$_2$ and fused to the constant kappa region.

Sequences for the variable heavy and light domains of the 8D4-8 variants (8D4-8; mouse anti-IL-4 monoclonal antibody clone 8D4-8 from Biozol diagnostica Vertrieb GmbH, Eching Germany; Biozol is the German distributor of BioLegend, San Diego, Calif., USA) were generated by PCR introducing a BamHI restriction site (GGATCC) at their respective 5'-ends encoding a part of the (G4S)$_2$-(GGATCC)-8D4-8. The 3' sequence of the VH of the 8D4-8 humanized variants ended with an ApaI restriction site (encoding the first amino acids of the CH1 domain) for a later fusion to the IGHG4 sequence (Q569F4, with deletion of the terminal Lys and a double mutation S241P and L248E). The 3'-end of the VL8D4-8 ended with a BsiWI restriction site encoding the first two amino acids of the constant kappa chain for a later fusion to IGKC (Gene Bank Accession Number Q502W4).

Sequences for the variable heavy and light domains of the B-B13 variants (B-B13; mouse anti-IL-13 monoclonal antibody clone B-B13 from Cell Sciences, Inc., Canton, Mass. USA) were generated by PCR introducing a BamHI restriction site at their respective 3'-ends encoding a part of the (G4S)$_2$-(B-B13)-(GGA GGC GGA GGG TCC GGA GGC GGA GGATCC (SEQ ID NO: 7)). Both sequences for the VH and VL of the B-B13 variants were generated with a NheI restriction site at their respective 5'-ends, followed by an ATG start codon and a leader peptide encoding sequence.

The VH of B-B13 and 8D4-8 were fused together through their BamHI sites within the (G4S)$_2$ linker. The VL of B-B13 and 8D4-8 were fused to each other through their BamHI sites within the (G4S)$_2$ linker. Hence the tandems of heavy and the light chains generated had the following composition.

Bispecific antibody heavy chain: NheI-Leader peptide-VH-B-B13-(G4S)$_2$-VH 8D4-8-ApaI.

Bispecific antibody light chain: NheI-Leader peptide-VL-B-B13-(G4S)$_2$-VL 8D4-8-BsiWI.

All intermediate PCR fragments were cloned into the pCR®4-TOPO using the Invitrogen TOPO TA cloning kit (Cat #: 45-0641) and sequenced using M13forward and M13 reverse primers.

After sequence validation the heavy chain tandems were fused through their ApaI site to the IGHG4 sequence and the variable light chain tandems were fused through their BsiWI site to IGKC. The created dual domain heavy chain and light chain were digested with NheI and HindIII and each ligated into the NheI/HindIII sites of the episomal expression vector pXL, creating the plasmids for mammalian expression of the TBTI-heavy and light chains respectively.

Four humanized bispecific anti-IL-4/anti-IL-13 constructs were generated based on the following combinations of humanized VH and VL versions of B-B13 and 8D4-8 as shown in Table 1. The corresponding light and heavy chain sequences are shown in Table 2.

TABLE 1

| Bispecific anti-IL-4/anti-IL-13 Antibodies | | |
|---|---|---|
| Bispecific anti-IL-4/anti-IL-13 Ab | Anti-IL-13 Fv | Anti-IL-4 Fv |
| huTBTI3_1_1 | B-B13 VL3 × VH2 | 8D4-8 VL1 × VH2 |
| huTBTI3_2_1 | B-B13 VL3 × VH2 | 8D4-8 VL1 × VH1 |
| huTBTI3_1_2 | B-B13 VL2 × VH2 | 8D4-8 VL1 × VH2 |
| huTBTI3_2_2 | B-B13 VL2 × VH2 | 8D4-8 VL1 × VH1 |

TABLE 2

Sequences of Humanized Variable Domains and Linker Sequence

Anti-IL13 hB-B13 VL3 (SEQ ID NO: 1):
DIVLTQSPAS LAVSLGQRAT ISCRASESVD SYGQSYMHWY
QQKAGQPPKL LIYLASNLES GVPARFSGSG SRTDFTLTID
PVQAEDAATY YCQQNAEDSR TFGGGTKLEI K CDRs are RASESVDSYGQSYMH (SEQ ID NO: 8),
LASNLES (SEQ ID NO: 9), and QQNAEDSRT
(SEQ ID NO: 10).

Anti-IL13 hB-B13 VH2 (SEQ ID NO: 2):
EVQLKESGPG LVAPGGSLSI TCTVSGFSLT DSSINWVRQP
PGKGLEWLGM IWGDGRIDYA DALKSRLSIS KDSSKSQVFL
EMTSLRTDDT ATYYCARDGY FPYAMDFWGQ GTSVTVSS CDRS are GFSLTDSSIN (SEQ ID NO: 11), DGRID
(SEQ ID NO: 12), and DGYFPYAMDF (SEQ ID NO: 13.)

Anti-IL4 h8D4-8 VL1 (SEQ ID NO: 3):
DIQMTQSPAS LSVSVGDTIT LTCHASQNID VWLSWFQQKP
GNIPKLLIYK ASNLHTGVPS RFSGSGSGTG FTLTISSLQP
EDIATYYCQQ AHSYPFTFGG GTKLEIKR CDRS are HASQNIDVWLS (SEQ ID NO: 14), KASNLHTG
(SEQ ID NO: 15), and QQAHSYPFT (SEQ ID NO: 16).

Anti-IL4 h8D4-8 VH1 (SEQ ID NO: 4):
QVQLQQSGPE LVKPGASVKI SCKASGYSFT SYWIHWIKQR
PGQGLEWIGM IDPSDGETRL NQRFQGRATL TVDESTTAY
MQLRSPTSED SAVYYCTRLK EYGNYDSFYF DVWGAGTLVT
VSSA CDRs are GYSFTSYWIH (SEQ ID NO: 17), IDPSDGETR
(SEQ ID NO: 18) and LKEYGNYDSFYFDV
(SEQ ID NO: 19).

TABLE 2-continued

Sequences of Humanized Variable Domains and
Linker Sequence

Anti-IL4 h8D4-8 VH2 (SEQ ID NO: 5):
QVQLQQSGPE LVKPGASVKI SCKASGYSFT SYWIHWIKQR
PGQGLEWIGM IDASDGETRL NQRFQGRATL TVDESTSTAY
MQLRSPTSED SAVYYCTRLK EYGNYDSFYF DVWGAGTLVT
VSSA CDRs are GYSFTSYWIH (SEQ ID NO: 20), IDASDGETR
(SEQ ID NO: 21), and LKEYGNYDSFYFDV
(SEQ ID NO: 22).

Linker Sequence (SEQ ID NO: 6)
GGGGSGGGGS

Underline indicates amino acid changes made for humanization or to remove residues subject to modification or acid lability. Bold indicates the CDR Example 2

Effect of huTBTI3_2_1 on IL-4- or IL-13-Induced STAT6 Phosphorylation in Human Whole Blood Monocytes Human sodium citrate anti-coagulated whole blood was obtained from an on-site normal donor panel. Donor numbers 245, 217, 229 and 002 were used.

huTBTI3_2_1 was generated at sanofi-aventis, batch no. LP08059, supplied at 5.63 mg/ml in phosphate buffered saline (PBS) and stored at 4° C.

Recombinant human IL-13 (lyophilized) from R&D Systems, catalog no. 213-IL, was reconstituted with PBS containing 0.2% bovine serum albumin at 10 μg/ml. Final concentration of IL-13 used in the assay was 3 ng/ml in complete RPMI medium. Recombinant human IL-4 (lyophilized) from AMS Biotechnology LTD, catalog no. 111-40-134, was reconstituted with PBS containing 0.2% bovine serum albumin at 20 μg/ml. Final concentration of IL-4 used in the assay was 1 ng/ml in complete RPMI medium.

huTBTI3_2_1 was serial diluted with complete RPMI medium to make 10× solutions, and mixed with 100 μl of normal human peripheral blood per well in a 96-deep-well plate to reach final concentrations of huTBTI3_2_1 at 100 nM, 33.33 nM, 11.11 nM, 3.70 nM, 1.24 nM, 0.41 nM, 0.14 nM, 0.05 nM, 0.02 nM, and 0.005 nM for donor numbers 245, 217 and 002. For donor number 229, the final concentrations of huTBTI3_2_1 tested were 100 nM, 33.33 nM, 11.11 nM, 3.70 nM, 1.24 nM, 0.41 nM and 0.14 nM.

The plate was incubated in 37° C., 5% $CO_2$ for 15 to 30 minutes. Then recombinant human IL-4 (1 ng/ml) or IL-13 (3 ng/ml) were added to each well, and the plate was further incubated in 37° C., 5% $CO_2$ for 15 minutes. Blood cells were then lysed/fixed with lysis/fix buffer for 10 minutes at 37° C., centrifuged at 300×g for 5 minutes at room temperature. Supernatants were removed and the remaining cell pellet was washed once with phosphate-buffered saline. The cells were permeabilized with pre-cooled methanol for 30 minutes in 4° C. and then washed once with FACS stain buffer (BD, catalog no. 554656). Fluorescence-labeled antibodies (anti-phospho-Stat6-Alexa Fluor 647 at 1:5 final dilution, and anti-CD33-FITC at 1:10 final dilution) were added to cells and incubated at room temperature in the dark for 30 minutes. After wash with FACS stain buffer, cells were acquired through a FACS Calibur™ flow cytometer to generate FACS data.

FACS data were analyzed by using CellQuest Software™ (BD, version 5.2). Dot plots were created using CD33 staining (fluorescein isothiocyanate) versus pStat6 staining (Alexa Fluor 647) (see FIG. 1). Total monocytes were gated based on side scatter versus forward scatter. CD33$^+$ staining, Stat6-phosphorylation positive monocytes were gated based on the fluorescence intensity between baseline control and IL-4 or IL-13 stimulated samples in the absence of huTBTI3_2_1. Percent of pStat6 positive monocytes among total monocytes were obtained from region statistics based on CellQuest software (BD, version 5.2).

The effects of huTBTI3_2_1 on IL-4- or IL-13-induced Stat6 phosphorylation were determined using percent inhibition of maximum response (Stat6 phosphorylation) in IL-4- or IL-13-stimulated monocytes.

The maximum response was defined as the percent of pStat6$^+$ cells generated by IL-4 or IL-13 stimulation in the absence of huTBTI3_2_1. The percent of pStat6$^+$ cells generated from unstimulated monocytes was used as baseline signal. The percent of maximum response was calculated using the following equation:

$$\text{Percent (\%) of maximum response} = \frac{\% \, pStat6^+_{SAR156597} - \% \, pStat6^+_{baseline}}{\% \, pStat6_{maximum \, response} - \% \, pStat6_{baseline}} \times 100\%$$

Dose-response curves were plotted as Y: % of maximum response versus X: concentrations (nM) of huTBTI3_2_1 by SPEED v2.0-LTS to calculate the concentration giving 50% of maximum response ($IC_{50}$).

Dose response curve was modeled by the four-parameter logistic model:

$$\% \text{ Maximum\_response} = c + \frac{d-c}{1 + \exp\{b(\log(\text{dose}) - \log(e))\}}$$

The parameters c and d are the lower and upper limits, negative b is the relative slope around e, and the e parameter is $IC_{50}$ and is the dose producing a response half-way between the upper limit, d and lower limit, c. The four parameters (b,c,d,e) were estimated by non-linear least squares method. SAS procedure NLIN in SAS system release 8.2 for sun solaris via SPEED v2.0-LTS internal software was used. After obtaining the $IC_{50}$ estimation from each of the three curves, the geometric mean of the 3 $IC_{50}$ values were calculated.

huTBTI3_2_1 inhibited IL-4-induced Stat6 phosphorylation in donors 245, 229 and 217 with $IC_{50}$s of 1.32 nM, 0.73 nM, and 0.78 nM respectively. huTBTI3_2_1 inhibited IL-13-induced Stat6 phosphorylation in donors 245, 229 and 002 with $IC_{50}$s of 2.65 nM, 3.68 nM, and 1.32 nM respectively.

The geometric mean $IC_{50}$s of huTBTI3_2_1 in inhibiting IL-13 or IL-4-induced Stat6 phosphorylation from 3 separate experiments were 2.34 nM and 0.91 nM, respectively (Table 3).

TABLE 3

$IC_{50}$ values of huTBTI3_2_1 in inhibiting Stat6 phosphorylation induced by IL-13 or IL-4 in human blood monocytes.

| Blood donor no. | $IC_{50}$ (nM) Inhibition of IL-13 | $IC_{50}$ (nM) Inhibition of IL-4 |
|---|---|---|
| 245 | 2.65 | 1.32 |
| 229 | 3.68 | 0.73 |

TABLE 3-continued

IC$_{50}$ values of huTBTI3_2_1 in inhibiting Stat6 phosphorylation induced by IL-13 or IL-4 in human blood monocytes.

| Blood donor no. | IC$_{50}$ (nM) Inhibition of IL-13 | IC$_{50}$ (nM) Inhibition of IL-4 |
|---|---|---|
| 217 | * | 0.78 |
| 002 | 1.32 | ** |
| Geometric Mean (95% CI) | 2.34 (0.64 to 8.61) | 0.91 (0.41 to 2.04) |

* For donor 217, only IL-4 was tested
** For donor 002, only IL-13 was tested
95% CI = 95% confidence interval Example 3

Effect of huTBTI3_2_1 on IL-4- or IL-13-Induced IL-6 Release and Eotaxin Release from Human IPF Pulmonary Fibroblasts Human lung fibroblast of idiopathic pulmonary fibrosis (IPF) patient, designation LL97A (AIMy), item number CCL-191, F-12K Medium (Kaighn's Modification of Ham's F-12 Medium) and Fetal Bovine Serum (FBS) were from the American Type Culture Collection (ATCC, Manassas, Va.). Albumin from bovine serum (BSA) was from Sigma-Aldrich (St. Louis, Mo.). Recombinant human IL-13 (rhIL-13) was from PeproTech (Rocky Hill, N.J.); Recombinant human IL-4 (rhIL-4) was from R&D SYSTEMS (Minneapolis, Minn.). DuoSet ELISA Development System for human CCL11/Eotaxin and IL-6 were both from R&D SYSTEMS.

LL97A cells at passage 7 were plated on a 96 well cell culture plate at 20,000 cells per well in F-12K Medium with 15% FBS and incubated at 37° C., 5% CO$_2$ in a humidified incubator for 24 hours. The medium was then replaced with F-12K Medium with 0.1% BSA and the plate was incubated overnight at 37° C., 5% CO$_2$ in a humidified incubator for serum starvation. Cells were then treated overnight at 37° C., 5% CO$_2$ in a humidified incubator with a 3-fold serially diluted, 8 concentration points of huTBTI3_2_1 with a combination of 15 ng/ml (1.2 nM) rhIL-13 plus 5 ng/ml (0.36 nM) rhIL-4 in a total volume of 200 µl per well. Each treatment was in triplicate. 150 µl per well of the cell culture supernatant was then taken and diluted into 300 µl F-12K Medium with 0.1% BSA (3-fold dilution) for eotaxin and IL-6 ELISA.

The ELISAs were carried out according to the instructions of DuoSet ELISA Development System for human CCL11/Eotaxin and IL-6 of R&D SYSTEMS. The ELISA plates were read in a SPECTRA$_{MAX}$340PC plate reader (Molecular Devices) for optical density (OD) at 450 nm and 540 nm. OD values at 540 nm were subtracted from OD at 450 nm before calculation.

Figure 2:
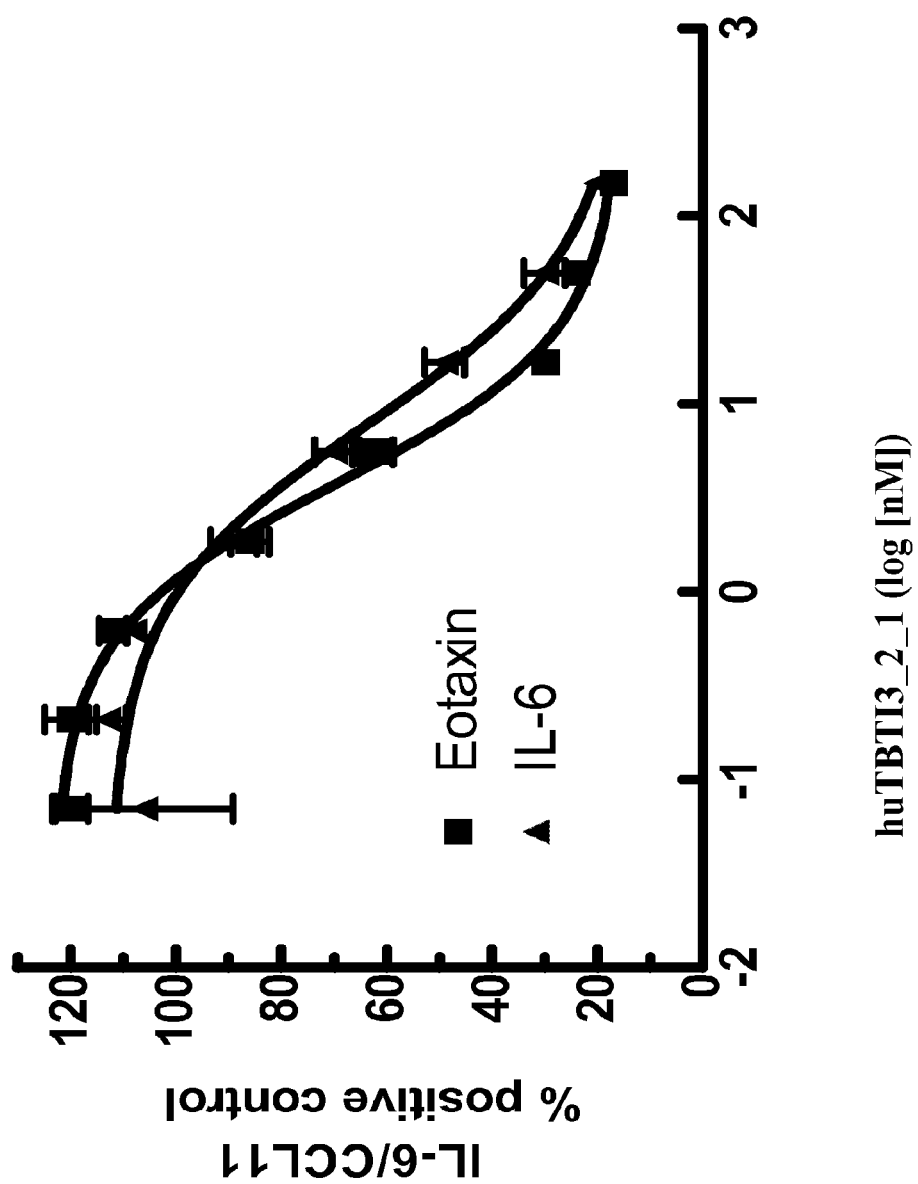
FIG. 2 shows the effects of huTBTI3_2_1 on IL-4 and IL-13-stimulated IL-6 and eotaxin release from human lung fibroblasts from a idiopathic pulmonary fibrosis patient.
Figure 3:
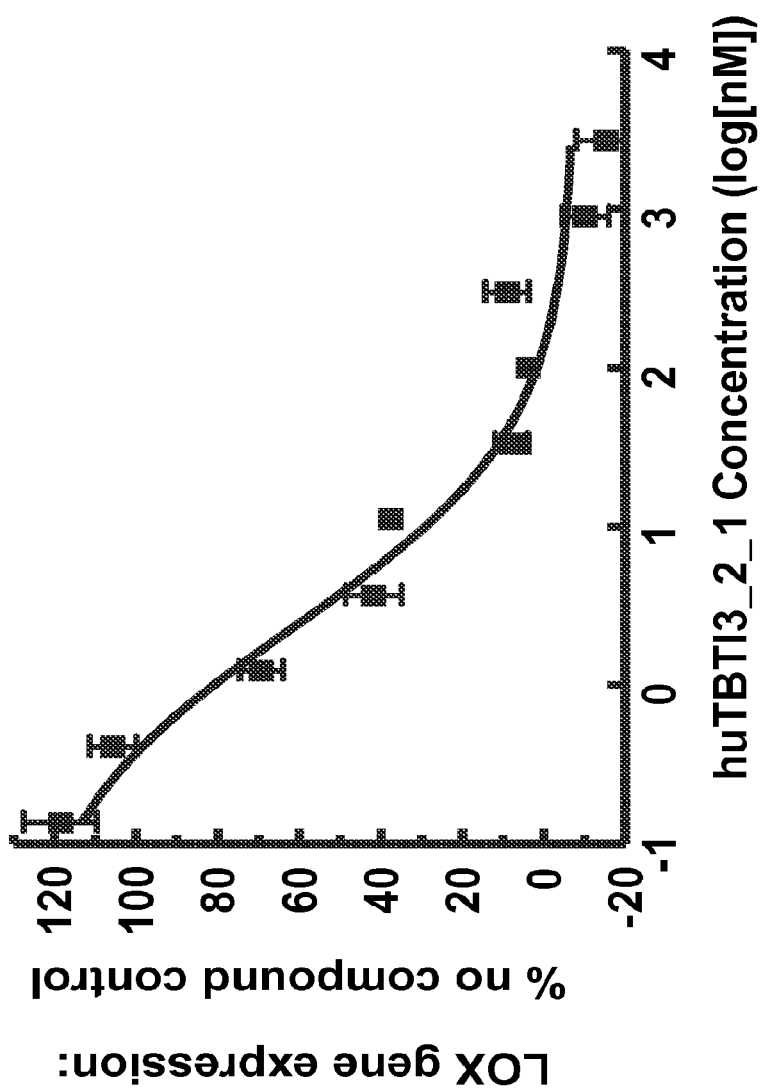
FIG. 3 shows the effects of huTBTI3_2_1 on IL-4 and IL-13 induced LOX expression in idiopathic pulmonary fibrosis pulmonary fibroblasts.

CCL11 (eotaxin) and IL-6 levels in supernatants were derived with 4-parameters standard curve in SOFTmax. Sample average without rhIL-13/rhIL-4 stimulation (basal level) was subtracted from each sample and each sample was then compared with sample average of rhIL-13/rhIL-4 stimulation without huTBTI3_2_1 (set as 100% positive) for % positive control. Error bars represent standard error of mean of triplicate biological samples (cell treatment). huTBTI3_2_1 suppressed IL-4/IL-13-stimulated IL-6 release with an IC50=7.8 nM and suppressed IL-4/IL-13-stimulated eotaxin release with an IC50=3.8 nM (FIG. 2).

Example 4

Effect of huTBTI3_2_1 on IL-4- or IL-13-Induced LOX Expression in IPF Pulmonary Fibroblasts To assess the effects of huTBTI3_2_1 on IL-4 and IL-13 stimulated expression of profibrotic enzymes, mRNA levels of lysyl oxidase (LOX) was measured in a similar experiment as shown in Example 3. LOX gene expression was determined by Taqman and was normalized to the housekeeping gene GAPDH.

Standard Taqman methods were used. Briefly, cells lysates were prepared with the Cells-to-Ct kit (ABI, Catalog No. AM1729). 20× Human GAPDH TaqMan Endogenous Control Primer/Probe Set: Applied Biosystems, Part Number 4310884E, Probe Dye: VIC-TAMRA. 20× human primer probe sets (probes labeled with FAM dye at 5' end and nonflourescent quencher at 3' end) was Human LOX: AOD from Applied Biosystems, Gene Name: lysyl oxidase; Assay ID: Hs00184700_m1. Reverse Transcription (RT) was performed on a PELTIER THERMAL CYCLER with 4 block assembly, Model PTC 225, from MJ RESEARCH. The Taqman instrument was 7900HT Fast Real-Time PCR System, Applied Biosystems, Part number: 4330966; Serial number: 279001674. 20 ul of cell lysate per sample (or water for no template control) was added to 80 ul RT master mix (50 ul 2×RT buffer, 5 ul 20×RT Enzyme mix, 25 ul RNase-free water). RT sequence: reverse transcription at 37 degree C. for 60 minutes, RT inactivation at 95 degree C. for 5 minutes, hold at 4 degree C. forever. For Taqman real-time PCR, PCR cocktail was prepared as follows: 10 ul Taqman gene expression master mix (2×), 1 ul Taqman gene expression assay (20×), 1 ul human GAPDH endogenous control (20×), 3 ul water, add 5 ul DNA. Taqman cycling conditions: UDG incubation hold was 1 rep at 50 degree C. for 2 minutes, enzyme activation was 1 rep at 95 degree C. for 10 minutes, and PCR cycle was 40 reps at 95 degree C. for 15 seconds followed by 60 degree C. for 1 minute.

LOX activity results in crosslinking of extracellular collagen and elastin, resulting in stabilization of the extracellular matrix, and its upregulation has been implicated in experimental pulmonary fibrosis (Rodriguez, C. et al., Drug News Perspect. 21:218-224, 2008).

Figure 4:
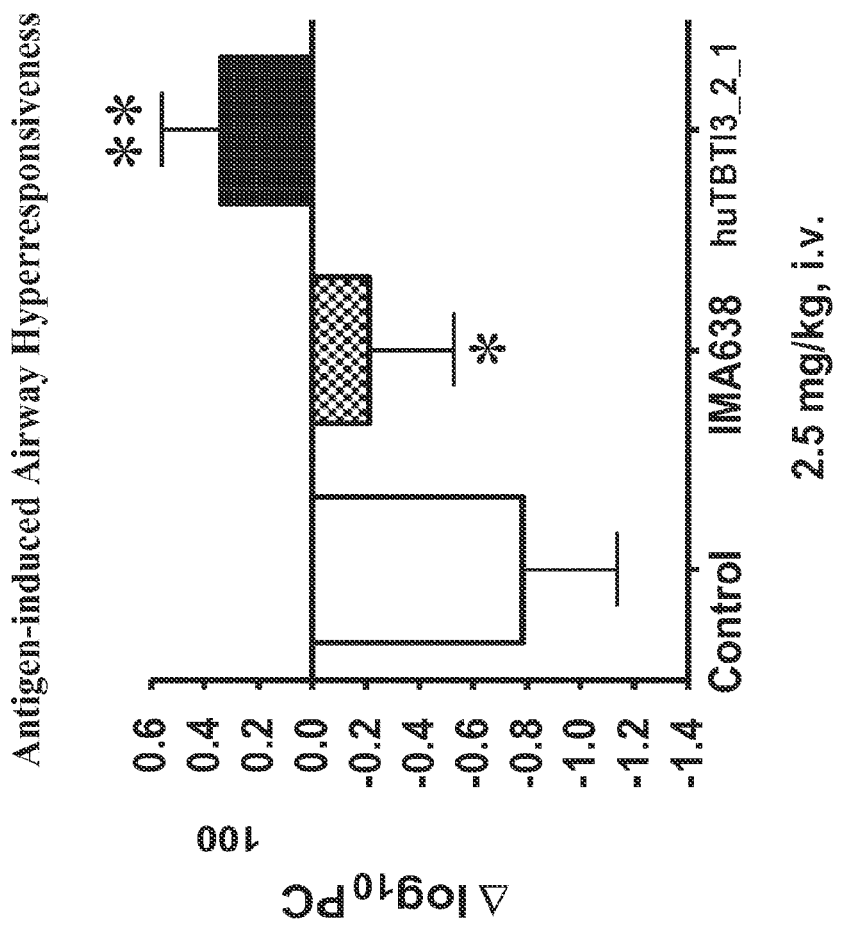
FIG. 4 shows the effects of huTBTI3_2_1 on antigen-induced airway hyperresponsiveness against allergen induced acute asthma in cynomolgus monkeys. Data are represented as mean±s.e.m. *$p<0.05$, **$p<0.01$ compared with control antibody-treated group.

IL-4 and IL-13 induced LOX gene expression, and this expression was inhibited by huTBTI3_2_1 in a dose-dependent manner, with an IC50 of 3-6 nM (FIG. 4). This effect has been observed in pulmonary fibroblasts from at least 3 IPF patients. IL-4 and IL-13 failed to induce genes for fibronectin and insulin-grwoth factors (IGF; data not shown). This data demonstrate pulmonary fibroblasts from IPF subjects express functional IL-4/IL-13 receptors whose activation by IL-4 and IL-13 results in direct and indirect profibrotic effects. The activation of the profibrotic effects of pulmonary fibroblasts from IPF patients with the cytokines IL-4 and IL-13 is inhibited by huTBTI3_2_1.

Example 5

Effect of huTBTI3_2_1 Against Allergen-Induced Acute Asthma in Cynomolgus Monkeys Since huTBTI3_2_1 does not bind to rodent IL-4 or IL-13, we were not able to test the molecule for protective effects in rodent models of lung fibrosis. Although huTBTI3_2_1 does bind to cynomolgus monkey IL-4 and IL-13, there are no models of lung fibrosis available in this species. Therefore, to test the ability of huTBTI3_2_1 to inhibit effects of IL-4 and IL-13 in the pulmonary compartment, we investigated its protective effects in a model of acute asthma in a non-human primate species (cynomolgus monkeys). The study used male cynomolgus monkeys (*Macaca fascicularis*) that are naturally sensitized to *Ascaris suum* allergens.

To induce airway hyperresponsiveness and airways inflammation, monkeys were challenged with inhaled *Ascaris suum* extract. Six days before antigen challenge, monkeys received huTBTI3_2_1 (2.5 mg/kg IV), or the same dose of a comparator antibody (anti-IL-13, IMA638) or a control antibody (control antibody does not bind IL-4 or IL-13).

Bronchoconstrictor responses (increases in lung resistance) to ascending doses of inhaled methacholine were measured using a MI² respiratory analyzer. Measurements were made at least 24 hours before challenge, and again 24 hours after challenge. Airway responsiveness was calculated as the provocation concentration of methacholine required to cause a 100% increase in lung resistance ($PC_{100}$). Immediately after measurement of airway responsiveness, bronchoalveolar lavage was performed to allow counts of total leukocytes and eosinophils in the airways. Cell counts were expressed as cell numbers per ml of lavage fluid. The differences ( ) in methacholine $PC_{100}$ values and airway cell numbers before and after antigen challenge were calculated.

Blood samples were collected 24 hours before antigen challenge, and again 7 days after challenge, to allow assay of total immunoglobulin E (IgE) titers. The percent change in IgE titer was calculated.

Figure 5:
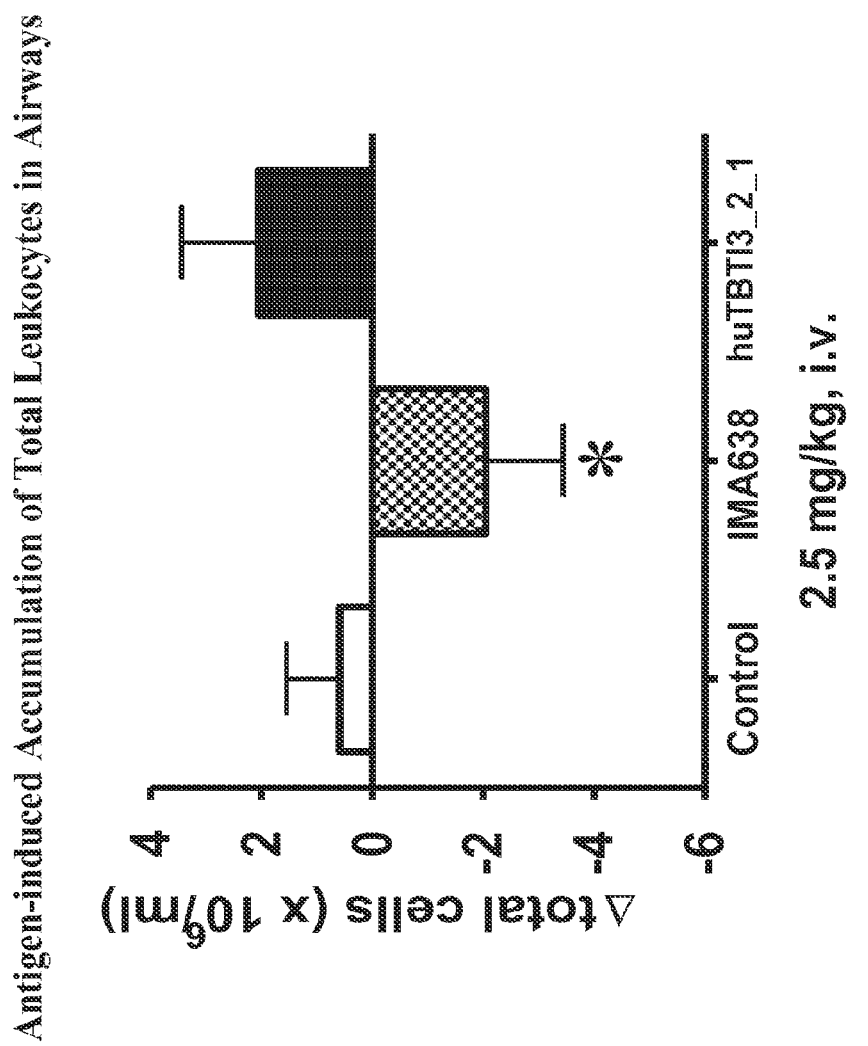
FIG. 5 shows the effects of huTBTI3_2_1 on antigen-induced accumulation of total leukocytes in airways against allergen induced acute asthma in cynomolgus monkeys. Data are represented as mean±s.e.m. *$p<0.05$, **$p<0.01$ compared with control antibody-treated group.
Figure 6:
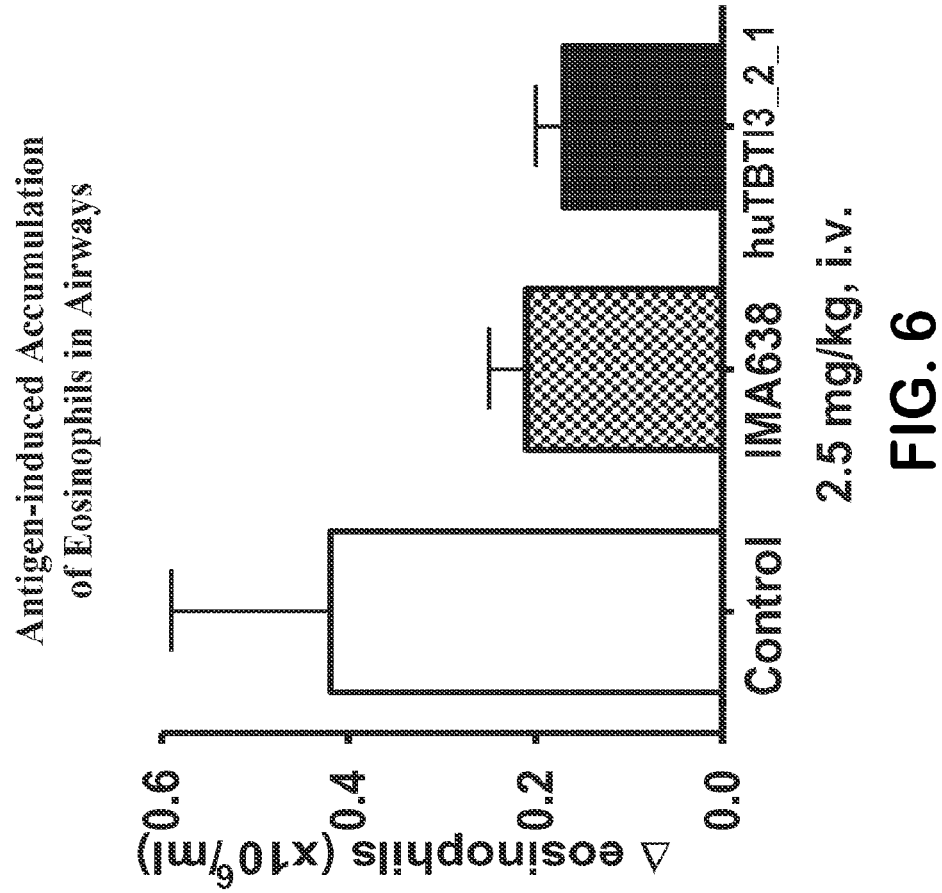
FIG. 6 shows the effects of huTBTI3_2_1 on antigen-induced accumulation of eosinophils in airways against allergen induced acute asthma in cynomolgous monkeys. Data are represented as mean±s.e.m. *$p<0.05$, **$p<0.01$ compared with control antibody-treated group.
Figure 7:
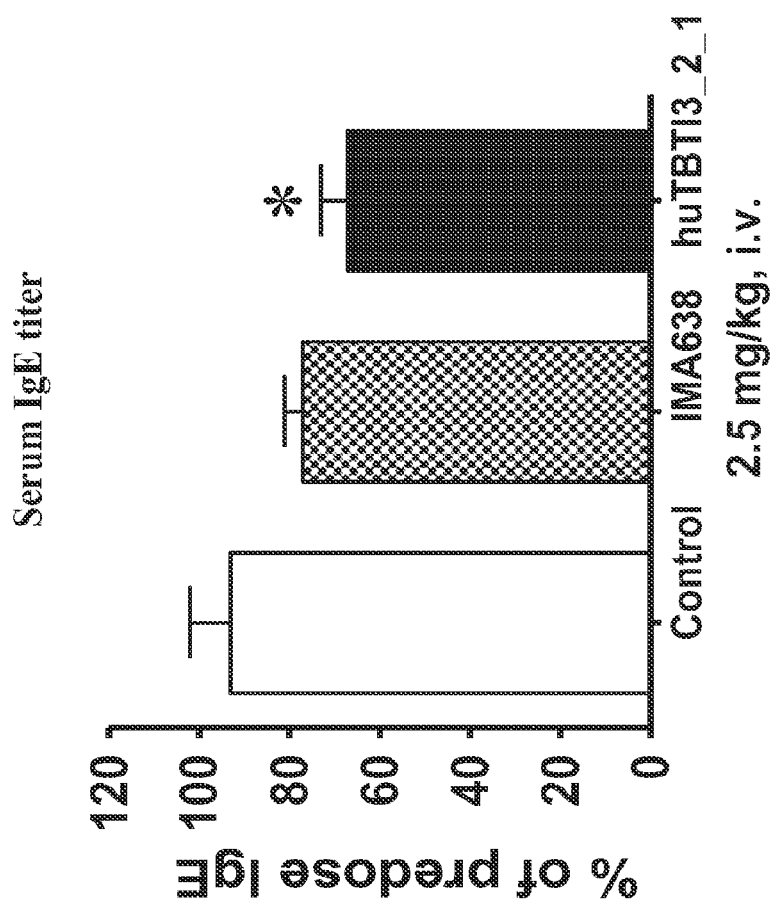
FIG. 7 shows the effects of huTBTI3_2_1 on serum IgE titer from allergen induced acute asthma in cynomolgous monkeys. Data are represented as mean±s.e.m. *$p<0.05$, **$p<0.01$ compared with control antibody-treated group.

Antigen challenge caused airway hyperresponsiveness (i.e. a decreased methacholine PC100 (FIG. 4) and an accumulation of total leukocytes and eosinophils in the airways (FIGS. 5 and 6). When compared with control antibody, prophylactic treatment with either huTBTI3_2_1 (2.5 mg/kg) or IMA638 (2.5 mg/kg) significantly suppressed the development of airway hyperresponsiveness. IMA638, but not huTBTI3_2_1, significantly reduced the antigen-induced accumulation of total leukocytes in the airways (FIGS. 5 and 6). huTBTI3_2_1 or IMA638 had no significant effects on the accumulation of eosinophils. huTBTI3_2_1, but not IMA638, significantly reduced the IgE titer (FIG. 7).

Example 6

Effects of huTBTI3_2_1 Against TF-1 Cell Proliferation Induced by Recombinant Human and Cynomologus Monkey IL-4 and IL-13 In Vitro As a further study of the ability of huTBTI3_2_1 to inhibit IL-4 and IL-13-induced cell activation, the $IC_{50}$ values for inhibition of TF-1 cell (a human erythrocyte line) proliferation induced by recombinant human IL-4 (hIL-4) and IL-13 (hIL-13) was determined. IL-4- or IL-13-induced TF-1 cell proliferation is commonly used in the literature as an assay for the bioactivities of these cytokines.

TF-1 cells were incubated for 72 hours with huTBTI3_2_1 at a range of concentrations together with either hIL-4 (5 ng/ml), hIL-13 (15 ng/ml), cIL-4 (5 ng/ml) or cIL-13 (30 ng/ml). 3-(4,5-dimethylthiazol-2-yl)-2,5-diphenyltetrazolium bromide was added for the final 3 hours as a marker of cell proliferation. Optical density values at 490 nm were then recorded.

huTBTI3_2_1 markedly inhibited hIL-4, cIL-4, hIL-13 and cIL-13-induced TF-1 cell proliferation in a concentration-dependent manner and with comparable potencies. The geometric mean $IC_{50}$ values were 2.03 nM and 0.53 nM respectively against hIL-4 and cIL-4-induced proliferation, and 3.02 nM and 0.45 nM respectively against hIL-13 and cIL-13-induced proliferation are shown in Table 4.

TABLE 4

Inhibitory effects of huTBTI3_2_1 against TF-1 cell proliferation induced by recombinant human and cynomolgus monkey IL-4 and IL-13

|  | Mean $IC_{50}$, nM |
| --- | --- |
| Inhibition of human IL-4 | 2.03 |
| Inhibition of human IL-13 | 3.02 |
| Inhibition of cynomolgus IL-4 | 0.53 |
| Inhibition of cynomolgus IL-13 | 0.45 |

$IC_{50}$ = Concentration of SAR156597 that inhibits proliferation by 50%.
n = 3 (experimental triplicates).

The results of this study demonstrate that huTBTI3_2_1 neutralizes the biological activities of IL-4 and IL-13 as shown by the decreased cell proliferation of TF-1 cells following stimulation by these cytokines. Hence, targeting these cytokines with huTBTI3_2_1 offers a therapeutic approach that may interrupt the fibrotic process in patients with IPF.

Example 7

Effects of SAR156597 on IL-4 and IL-13 Mediated TGFβ Release

Figure 8:
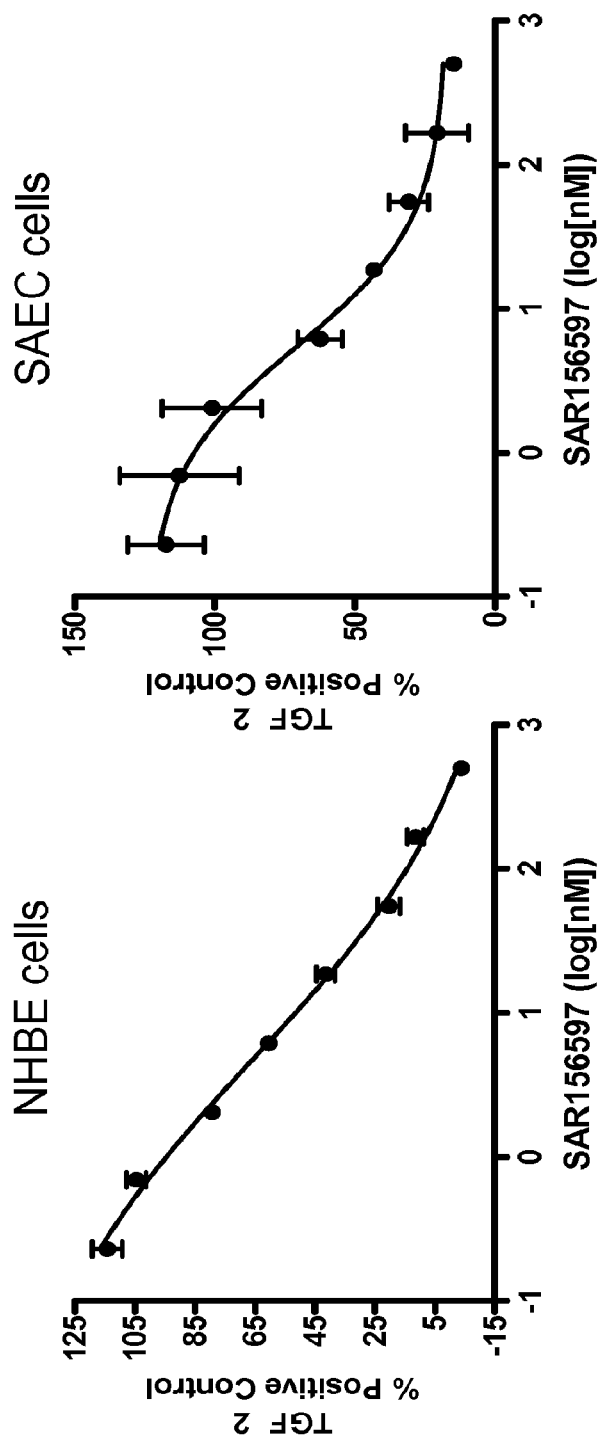
FIG. 8 shows the effects of SAR156597 on IL-4 and IL-13 mediated TGFβ release from normal human bronchial epithelial cells (NHBE; left panel) and human small airway epithelial cells (SAEC; right panel).

IL-4 and IL-13 have been shown to stimulate TGFβ release from human pulmonary epithelial cells. We determined the effect of SAR156597 on release of this profibrotic cytokine from human small airway epithelial cells (SAEC) and human bronchial epithelieal cells (NHBE). SAEC were plated on 12 well plates at 50,000 cells per well in small airway epithelial culture medium (Lonza) and cultured for 3 days. NHBE cells were cultured at 75,000 cells per well in 12 wells plates in BMEM (Lonza) for 3 days. Cells were starved with basal medium containing 5 μg/ml insulin and 5 μg/ml transferrin overnight and then treated with a combination of 15 ng/ml (1.2 nM) rhIL-13 plus 5 ng/ml (0.36 nM) rhIL-4 in the presence of a range of concentrations of SAR156597. TGFβ2 in cell supernatants was determined by ELISA (E-biosciences, cat#BMS254). SAR156597 inhibited IL-4 and IL-3 stimulated TGFβ2 release from NHBE and SAEC cells in a dose-dependent manner (FIG. 8).

Example 8

Pharmacokinetic Study after Repeated Intravenous 5 Minutes Infusions of 2.5 mg/kg of Humanized Bispecific Anti-IL-4/IL-13 (huTBTI3_2_1) Monoclonal Antibody to Cynomolgus Monkeys In this study the pharmacokinetic properties of huTBTI3_2_1, a humanized bispecific monoclonal antibody (BsAb) to IL-4/IL-13, was measured after repeat dose administration. The goal was to demonstrate that there was an accumulation of huTBTI3_2_1 over time and to monitor the animal production of anti-drug antibodies.

Male *Macaca fascicularis* (6-8 kg) were obtained from Charles River, Houston, Tex. Route of administration was by i/v perfusion in 5 minutes. Five doses were given serially. Blood samples (1 ml) were taken at the following time points: (first dose) 0 h, 0.5 h, 2 h, 4 h, 8 h, 24 h, 48 h, 72 h, 96 h, 120 h, 144 h, 168 h, 240 h; (second, third and fourth dose) 0 h, 0.5 h, 2 h, 24 h; (fifth dose) 0 h, 0.5 h, 2 h, 4 h, 8 h, 24 h, 48 h, 72 h, 96 h, 120 h, 144 h, 168 h, 240 h, 336 h, 504 h, 672 h, 840 h, 1008 h (h=hour).

Figure 9:
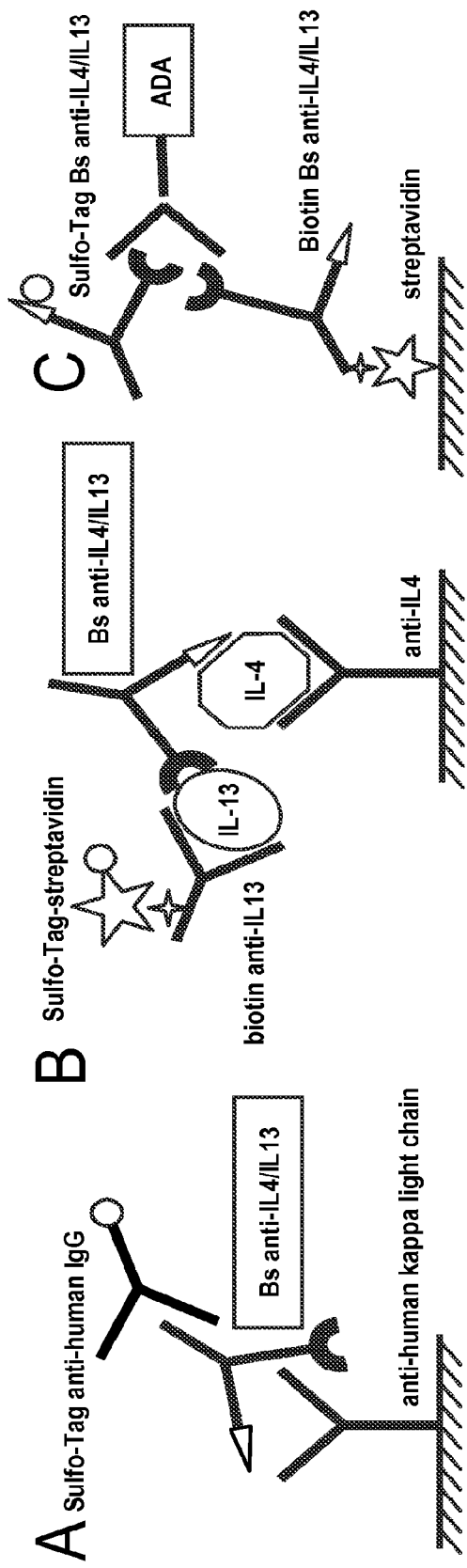
FIG. 9 shows a diagramatic representation of assays to measure total amount of human antibody in serum by measuring the concentration of human light chain K (panel A); to measure the proportion of functional antibodies to IL-4 and IL-13 (panel B); and to measure anti-drug antibodies (ADA) (panel C).

The serum samples were stored at −20° C. until analysis. Two separate assays using enhanced electro-chemiluminescence (EECL) assays with Meso Scale Discovery (MSD) technology were used to determine huTBTI3_2_1 levels in serum (FIG. 9). A third assay was developed to evaluate the anti-drug-antibody (ADA), i.e. anti-bispecific monkey antibodies, response.

The first assay (diagramed in panel A of FIG. 9) was designed to detect the total amount of human antibody in the serum by measuring the concentration of human light chain kappa). In this assay, MSD high binding plates were coated overnight with 1 µg/mL of mouse monoclonal anti-human kappa chain (clone 4G7; Abcam; #ab1936) diluted in PBS. Following an overnight incubation at 4° C. with serum samples diluted 1:1000 and 1:5000, Sulfo-Tag labeled goat anti-human antibody (MSD; # R32AJ-1) at a concentration of 1 µg/mL was added and detected using a MSD plate Sector Imager 6000.

The second assay (diagramed in panel B of FIG. 9) was designed to measure the proportion of bispecific antibody in the serum capable of binding IL-4 and IL-13 (measurement of the amount of functional antibody). In this assay, MSD high binding plates were incubated overnight at 4° C. sequentially with 2 µg/mL of a mouse anti-human IL-4 (clone 4D9; Ancell; #ANC-396), then with 200 ng/mL of recombinant human IL-4 (eBioscience, #34-8049) and finally with monkey sera diluted 1:1000 and 1:5000. Bound bispecific antibodies were revealed by sequential incubation with 200 ng/mL of recombinant human IL-13 (eBioscience; #34-8139, then with 200 ng/mL of biotinylated rabbit polyclonal anti-human IL-13 antibody (eBioscience; #13-7138) and finally with Sulfo-Tag streptavidin (MSD; # R32AA-1) at a concentration of 1 µg/mL.

Thirdly, ADAs were detected with a bridging assay (diagramed in panel C of FIG. 8). In brief, sera diluted 1:10 were incubated overnight at 4° C. with a mixture of biotinylated and Sulfo-tagged huTBTI3_2_1 (2 µg/mL of each final). Complexes were then trapped in streptavidin coated plates (MSD; #L11SA-1) by incubation for 4 hours at room temperature and revealed using a MSD plate Sector Imager 6000.

Standard sample concentrations were prepared in PBS containing 0.5% BSA as indicated in the following table. For the assay to detect the total amount of huTBTI3_2_1 there was no significant difference whether calibration samples were prepared in PBS containing 0.5% BSA, 0.1% monkey plasma or PBS containing 0.5% BSA only. For the assay to detect the fraction of huTBTI3_2_1 specific to IL-4 and IL-13 there was no significant difference whether calibration samples were prepared in PBS containing 0.5% BSA, 1% monkey plasma or PBS containing 0.5% BSA only. Both calibration curves were weighed by $1/x^2$ using a linear regression and shown to be linear within all calibration points ($R^2 > 0.98$).

TABLE 5

Standard Sample Concentrations

| Assay | Compound ID | Sample Matrix | Concentrations of Standards (ng/ml) |
|---|---|---|---|
| Total BsAb | huTBTI3_2_1 Batch #LP08059 | PBS, 0.5% BSA | 50; 16.7; 5.6; 1.9; 0.6; 0.2; 0.07 |
| BsAb specific to IL-4 and IL-13 | huTBTI3_2_1 Batch #LP08059 | PBS, 0.5% BSA | 200; 50; 12.5; 3.1; 0.8; 0.2; 0.05 |

In parallel to ADA measurements from sera, a data validation curve was obtained by mixing dilutions of a mock ADA with biotinylated and Sulfo-tagged huTBTI3_2_1. That antibody was a mouse anti-human IgG4 (Abcam; #ab1950-1) and showed the best signal to noise ratio out of several antibodies tested.

TABLE 6

Standard Sample Concentrations for ADA

| Assay | Compound ID | Sample Matrix | Concentrations of Standards (ng/ml) |
|---|---|---|---|
| ADA | Mock ADA | PBS, 0.5% BSA | 10000; 2500; 625; 156; 39; 9.7 |

The lower limits of quantitation (LLOQ) of huTBTI3_2_1 were 70 ng/mL and 5 ng/mL for total assay and specific assay respectively. The determination of ADA response is not quantitative but qualitative in comparison to the mock ADA response.

The pharmacokinetic parameters were calculated from the arithmetic mean of the serum concentrations/the individual animals following the 5th dose using the program WinNonLin 5.2., non-compartment model 202.

TABLE 7

Total concentrations of bispecific antibodies (BsAb) in monkey sera following repeated intravenous 5 minutes infusions of 2.5 mg/kg of huTBTI3_2_1 (batch #LP08059) in PBS. For each time point, values are mean concentrations out of three independent measurements done in triplicates.

| Dosing | Theoretical sampling time (h) from 1st dose | Theoretical sampling time (h) from last dose | Concentrations of total huTBTI3_2_1 [ng/mL] | | | | |
|---|---|---|---|---|---|---|---|
| | | | Monkey #1 | SD | Monkey #2 | SD | mean |
| dose 1 | 0 | 0 | <LLOQ | n.c. | <LLOQ | n.c. | n.c. |
| | 0.5 | 0.5 | 77000 | 23000 | 87100 | 25000 | 82100 |
| | 2 | 2 | 60000 | 13300 | 109000 | 45900 | 84500 |

TABLE 7-continued

Total concentrations of bispecific antibodies (BsAb) in monkey sera following repeated intravenous 5 minutes infusions of 2.5 mg/kg of huTBTI3_2_1 (batch #LP08059) in PBS. For each time point, values are mean concentrations out of three independent measurements done in triplicates.

| Dosing | Theoretical sampling time (h) from 1st dose | Theoretical sampling time (h) from last dose | Concentrations of total huTBTI3_2_1 [ng/mL] | | | | |
|---|---|---|---|---|---|---|---|
| | | | Monkey #1 | SD | Monkey #2 | SD | mean |
| | 4 | 4 | 74000 | 20800 | 81700 | 29400 | 77900 |
| | 8 | 8 | 54800 | 11900 | 64100 | 12000 | 59500 |
| | 24 | 24 | 60300 | 15200 | 77800 | 41400 | 69100 |
| | 48 | 48 | 58700 | 23800 | 51700 | 19400 | 55200 |
| | 72 | 72 | 41400 | 10600 | 38600 | 7290 | 40000 |
| | 96 | 96 | 45000 | 2080 | 48100 | 19600 | 46600 |
| | 120 | 120 | 50700 | 25600 | 45800 | 25800 | 48300 |
| | 144 | 144 | 53500 | 32400 | 53900 | 39800 | 53700 |
| | 168 | 168 | 31700 | 12000 | 34700 | 19300 | 33200 |
| | 240 | 240 | 28200 | 5170 | 20800 | 2270 | 24500 |
| dose 2 | 336 | 0 | 29700 | 7420 | 30500 | 15500 | 30100 |
| | 336.5 | 0.5 | 114000 | 27800 | 125000 | 9280 | 119500 |
| | 338 | 2 | 120000 | 20400 | 121000 | 12900 | 120500 |
| | 360 | 24 | 91600 | 19900 | 84000 | 9590 | 87800 |
| dose 3 | 504 | 0 | 83700 | 16400 | 47200 | 287 | 65500 |
| | 504.5 | 0.5 | 165000 | 18700 | 120000 | 18800 | 143000 |
| | 506 | 2 | 206000 | 13100 | 173000 | 15600 | 189500 |
| | 528 | 24 | 156000 | 18700 | 104000 | 10100 | 130000 |
| dose 4 | 672 | 0 | 101000 | 9300 | 69400 | 11300 | 85200 |
| | 672.5 | 0.5 | 151000 | 17600 | 169000 | 13000 | 160000 |
| | 674 | 2 | 186000 | 29200 | 202000 | 3990 | 194000 |
| | 696 | 24 | 164000 | 49500 | 135000 | 8050 | 150000 |
| dose 5 | 840 | 0 | 134000 | 11900 | 91600 | 361 | 113000 |
| | 840.5 | 0.5 | 212000 | 8650 | 206000 | 6180 | 209000 |
| | 842 | 2 | 219000 | 13100 | 174000 | 9480 | 197000 |
| | 844 | 4 | 183000 | 2480 | 143000 | 11200 | 163000 |
| | 848 | 8 | 161000 | 3310 | 170000 | 22000 | 166000 |
| | 864 | 24 | 218000 | 8340 | 205000 | 3340 | 212000 |
| | 888 | 48 | 141000 | 5090 | 114000 | 5350 | 128000 |
| | 912 | 72 | 196000 | 19100 | 154000 | 5540 | 175000 |
| | 936 | 96 | 243000 | 14800 | 128000 | 19300 | 186000 |
| | 960 | 120 | 97200 | 14900 | 159000 | 5310 | 128000 |
| | 984 | 144 | 127000 | 10000 | 92600 | 15100 | 110000 |
| | 1,008 | 168 | 150000 | 2040 | 102000 | 4600 | 126000 |
| | 1,080 | 240 | 132000 | 12200 | 94700 | 28300 | 114000 |
| | 1176 | 336 | 101000 | 19000 | 67900 | 13500 | 84500 |
| | 1344 | 504 | 100000 | 21300 | 55400 | 67500 | 77700 |
| | 1512 | 672 | 69400 | 12200 | 44500 | 9970 | 57000 |
| | 1680 | 840 | 61400 | 19100 | 31600 | 4500 | 46500 |
| | 1848 | 1008 | 51900 | 14100 | 22800 | 4320 | 37400 | n.c. not calculated;
LLOQ = 70 ng/mL

TABLE 8

Concentrations of bispecific antibodies (BsAb) reactive to IL-4 and IL-13 in monkey sera following repeated intravenous 5 minutes infusions of 2.5 mg/kg of huTBTI3_2_1 (batch #LP08059) in PBS. For each time point, values are mean concentrations out of three independent measurements done in triplicates.

| Dosing | Theoretical sampling time (h) from 1st dose | Theoretical sampling time (h) from last dose | Concentrations of functional huTBTI3_2_1 [ng/mL] | | | | |
|---|---|---|---|---|---|---|---|
| | | | Monkey #1 | SD | Monkey #2 | SD | mean |
| dose 1 | 0 | 0 | <LLOQ | n.c. | <LLOQ | n.c. | n.c. |
| | 0.5 | 0.5 | 104000 | 3370 | 115000 | 3510 | 110000 |
| | 2 | 2 | 80600 | 1030 | 152000 | 5300 | 116000 |
| | 4 | 4 | 100000 | 2610 | 110000 | 4830 | 105000 |
| | 8 | 8 | 70400 | 1200 | 85800 | 3930 | 78100 |
| | 24 | 24 | 74100 | 1570 | 116000 | 4020 | 95100 |
| | 48 | 48 | 75400 | 675 | 73900 | 126 | 74700 |

TABLE 8-continued

Concentrations of bispecific antibodies (BsAb) reactive to IL-4 and IL-13 in monkey sera following repeated intravenous 5 minutes infusions of 2.5 mg/kg of huTBTI3_2_1 (batch #LP08059) in PBS. For each time point, values are mean concentrations out of three independent measurements done in triplicates.

| Dosing | Theoretical sampling time (h) from 1st dose | Theoretical sampling time (h) from last dose | Concentrations of functional huTBTI3_2_1 [ng/mL] | | | | |
|---|---|---|---|---|---|---|---|
| | | | Monkey #1 | SD | Monkey #2 | SD | mean |
| | 72 | 72 | 52800 | 57 | 48600 | 776 | 50700 |
| | 96 | 96 | 48900 | 1300 | 59500 | 2120 | 54200 |
| | 120 | 120 | 71600 | 2180 | 63800 | 802 | 67700 |
| | 144 | 144 | 76800 | 2510 | 77700 | 725 | 77300 |
| | 168 | 168 | 45700 | 883 | 44800 | 9690 | 45300 |
| | 240 | 240 | 34400 | 183 | 25700 | 892 | 30100 |
| dose 2 | 336 | 0 | 34500 | 3700 | 42000 | 11000 | 38300 |
| | 336.5 | 0.5 | 143000 | 7860 | 175000 | 26500 | 159000 |
| | 338 | 2 | 143000 | 4610 | 172000 | 31200 | 158000 |
| | 360 | 24 | 115000 | 14900 | 112000 | 19500 | 114000 |
| dose 3 | 504 | 0 | 84600 | 26400 | 55500 | 10100 | 70100 |
| | 504.5 | 0.5 | 176000 | 7540 | 158000 | 67600 | 167000 |
| | 506 | 2 | 205000 | 24300 | 208000 | 66500 | 207000 |
| | 528 | 24 | 145000 | 18700 | 112000 | 20700 | 129000 |
| dose 4 | 672 | 0 | 93900 | 9830 | 69700 | 14200 | 81800 |
| | 672.5 | 0.5 | 151000 | 645 | 17900 | 44900 | 84500 |
| | 674 | 2 | 187000 | 3340 | 219000 | 46500 | 203000 |
| | 696 | 24 | 161000 | 9680 | 156000 | 6660 | 159000 |
| dose 5 | 840 | 0 | 118000 | 5840 | 94200 | 3860 | 106100 |
| | 840.5 | 0.5 | 196000 | 8620 | 218000 | 25300 | 207000 |
| | 842 | 2 | 211000 | 6900 | 195000 | 23200 | 203000 |
| | 844 | 4 | 184000 | 6100 | 161000 | 17100 | 173000 |
| | 848 | 8 | 159000 | 12000 | 182000 | 13200 | 171000 |
| | 864 | 24 | 218000 | 31900 | 194000 | 18800 | 206000 |
| | 888 | 48 | 128000 | 9180 | 118000 | 13900 | 123000 |
| | 912 | 72 | 149000 | 1910 | 156000 | n.c. | 153000 |
| | 936 | 96 | 157000 | 53400 | 145000 | n.c. | 151000 |
| | 960 | 120 | 93300 | 6350 | 172000 | 27300 | 133000 |
| | 984 | 144 | 117000 | 1660 | 98600 | 1570 | 108000 |
| | 1,008 | 168 | 137000 | 6860 | 116000 | 20300 | 127000 |
| | 1,080 | 240 | 114000 | 1410 | 98000 | 11800 | 106000 |
| | 1176 | 336 | 85100 | 11400 | 64400 | 13300 | 74800 |
| | 1344 | 504 | 77700 | 12300 | 48800 | 10100 | 63300 |
| | 1512 | 672 | 47600 | 978 | 37100 | 8250 | 42400 |
| | 1680 | 840 | 36400 | 1600 | 22800 | 3130 | 29600 |
| | 1848 | 1008 | 21900 | 9550 | 15400 | 3460 | 18700 | n.c. not calculated;
LLOQ = 5 ng/mL

TABLE 9

Pharmacokinetic parameters of huTBTI3_2_1 after repeated intravenous 5 minutes infusions of 2.5 mg/kg of huTBTI3_2_1 (Batch #LP08059) in PBS in monkeys. Parameters were obtained after analysis of the functional BsAb concentration values with WinNonLin 5.2, non-compartment model 202.

| Intravenous administration (2.5 mg/kg) - 1st dose | | | |
|---|---|---|---|
| Subject | $C_{max}$ (ng/mL) | $AUC_{(0-336\,h)}$ (ng · h/mL) | $t_{last}$ (h) |
| Monkey #1 | 104000 | 17000000 | 336 |
| Monkey #2 | 152000 | 18000000 | 336 |
| Average | 128000 | 18000000 | 336 |

| Intravenous administration (2.5 mg/kg) - 5$^{th}$ dose | | | | | | | |
|---|---|---|---|---|---|---|---|
| Subject | $C_{max}$ (ng/mL) | $AUC_{(0-1008\,h)}$ (ng · h/mL) | $t_{last}$ (h) | $AUC_{(0-inf)}$ (ng · h/mL) | $AUC_{(0-336\,h)}$ (ng · h/mL) | $T_{1/2}$ (h) | Cl (L/h/kg) | $Vd_{ss}$ (L/kg) |
| Monkey #1 | 220000 | 79000000 | 1008 | 90000000 | 43000000 | 360 | 0.000028 | 0.014 |
| Monkey #2 | 220000 | 65000000 | 1008 | 72000000 | 40000000 | 290 | 0.000035 | 0.014 |
| Average | 220000 | 72000000 | 1008 | 81000000 | 42000000 | 330 | 0.000032 | 0.014 |

Accumulation ratio (=$AUC_{(0-336\,h)}$ dose 5/$AUC_{(0-336\,h)}$ dose 1) = 2.3

TABLE 10

Anti-drug antibody response to huTBTI3_2_1 after repeated intravenous 5 minutes infusions of 2.5 mg/kg of huTBTI3_2_1 (Batch #LP08059) in PBS in monkeys.

| Dosing | Theoretical sampling time (h) from 1st dose | Theoretical sampling time (h) from last dose | MSD signal from serum samples 1:10 (arbitrary unit) | | | | |
|---|---|---|---|---|---|---|---|
| | | | Monkey #1 | SD | Monkey #2 | SD | mean |
| dose 1 | 0 | 0 | 769 | 71 | 714 | 71 | 742 |
| | 0.5 | 0.5 | 565 | 68 | 468 | 50 | 516 |
| | 2 | 2 | 559 | 42 | 547 | 14 | 553 |
| | 4 | 4 | 511 | 39 | 531 | 51 | 521 |
| | 8 | 8 | 477 | 55 | 506 | 45 | 492 |
| | 24 | 24 | 509 | 17 | 497 | 73 | 503 |
| | 48 | 48 | 533 | 93 | 479 | 56 | 506 |
| | 72 | 72 | 689 | 60 | 644 | 55 | 667 |
| | 96 | 96 | 2000 | 110 | 1110 | 24 | 1560 |
| | 120 | 120 | 4320 | 77 | 1030 | 103 | 2680 |
| | 144 | 144 | 5550 | 677 | 810 | 114 | 3180 |
| | 168 | 168 | 3030 | 179 | 663 | 86 | 1850 |
| | 240 | 240 | 1720 | 15 | 571 | 25 | 1150 |
| dose 2 | 336 | 0 | 1270 | 61 | 610 | 15 | 940 |
| | 336.5 | 0.5 | 925 | 90 | 595 | 20 | 760 |
| | 338 | 2 | 1000 | 35 | 604 | 78 | 802 |
| | 360 | 24 | 751 | 17 | 716 | 109 | 734 |
| dose 3 | 504 | 0 | 965 | 53 | 945 | 27 | 955 |
| | 504.5 | 0.5 | 668 | 90 | 716 | 5 | 692 |
| | 506 | 2 | 597 | 63 | 585 | 52 | 591 |
| | 528 | 24 | 500 | 48 | 562 | 54 | 531 |
| dose 4 | 672 | 0 | 646 | 52 | 646 | 26 | 646 |
| | 672.5 | 0.5 | 493 | 33 | 593 | 67 | 543 |
| | 674 | 2 | 573 | 60 | 631 | 28 | 602 |
| | 696 | 24 | 644 | 49 | 508 | 70 | 576 |
| dose 5 | 840 | 0 | 672 | 48 | 452 | 23 | 562 |
| | 840.5 | 0.5 | 563 | 39 | 449 | 45 | 506 |
| | 842 | 2 | 530 | 22 | 463 | 20 | 497 |
| | 844 | 4 | 502 | 61 | 449 | 56 | 476 |
| | 848 | 8 | 525 | 61 | 388 | 16 | 456 |
| | 864 | 24 | 505 | 59 | 440 | 46 | 472 |
| | 888 | 48 | 706 | 126 | 564 | 54 | 635 |
| | 912 | 72 | 616 | 59 | 396 | 50 | 506 |
| | 936 | 96 | 618 | 71 | 467 | 44 | 542 |
| | 960 | 120 | 743 | 113 | 393 | 71 | 568 |
| | 984 | 144 | 616 | 68 | 402 | 56 | 509 |
| | 1008 | 168 | 467 | 28 | 402 | 48 | 435 |
| | 1080 | 240 | 487 | 9 | 430 | 26 | 459 |
| | 1176 | 336 | 503 | 25 | 421 | 12 | 462 |
| | 1344 | 504 | 570 | 69 | 403 | 39 | 487 |
| | 1512 | 672 | 667 | 47 | 412 | 10 | 540 |
| | 1680 | 840 | 583 | 33 | 431 | 21 | 507 |
| | 1848 | 1008 | 541 | 109 | 400 | 53 | 470 |

Figure 10:
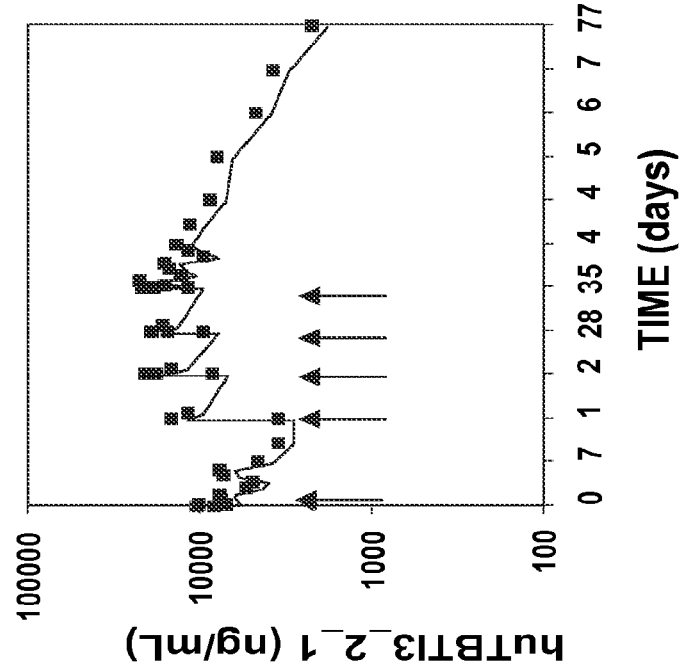
FIG. 10 shows a time plot (panel A) representation of the mean serum concentration of functional huTBTI3_2_1 after single dose intravenous perfusion administration of 2.5 mg/kg of huTBTI3_2_1 (Batch #LP08045) in PBS to a Cynomolgus Monkey at day 0, 14, 21 28 and 35; the table (panel B) summarizes pharmacokinetic parameters after the $1^{st}$ dose and the $5^{th}$ dose of 2.5 mg/kg of huTBTI3_2_1 (Batch #LP08059) in PBS in monkeys.

The serum exposure of the bispecific antibody huTBTI3_2_1 to IL-13/IL-4 was measured in male cynomolgus monkeys to establish repeat dose pharmacokinetic parameters.

huTBTI3_2_1, at a dose of 2.5 mg/kg, was given repeatedly to cynomolgus monkeys via intravenous infusions in a serial sampling paradigm. The antibody shows accumulation from the $1^{st}$ to the $5^{th}$ dose. $C_{max}$ and partial $AUC_{0-336h}$ increase from 128,000 ng/mL to 220,000 ng/mL and 18,000,000 ng·h/mL to 42,000,000 ng·h/mL respectively. After the $5^{th}$ dose there is good exposure to the antibody with $AUC_{0-inf}$ of 81,000,000 ng·h/mL (see FIG. 10). The antibody shows a serum clearance of 0.000032 L/hr-kg and a volume of distribution of 0.014 L/kg. The terminal elimination half-life is found to be 330 hours.

One monkey of the study shows a transient anti-drug antibody (ADA) response, which peaks on days 5-7. ADA level is back to background level by the day of the second infusion. There is no significant rise of ADA levels thereafter. The other monkey displays no significant levels of ADA at anytime.

No particular clinical sign or weight loss was observed during or after administration.

Example 9

Study Design Summary for a Randomized, Double-Blind, Placebo-Controlled Study of the Safety, Tolerability, and Pharmacokinetics of Ascending Single Subcutaneous Doses of huTBTI3_2_1 in Healthy Young Male Subjects This is the first investigation of huTBTI3_2_1 in humans and involves careful dose escalation in healthy subjects to obtain initial information on the safety, tolerability, and pharmacokinetic (PK) of single subcutaneous (SC) doses. Dose escalation was conducted in cohorts of healthy young male subjects (18 to 45 years of age, body weight between 50.0 and 95 kg, body mass index between 18.0 and 30.0 kg/m$^2$; certified as healthy by a comprehensive clinical assessment; normal heart rate and blood pressure after 10 minutes resting in supine position: 95 mmHg<systolic blood pressure<140 mmHg; 45 mmHg<diastolic blood pressure<90 mmHg; 40 bpm<heart rate<100 bpm; Normal standard 12-lead ECG after 10 minutes resting in supine position; 120 ms<PR<220 ms; QRS<120 ms; QTc≤430 ms; laboratory paramaters within normal range; C-reactive protein should not exceed 3 mg/L (using a high-sensitivity method of measurement); cardiac troponin I must not exceed the upper laboratory norm.)

This was a single-center, randomized, double-blind, placebo-controlled, ascending single SC dose study in four sequential cohorts of healthy young male subjects. Each dose cohort/group was designed to consist of 8 subjects (6 receiving huTBTI3_2_1 and 2 receiving placebo). This stepwise, dose escalation design was typical for introduction of a new therapeutic entity into humans.

The observation period of 85 days (~12 weeks) after dosing for treatment-emergent adverse events (TEAEs) and PK analysis was appropriate taking into account a typical elimination half-life for a monoclonal antibody of about 15 days. If ADA or autoimmunity antibodies (rheumatoid factor [RF], antinuclear antibodies [ANA], or anti-neutrophil cytoplasmic antibodies [ANCA]) measured at 12 weeks after dosing were increased from baseline, then an additional follow-up visit would occur at 6 months after dosing to document resolution or longer-term persistence. If, at the end of dose escalation in four sequential dose cohorts, additional information was needed at doses below the highest administered dose, then a fifth dose cohort of 8 subjects will be dosed and evaluated.

Given the immunomodulatory mechanism of action of huTBTI3_2_1, several specific laboratory tests related to inflammation were implemented.

C-Reactive Protein (CRP):

Inflammation is associated with elevations in acute phase proteins such as CRP. Using high sensitivity methodology, the upper limit of normal (ULN) for high sensitivity C-reactive protein (hsCRP) is now often stated to be 3 mg/L for the purpose of assessing cardiovascular risk; however, about a third of healthy subjects in the United States have CRP values between 3 and 10 mg/L, with occasional spurious elevations between 10 and 15 mg/L (Kushner I., et al. Am J Med 2006; 119(2):166.e17-28; Ridker, P M, et al., Circulation 2003:107(3):391-7; Pearson T A, et al, Circulation 2003:107(3):499-511; Ridker P M et al, 2000:342(12):836-43; Unek, I T et al., Clin Med Res. 2010; 8(2)89-95). Using serial sampling from healthy subjects, the critical difference for sequential values significant at P<0.05 (ie, the smallest percentage change unlikely to be due to analytical variability or normal within-subject variability) has been reported to be 118% (Macy E M et al, Clin Chem 1997:43(1):52-8). C-reactive protein values are typically considered clinically significant at levels above 10 mg/L, and sustained elevations above this level may be cause for concern. During acute inflammatory responses, values exceeding 100 mg/L can be observed (Clin B and Olshaker J S, J. Ennerg Med. 1999: 17(6)1019-25). Elevation in CRP has been consistently reported for conditions of active vasculitis (Konttinen Y T et al, Ind J Rheumatol 2007:2(3):100-4Hesselink D A et al., Scand J Rheumatol 2003:32(3)151-5). For this protocol, hsCRP was used, along with clinical observations, as the primary instrument for detection of drug-related inflammation and possible vasculitis. A sustained elevation in hsCRP above 10 mg/L for at least 72 hours, was viewed as possible early evidence of vasculitis. In general, drug-induced vasculitis is reversible upon discontinuation of treatment, and markers of inflammation such as hsCRP should return to normal or baseline values (Wiik, A, Curr Opin Rheumatol 2008:20(1)35-9; Calabrese L H and Duna G F, Curr Opin Rheumatol 1996; 8(1)34-40). In addition, consecutive elevations above 20 mg/L after drug administration can be viewed as evidence of a possible drug-related pro-inflammatory stimulus and, after excluding other causes of inflammation such as acute infections, possible reason for cessation of further dosing.

Cardiac Troponin I:

Serum cardiac troponin I (cTnI) was monitored to detect myocardial injury caused by potential coronary vasculitis (Kim M and Kim K, Pediatr Cardiol, 1999:20(3): 184-8). Interpretation of cTnI in the study was made in the context of clinical signs, symptoms, ECG and hsCRP, as cTnI elevations may be caused by factors other than myocardial injury (including strenuous exercise) (Wu A H, et al. Clin Chem. 2007; 53(12):2086-96).

Supplementary Tests for Vasculitis:

To further characterize inflammation associated with sustained elevations in hsCRP in individual subjects, additional laboratory tests related to vasculitis were performed, including tests for complement (C3, C4, and $CH_{50}$), cryoglobulin, ANCA (immunofluorescence for perinuclear and cytoplasmic ANCA and confirmatory immunoassays for anti-protease 3 [PR3] and anti-myeloperoxidase), RF, and ANA. Baseline values were established prior to dosing for all subjects; further assay of these supplementary tests for vasculitis were done for individual subjects who showed sustained elevation in hsCRP (>10 mg/L for at least 72 hours), in which case the supplementary tests were performed immediately (as soon as practicable) and at several subsequent visits.

The proposed array of supplementary tests provided insight into the mechanism of vasculitis, should it occur. ANCA is a new classification criteria (Sunderkötter C and Sindrilaru A. Eur J Dermatol. 2006; 16(2):114-24; Watts R et al., Ann Rheum Dis. 2007; 66(2):222-7; Watts R A et al., Rheumatology (Oxford). 2010 Jul. 20: 1-3). ANCA are classified according to the indirect immunofluorescence (IIF) patterns they produce on normal neutrophils and according to their target antigens (Pollock W et al. J Immunol Methods. 2009; 347(1-2):19-23; De Rosa F G and Agnello V. J Rheumatol. 2009; 36(9):1953-5; Clin Sci (Lond). 2005; 108(2):101-12) If myeloperoxidase-ANCA is positive, Churg-Strauss syndrome or microscopic polyarteritis can be suspected. If PR3-ANCA is positive Wegener's granulomatosis is most likely. If ANCA test is negative and cryoglobulin test is positive, cryoglobulinemic vasculitis should be suspected and its underlying diseases should be ruled out, particularly hepatitis C and B, systemic lupus erythematous (SLE), and Sjogren's syndrome. Serum C3 and C4 are often consumed in cryoglobulinemia, but are usually normal in polyarteritis nodosa as well as ANCA vasculitis. ANCA can be positive in the presence of other diseases including infection, inflammatory bowel disease and other connective tissue disease (eg, rheumatoid arthritis). In these cases, ANCA are positive but are negative for PR3 and myeloperoxidase.

Vascular Endothelial Activation Biomarkers:

The development of vasculitic lesions is associated with activation of endothelial cells and neutrophils (Tesfamariam B and DeFelice A F. Vascul Pharmacol. 2007; 46(4):229-37; Toxicol Appl Pharmacol. 2005; 207(2 Suppl):441-5). Enhanced expression of adhesion molecules such as e-selectin promotes interaction of the endothelium with circulating inflammatory cells. Various endothelial activation markers such as endothelin-1 and thrombomodulin are reportedly elevated during vasculitis. Vascular endothelial growth factor (VEGF) can alter vascular permeability and is elevated in serum from patients with Behçet's disease, microscopic polyangiitis, polyarteritis nodosa, giant cell arteritis, and systemic vasculitis (Cekmen M et al., Int J Dermatol. 2003; 42(11):870-5). If treatment-emergent inflammation (eg, sustained hsCRP elevations) or changes in laboratory values consistent with vasculitis was noted in multiple subjects, then archival serum and plasma samples (collected before and periodically after drug administration) was assayed for various exploratory biomarkers associated with vascular endothelial activation to further characterize the nature of the inflammation.

Lymphocyte Subsets:

To assure that specific subtypes of human lymphocytes are not selectively affected by huTBTI3_2_1, lymphocyte subsets were assessed using flow cytometry. This will include total T cells, T helper cells (CD4), T suppressor cells (CD8), and total B cells (CD19) expressed as absolute numbers and as a percent of total lymphocytes, as well as the CD4/CD8 ratio.

Immunogenicity

Systemic administration of monoclonal antibodies is associated with generation of ADA which can alter the PK and/or activity of the therapeutic antibodies (Hansel T T et al. Nat Rev Drug Discov. 2010; 9(4):325-38). Immunogenicity was assessed using an enzyme-linked immunosorbent assay (ELISA) for anti-huTBTI3_2_1 antibodies; a functional assay for assessment of antibody neutralization of huTBTI3_2_1 may be employed during future studies.

Urinary Albumin:

Appearance of protein in the urine is an indication of increased permeability of the renal glomeruli and, during clinical drug trials, evidence of possible renal injury. A standard urine dipstick assay for protein is typically used for this purpose. However, dipstick methodology may not detect the more subtle changes in glomerular function as might occur during early stages of vasculitis. Therefore, a more sensitive assay for urinary albumin was used during initial clinical studies of huTBTI3_2_1. An early morning spot urine collection was used to monitor potential appearance of microalbuminuria and reported as the albumin/creatinine ratio to correct for fluctuations in the extent of urine solute dilution. Post-treatment appearance of microalbuminuria was defined as observation of an albumin/creatinine ratio>30 µg/mg in 2 of 3 consecutive urine collections, as recommended for the monitoring of patients with diabetes mellitus (American Diabetes Association. Standards of medical care in diabetes—2009. Diabetes Care. 2009; 32 Suppl 1:S13-61). Since exercise can transiently elevate urinary albumin, vigorous physical exercise must be restricted prior to urine collection (Heathcote K L et al., Clin Invest Med. 2009; 32(4):E261-5). Urinary albumin results obtained within 24 hours of vigorous physical exercise must be excluded from consideration for purposes of defining microalbuminuria. An observation of an albumin/creatinine ratio>300 µg/mg in 2 of 3 consecutive urine collections was assessed as evidence of macroalbuminuria (American Diabetes Association. Standards of medical care in diabetes—2009. Diabetes Care. 2009; 32 Suppl 1:S13-61).

Tolerability at the Site of Investigational Product (IP) Injection:

The degree of discomfort and tissue reaction at the site of IP injection was monitored for up to 2 weeks after dosing, including standard qualitative and quantitative assessments for present pain (verbal scale) (Melzack R. The McGill Pain Questionnaire: major properties and scoring methods. Pain 1975; 1:277-299) and for erythema and swelling/induration/edema (Guidance for industry: toxicity grading scale for healthy adult and adolescent volunteers enrolled in preventive vaccine clinical trials, US Dept of Health and Human Services, Food and Drug Administration, Center for Biologics Evaluation and Research, September 2007).

The dose escalation steps for TDU11325 are provided in Table 11. The dose escalation ratio is 2-fold at each escalation step. This serial increase in dose is typical for initial clinical trials of therapeutic monoclonal antibodies and is supported by careful monitoring of potential safety signals.

TABLE 11

Sequential subcutaneous doses of huTBTI3_2_1

| Dose cohorts | Total volume injected subcutaneously | Dose in mg/kg assuming body weight of 60 kg | Incremental increase |
|---|---|---|---|
| 10 mg | 0.1 mL | 0.17 mg/kg | |
| 20 mg | 0.2 mL | 0.33 mg/kg | 2 |
| 40 mg | 0.4 mL | 0.67 mg/kg | 2 |
| 80 mg | 0.8 mL | 1.33 mg/kg | 2 |
| 150 mg | 1.5 ml | 2.50 mg/kg | 1.9 |
| 300 mg | 3.0 ml | 5.0 mg/kg | 2 |

Higher doses of huTBTI3_2_1 could be tested depending on the results of the lower doses. Higher doses could include any dose lower than, equal to or higher than a 300 mg cohort. Additional dose cohorts contemplated include but are not limited to 175 mg, 200 mg, 225 mg, 250 mg, 275 mg and 300 mg. Additional dose cohorts could also be 300 mg, 350 mg, 400 mg or higher.

huTBTI3_2_1 or placebo was administered as periumbilical SC injections in a fasted condition in a zone 4 to 10 cm to the right or left of the umbilicus and above the waistline. The dose cohorts in TDU11325 were obligatorily initiated as smaller subgroups as a safety precaution. For each dose cohort, 2 subjects were dosed on the first day. The remaining subjects in the cohort were dosed no sooner than 2 days (~48 hours) later, with no more than 2 subjects dosed each day.

A decision to proceed from dose "n" to the next higher "n+1" dose was made jointly by the Sponsor and the Investigator based on a preliminary safety report provided by the Investigator which includes blinded safety data for at least 21 days postdose (Day 22) of at least 6 out of 8 subjects of dose level cohort "n". Thus, taking into account the staggered dosing within a cohort, a new dose cohort was initiated about every 4 weeks. The relevant data for this decision should be at least: adverse events, hematology, lymphocyte subsets, coagulation, urinalysis, serum biochemistry (including hsCRP and cTnI), ECG, blood pressure, heart rate, and body temperature. The available PK data was also reviewed during the study progression.

In addition to the classic assessment of serious adverse events and the occurrence/severity of other adverse events by the Sponsor and the Investigator, after exploring potential confounding factors, the following criteria were considered as guidance for the decision to stop dosing:

More than 1 adverse event (same verbatim) of severe intensity for which the relationship to treatment cannot be reasonably excluded. The definition of "severe" intensity for an adverse event is that it prevents daily activities and requires symptomatic treatment;

QTc≥500 ms;

hsCRP>20 mg/L sustained for 2 consecutive blood collections 24 hours apart

Note: If hsCRP is >20 mg/L at a scheduled collection timepoint, an additional blood sample should be collected 24 hours later (or as soon as possible thereafter) for retesting.

huTBTI3_2_1 in lyophilized form for preparation of SC dose solution with each vial containing 185 mg of huTBTI3_2_1 plus excipients and stored between 2° C. and 8° C. (36° F. and 46° F.). To be reconstituted on the morning of dosing (no more than 1 hour prior to SC injection) with 1.7 mL sterile, nonpyrogenic distilled water at room temperature. The concentrations of the constituents in solution after reconstitution for injection were: 100 mg/mL of huTBTI3_2_1 in 6.3 mmol/L monobasic sodium phosphate, 3.7 mmol/L tromethamine, 5% (weight/volume) sucrose, 3% (w/V) proline, and 0.2% (w/V) polysorbate 80 with a final pH of 7.0. For placebo, each vial will contain 2 mL of liquid consisting of the same excipients at the same concentrations as for the reconstituted huTBTI3_2_1 formulation.

TABLE 12

Planned huTBTI3_2_1 subcutaneous administration

| Group | Dose (mg) | Total volume injected |
|---|---|---|
| 1 | 10 | 0.1 mL |
| 2 | 20 | 0.2 mL |
| 3 | 40 | 0.4 mL |
| 4 | 80 | 0.8 mL |
| 5 | 150 | 1.5 mL |
| 6 | 300 | 3.0 mL (two 1.5 mL injections) |

A predose fasting period commenced at least 10 hours prior to dosing and continued for 2 hours after dosing.

The safety and tolerability investigations at baseline and during the study consisted of:

Physical examination (includes at least: heart and respiratory auscultation; peripheral arterial pulse in both arms and both legs; pupil, knee, Achilles, and plantar reflexes; peripheral lymph nodes and abdomen examination; inspection of skin, hands and feet);

Body weight (kg);

Posteroanterior chest x-ray (at screening only unless clinically indicated postdose)

Body temperature (either oral or tympanic but consistently the same method throughout the study for all subjects);

Heart rate and systolic and diastolic blood pressure measured after 10 minutes in supine resting position and after 3 minutes in standing position);

Laboratory tests (all blood samples collected in the morning under fasted conditions, ie, only water for at least 10 hours prior, unless otherwise specified):

Hematology: red blood cell count (RBC), hematocrit (Hct), hemoglobin (Hb), white blood cell count (WBC) with differential (neutrophils, eosinophils, basophils, monocytes and lymphocytes), platelets;

Coagulation: prothrombin time (PT), international normalized ratio (INR), fibrinogen, and activated partial thromboplastin time (aPTT);

Serum biochemistry:

Electrolytes: sodium, potassium, chloride, calcium;
Liver function: AST, ALT, alkaline phosphatase, gamma-glutamyl transferase (GGT), total and conjugated bilirubin;
Renal function: urea, creatinine;
Metabolism: glucose, albumin, total protein, total cholesterol, triglycerides;
Potential muscle toxicity: creatine kinase (CK);
Potential cardiac toxicity: cTnI;
Inflammation biomarker: high-sensitivity CRP (hsCRP);
Lymphocyte subsets:
Total T cells (CD3), T helper cells (CD4), T suppressor cells (CD8), and total B cells (CD19) by flow cytometry, expressed as absolute numbers and as percent of total lymphocytes, as well as the CD4/CD8 ratio.

Immunogenicity: anti-huTBTI3_2_1 antibodies;
Supplementary tests for vasculitis (at baseline and, then postdose only for subjects exhibiting hsCRP>10 mg/L for ≥72 hours):
Complement assays: C3, C4, $CH_{50}$;
Cryoglobulin;
Rheumatoid factor (RF);
Anti-nuclear autoantibodies (ANA): HEp2 IIF (titer and pattern);
Anti-neutrophil cytoplasmic autoantibodies (ANCA): immunofluorescence for perinuclear and cytoplasmic ANCA and confirmatory immunoassays for anti-protease 3 and anti-myeloperoxidase.

Serology tests: HBsAg, hepatitis B core antibody, anti-HCV antibodies, anti-HIV1 and anti-HIV2 antibodies;
Archival blood samples: Serum and plasma samples were prepared and stored for future assay of laboratory parameters needed to support safety assessment. In particular, an observation of sustained inflammation (eg, hsCRP>10 mg/L for at least 72 hours) or appearance of treatment-emergent markers of vasculitis in multiple subjects may lead to assay of exploratory biomarkers of vascular endothelial activation.

For serum, a 10 mL blood sample was collected into a dry, red topped tube and, within 15 minutes of collection, centrifuged at approximately 1500 g for 10 minutes at 4° C.; the serum was then be transferred in roughly equal aliquots (using a plastic transfer pipet) into 3 storage tubes, which was immediately capped and frozen in an upright position at −20° C. or colder;

For plasma, a 10 mL ethylenediaminetetra-acetic acid (EDTA) blood sample was collected into a purple-top tube and, within 15 minutes of collection, centrifuged at approximately 1500 g for 10 minutes at 4° C.; the plasma was then be transferred in roughly equal aliquots (using a plastic transfer pipet) into 3 storage tubes, which was immediately capped and frozen in an upright position at −20° C. or colder;

Urinalysis:

A midstream urine specimen was collected and subjected to the following analyses.

A reagent strip dipstick analysis for detection of protein, glucose, blood (heme), leucocytes, ketone bodies, and pH. A positive glucose result should be confirmed with an alternative methodology for glucose according to the local clinical laboratory standard operating procedures. Upon initial detection of protein, glucose, or blood in a subject's urine, an additional urine specimen should be collected and subjected to urinalysis for confirmation.

The urine sediment should be examined for, at a minimum, the following formed elements: red blood cells, dysmorphic red blood cells, white blood cells, renal epithelial cells, casts (hyaline, RBC, WBC, granular, waxy, fatty, renal cell), bacteria, yeast and trichomonas. Abundance of each of these elements should be scored using standard laboratory terminology and units in use at the local laboratory (eg, number of cells per high power field, few, abundant). Any additional unusual observations should be noted on reports.

Urine microalbumin: quantitative assay of albumin and creatinine and calculation of albumin/creatinine ratio (µg/mg).

Urine drug screen: amphetamines/methamphetamines, barbiturates, benzodiazepines, cannabinoids, cocaine, opiates;

Alcohol breath or blood test;
Adverse events, spontaneously reported by the subject or observed by the Investigator, were monitored for definition of adverse events and related responses);
Standard 12-lead ECGs.
When vital signs, ECG, and blood samples were scheduled at the same time as an Investigational product administration and/or a meal, they were done prior to IP intake and/or meal. Whenever measurements of vital signs, ECG, and blood sampling for PK or safety coincided, the following order was respected: ECG, vital signs, PK samples, and safety samples.

Twelve-lead ECGs were recorded after at least 10 minutes in supine position using an electrocardiographic device. The electrodes were positioned at the same place for each ECG recording throughout the study (attachment sites of the leads will be marked with an indelible pen).

Each ECG consisted of a 10 second recording of the 12 leads simultaneously, leading to:

One single 12-lead ECG (25 mm/s, 10 mm/mV) printout with heart rate, PR, QRS, QT, QTc automatic correction evaluation, including date, time, initials and number of the subject, signature of the research physician, and at least 3 complexes for each lead. The Investigator medical opinion and automatic values were recorded in the eCRF. This printout was retained at the site level. As an exception, recordings were obtained in triplicate on Day 1 pre-dose.

The skin around the periumbilical area was examined for potential reactions to the SC injection. The maximum diameter of erythema and swelling (including induration and/or edema) was measured separately in millimeters and recorded. Erythema and swelling was graded separately as follows in a manner similar to the FDA guidance on assessment of vaccines. If there is no treatment-emergent change in a parameter at the time of observation, a value of 0 was recorded.

TABLE 13

Toxicity grading scale for local tolerability

|  | Mild | Moderate | Severe | Potentially Life Threatening |
|---|---|---|---|---|
| Erythema/ Redness | 2.5-5.0 cm | 5.1-10.0 cm | >10.0 cm | Necrosis or exfoliative dermatitis |
| Swelling/ Induration/ Edema | 2.5-5.0 cm and does not interfere with activity | 5.1-10.0 cm or interferes with activity | >10.0 cm or prevents daily activity | Necrosis |

In addition, the degree of itching and appearance of papules, pustules, and vesiculation was each scored using the following grading scale:

0=None; 1=Hardly perceptible; 2=Mild; 3=Moderate; 4=Severe

Skin reactions of moderate intensity or worse were reported as adverse events. The presence or the absence of the following symptoms or superficial observations were recorded without grading: erosion, dryness, scaling, cracking, scabbing, and glazing.

In addition, the present pain intensity was recorded using the following verbal numeric rating scale (self assessment by the study subject) based on a subset of the McGill Pain Questionnaire. A subject-assessed pain score of will be reported as an adverse event.

0=No Pain; 1=Mild; 2=Discomforting; 3=Distressing; 4=Horrible; 5=Excruciating

Pharmacokinetics

All blood collections for huTBTI3_2_1 PK analysis were scheduled to occur within ±15% of the sampling times. The number of plasma samples by subject and the total number of samples for the study are given in Table 14.

TABLE 14

TDU part - number of plasma samples collected for huTBTI3_2_1 assays

| Total by subject | 17 |
|---|---|
| Total for study (32 subjects)[a] | 544 |

[a]Four (4) dose groups of 8 subjects; not including optional 5th dose group

TABLE 15

Summary of sample handling procedures for huTBTI3_2_1 assays

| Blood Sample Volume | 4 mL |
|---|---|
| Anticoagulant | Sodium citrate |
| Plasma Aliquot Split | Yes |
| Plasma Storage Conditions | ≤−20° C. |
| Plasma Shipment Conditions | On dry ice |

An ELISA was used for the quantification of huTBTI3_2_1 in human plasma. Biotinylated IL-4 coated on a streptavidin plate is used to capture huTBTI3_2_1, which is then detected by SulfoTag-IL-13. This format, which uses electrochemiluminescence detection, is able to detect huTBTI3_2_1 that retains at least 1 unoccupied binding site for IL-4 and 1 unoccupied binding site for IL-13. Since huTBTI3_2_1 plasma concentrations were typically present in large molar excess compared to concentrations of IL-4 and IL-13, the assay reflected total concentrations of huTBTI3_2_1.

The potential interference of ADA with huTBTI3_2_1 measurements were taken into account when assaying clinical samples.

TABLE 16

Summary of bioanalytical method for huTBTI3_2_1

| Analyte | huTBTI3_2_1 |
|---|---|
| Matrix | Plasma |
| Analytical Technique | ELISA |
| Lower limit of Quantification | 50 ng/mL (to be confirmed at the end of validation) |
| Analyte | huTBTI3_2_1 |
| Assay volume | 100 µL |
| Site of Bioanalysis | Bertin Pharma (CRO) Saclay, France |
| Method Reference | DOH0850 (validation on going) |

ELISA = enzyme-linked immunosorbent assay

For the analysis of potential anti-huTBTI3_2_1 antibodies (ADA) in human plasma, a bridging qualitative ELISA using electrochemiluminescence detection was used. A cut-off that should provide a 5% false positive rate, above which a plasma sample was considered as potentially positive for anti-huTBTI3_2_1 antibody, was used in each screening assay.

Positive samples in screening assay were then tested in a confirmatory assay (competition with huTBTI3_2_1) in order to demonstrate the presence of antibodies and eliminate false positive results generated from the initial screening assay. Interference of huTBTI3_2_1 in the ADA assay was be documented so that the highest drug concentration that did not affect the limit of ADA detection was known and the interpretation of immunogenicity taken into account this parameter.

TABLE 17

Summary of bioanalytical method for anti-huTBTI3_2_1 antibodies

| Analyte | Anti-huTBTI3_2_1 antibodies |
|---|---|
| Matrix | Plasma |
| Analytical Technique | ELISA (screening and confirmatory assays) |
| Sensitivity | <100 ng/mL |
| Assay volume | 100 µL |
| Site of Bioanalysis | Montpellier, France |
| Method Reference | DOH0851 |

ELISA = enzyme-linked immunosorbent assay

Plasma concentrations were used to determine the PK parameters of huTBTI3_2_1 listed in Table 18 using standard non-compartmental techniques.

TABLE 18

List of pharmacokinetic parameters for plasma huTBTI3_2_1 and definitions

| Parameters | Definition/Calculation |
|---|---|
| $C_{max}$ | Maximum plasma concentration observed |
| $t_{max}$ | First time to reach $C_{max}$ |
| $AUC_{last}$ | Area under the plasma concentration versus time curve calculated using the trapezoidal method from time zero to the real time |
| AUC | Area under the plasma concentration versus time curve extrapolated to infinity according to the following equation: |

$$AUC = AUC_{last} + \frac{C_{last}}{\lambda_z}$$

TABLE 18-continued

List of pharmacokinetic parameters
for plasma huTBTI3_2_1 and definitions

| Parameters | Definition/Calculation |
|---|---|
| $t_{last}$ | Time corresponding to the last concentration above the limit of quantification, $C_{last}$ |
| $t_{1/2z}$ | Terminal half-life associated with the terminal slope ($\lambda z$) determined according to the following equation: $$t_{1/2Z} = \frac{0.693}{\lambda_z}$$ where $\lambda z$ is the slope of the regression line of the terminal phase of the plasma concentration versus time curve, in semi-logarithmic scale. Half-life is calculated by taking the regression of at least 3 points. |
| CL/F | Apparent total body clearance of a drug from the plasma calculated using the following equation: $$CL/F = \frac{Dose}{AUC}$$ |
| Vss/F | Apparent volume of distribution at steady state after non-intravenous administration Vss/F = CL/F * MRT |

TABLE 19

Sampled blood volume

| Type | Volume per sample | Number of samples | Total |
|---|---|---|---|
| Serology tests | 5 mL | 1 | 5 mL |
| Hematology | 3 mL | 13[a] | 39 mL |
| Serum biochemistry with hsCRP and cTnI | 10 mL | 13[a] | 130 mL |
| Coagulation (PT, INR, fibrinogen, and aPTT) | 3 mL | 13[a] | 39 mL |
| Lymphocyte subsets | 4 mL | 6 | 24 mL |
| Pharmacogenetic for stored DNA | 6 mL | 1 | 6 mL |
| Pharmacokinetic huTBTI3_2_1 | 4 mL | 17 | 68 mL |
| huTBTI3_2_1 immunogenicity (ADA) | 4 mL | 5 | 20 mL |
| Archival sample - serum | 10 mL | 5 | 50 mL |
| Archival sample - EDTA plasma | 10 mL | 5 | 50 mL |
| Supplementary vasculitis tests (frozen serum) | 10 mL | 6[b] | 60 mL |
| Cryoglobulin (room temperature serum) | 10 mL | 6[b] | 60 mL |
| TOTAL | | | 551 mL |

[a]Includes optional 6-month visit
[b]Includes 5 additional samples (beyond baseline on Day −1) to be collected only if elevations in hsCRP >10 mg/L for >72 hours are observed.
Abbreviations:
ADA = anti-drug antibodies;
aPTT = activated partial thromboplastin time;
cTnI = cardiac troponin I;
EDTA = ethylenediaminetetra-acetic acid;
hsCRP = high sensitivity C-reactive protein;
INR = international normalized ratio;
PT = prothrombin time For $C_{max}$, $AUC_{last}$, AUC, dose proportionality was assessed using the empirical power model (PK parameter=$\alpha \times dose^\beta$), along with an "estimation" interpretation, according to the recommendations of Gough et al Pharmacokinetics UK Joint Working Group Drug Infor J 1995;29:1039-1048.

The power model will be fit on the log-transformed scale:

log(parameter)=log($\alpha$)+$\beta \times$log(dose)+Error.

Model lack-of-fit was assessed by residual plots, and by an F-test of the residual mean square versus the pure error residual mean square. If the model fit is adequate, estimates with 90% confidence intervals for $\beta$ were obtained, and further used to obtain estimates and 90% confidence intervals for the PK parameter increase associated with an r-fold (r=2 and r=high dose/low dose) increase in dose, by exponentiating r to the powers of the $\beta$ estimate ("b") and confidence limits:

$$r^{b \pm t \times SE(b)}$$

If there is evidence of model lack-of-fit, then attempts were made to fit the model over a reduced dose range (eg, exclude 1 extreme dose level). Otherwise, a fixed effect model was used, with fixed term for dose, using logarithms of the relevant PK parameters. Estimates with 90% confidence intervals for the parameter increases associated with pairwise dose increases were obtained by first computing estimates with confidence intervals for differences between pairwise dose groups in the fixed effects model framework, and then converting to ratios using the antilog transformation.

For $t_{1/2z}$, dose effect will be assessed with a linear fixed effect model,

Log($t_{1/2z}$)=Dose+Error

Point estimate and 90% confidence interval for the geometric mean of $t_{1/2z}$ were provided pooled across dose levels and separately for each dose group.

The distribution of $t_{max}$ values was represented by histogram plots for each dose level.

Definition of Adverse Event and Serious Adverse Event

An adverse event is any untoward medical occurrence in a subject administered a pharmaceutical product and which does not necessarily have to have a causal relationship with this treatment.

A serious adverse event is any untoward medical occurrence that at any dose:
Results in death or
Is life-threatening, or
  Note: The term "life-threatening" in the definition of "serious" refers to an event in which the subject was at risk of death at the time of the event; it does not refer to an event which hypothetically might have caused death if it were more severe.
Requires inpatient hospitalization or prolongation of existing hospitalization, or
Results in persistent or significant disability/incapacity, or
Is a congenital anomaly/birth defect, or
Is a medically important event:
  Medical and scientific judgment should be exercised in deciding whether expedited reporting is appropriate in other situations, such as important medical events that may not be immediately life-threatening or result in death or hospitalization but may jeopardize the subject or may require intervention to prevent 1 of the other outcomes listed in the definition above.
  Note: As guidance for determining which conditions are medically important events, the following examples are provided, though not intended to be exhaustive:
intensive treatment in an emergency room or at home for allergic bronchospasm;
blood dyscrasias such as agranulocytosis, aplastic anemia, bone marrow aplasia, myelodysplasia, pancytopenia;
convulsions;
alanine aminotransferase (ALT)>3×upper limit of normal range (ULN) associated with total bilirubin>2×ULN;
asymptomatic ALT increase>10×ULN; or
development of drug dependency or drug abuse.

Adverse events requiring the Sponsor to be informed immediately:
ALT increase≥2×ULN
hsCRP>10 mg/L for ≥72 hours
cardiac troponin I (cTnI)>2×ULN
If cTnI>2×ULN is observed, cTnI, creatine kinase (CK) and myocardial B fraction of creatine kinase (CK-MB) values should be serially tracked (at a minimum in an immediate additional blood collection and on the following day), along with additional ECG recordings, until test results return to normal. Consultation of a cardiologist should be considered promptly if elevations in cTnI persist, the CK-MB/CK ratio is elevated, and/or treatment emergent abnormalities in ECG recordings are observed.
QTc≥500 ms
In occurrences of prolongation of QTc automatic measurement 500 ms, confirmed by a manual reading by the Investigator, or a physician delegated by the Investigator, using the Fridericia formula for correcting QT, the subject should be placed under supervision in a specialized setting. Appropriate blood samples will be collected (eg, for cTnI). Subsequent ECG monitoring of the subject should then be performed on a regular and clinically responsible basis until the QTc interval returns to a safe value as determined by the Investigator in agreement with the Sponsor.
Severe skin reactions local to the site of IP injection
Symptomatic overdose with IP
    An overdose (accidental or intentional) with the IP is an event suspected by the Investigator or spontaneously notified by the subject (not based on systematic IP vial count) and defined as at least twice of the intended dose.
Laboratory abnormalities include:
Neutropenia,
    Defined as neutrophil blood count<1500/mm$^3$ (but <1000/mm$^3$ in subjects of African descent)
Thrombocytopenia,
    Defined as platelet count<100 000/mm$^3$
Acute renal failure
    Rapid increase in serum creatinine over 150 μmol/L (1.7 mg/dL)
        Suspicion of rhabdomyolysis Example 10

Results from the Randomized, Double-Blind, Placebo-Controlled Study of the Safety, Tolerability, and Pharmacokinetics of Ascending Single Subcutaneous Doses of SAR1 56597 in Healthy Young Male Subjects (TDU11325)

The following Tables, Tables 20-35, summarize the data from TDU11325 study.

TABLE 20

| | Subject disposition | | | | | | |
|---|---|---|---|---|---|---|---|
| | | SAR156597 | | | | | |
| | Placebo | 10 mg | 20 mg | 40 mg | 80 mg | 150 mg | 300 mg |
| Randomized and treated | 12 | 6 | 6 | 6 | 6 | 6 | 6 |

PGM = PRODOPS/SAR156597/TDU11325/CSR/REPORT/PGM/dis_dsover_s_t.sas
OUT = REPORT/OUTPUT/dis_dsover_s_t_i.rtf (08MAR2012 - 15:31)

TABLE 21

| | Analysis population | | | | | | | |
|---|---|---|---|---|---|---|---|---|
| | | SAR156597 | | | | | | |
| | Placebo | 10 mg | 20 mg | 40 mg | 80 mg | 150 mg | 300 mg | All |
| Safety population | 12 | 6 | 6 | 6 | 6 | 6 | 6 | 48 |
| Pharmacokinetic population | 0 | 6 | 6 | 5 | 6 | 6 | 6 | 35 |
| Pharmacodynamic population | 12 | 6 | 6 | 6 | 6 | 6 | 6 | 48 |

PGM = PRODOPS/SAR156597/TDU11325/CSR/REPORT/PGM/dis_popover_a_t.sas
OUT = REPORT/OUTPUT/dis_popover_a_t_i.rtf (08MAR2012 - 15:31)

TABLE 22

| | Demographics and subject characteristics at baseline - safety population | | | | | | | |
|---|---|---|---|---|---|---|---|---|
| | | SAR156597 | | | | | | |
| | Placebo (N = 12) | 10 mg (N = 6) | 20 mg (N = 6) | 40 mg (N = 6) | 80 mg (N = 6) | 150 mg (N = 6) | 300 mg (N = 6) | All (N = 48) |
| Age (years) | | | | | | | | |
| Number | 12 | 6 | 6 | 6 | 6 | 6 | 6 | 48 |
| Mean (SD) | 31.7 (8.7) | 29.5 (5.7) | 29.0 (7.4) | 30.5 (7.3) | 33.0 (6.7) | 30.0 (7.8) | 29.3 (7.4) | 30.6 (7.2) |
| Median | 30.0 | 29.5 | 25.0 | 33.0 | 34.5 | 29.0 | 27.5 | 30.0 |
| Min:Max | 22:44 | 22:39 | 24:42 | 19:37 | 21:41 | 21:41 | 21:40 | 19:44 |
| Sex [n (%)] | | | | | | | | |
| Number | 12 | 6 | 6 | 6 | 6 | 6 | 6 | 48 |
| Male | 12 (100%) | 6 (100%) | 6 (100%) | 6 (100%) | 6 (100%) | 6 (100%) | 6 (100%) | 48 (100%) |
| Race [n (%)] | | | | | | | | |
| Number | 12 | 6 | 6 | 6 | 6 | 6 | 6 | 48 |
| Caucasian/White | 9 (75.0%) | 4 (66.7%) | 5 (83.3%) | 5 (83.3%) | 4 (66.7%) | 4 (66.7%) | 4 (66.7%) | 35 (72.9%) |

TABLE 22-continued

Demographics and subject characteristics at baseline - safety population

| | | SAR156597 | | | | | | |
|---|---|---|---|---|---|---|---|---|
| | Placebo (N = 12) | 10 mg (N = 6) | 20 mg (N = 6) | 40 mg (N = 6) | 80 mg (N = 6) | 150 mg (N = 6) | 300 mg (N = 6) | All (N = 48) |
| Black | 1 (8.3%) | 0 | 0 | 0 | 1 (16.7%) | 0 | 2 (33.3%) | 4 (8.3%) |
| Asian/Oriental | 1 (8.3%) | 0 | 0 | 0 | 1 (16.7%) | 0 | 0 | 2 (4.2%) |
| Other | 1 (8.3%) | 2 (33.3%) | 1 (16.7%) | 1 (16.7%) | 0 | 2 (33.3%) | 0 | 7 (14.6%) |
| Weight (kg) | | | | | | | | |
| Number | 12 | 6 | 6 | 6 | 6 | 6 | 6 | 48 |
| Mean (SD) | 76.23 (9.56) | 78.55 (10.50) | 71.67 (8.57) | 79.85 (8.95) | 79.30 (11.33) | 77.92 (8.39) | 80.32 (15.89) | 77.51 (10.22) |
| Median | 76.80 | 78.80 | 70.40 | 82.60 | 81.50 | 76.20 | 83.80 | 76.80 |
| Min:Max | 60.3:93.1 | 67.5:88.7 | 62.2:87.0 | 64.4:89.7 | 59.8:94.1 | 67.6:91.3 | 53.0:95.0 | 53.0:95.0 |

PGM = PRODOPS/SAR156597/TDU11325/CSR/REPORT/PGM/dem_dmsc_s_t.sas
OUT = REPORT/OUTPUT/dem_dmsc_s_t_i.rtf (08MAR2012 - 15:32)

TABLE 23

Overview of adverse event profile: treatment emergent adverse events - safety population

| | | SAR156597 | | | | | |
|---|---|---|---|---|---|---|---|
| n(%) | Placebo (N = 12) | 10 mg (N = 6) | 20 mg (N = 6) | 40 mg (N = 6) | 80 mg (N = 6) | 150 mg (N = 6) | 300 mg (N = 6) |
| Subjects with any TEAE | 11 (91.7%) | 3 (50.0%) | 4 (66.7%) | 4 (66.7%) | 4 (66.7%) | 5 (83.3%) | 3 (50.0%) |
| Subjects with any severe TEAE | 1 (8.3%) | 0 | 0 | 0 | 0 | 0 | 0 |
| Subjects with any treatment emergent SAE | 0 | 0 | 0 | 0 | 0 | 1 (16.7%) | 0 |
| Subjects with any TEAE leading to permanent treatment discontinuation | na | na | na | na | na | na | na |

EAE: Treatment emergent adverse event,
SAE: Serious adverse event
na = not applicable
N = Number of subjects treated within each group,
n (%) = number and % of subjects with at least one TEAE in each category
Note:
An adverse event is considered as treatment emergent if it occurred from the time of the first investigational product (IP) administration up to the end of study visit (included).
PGM = PRODOPS/SAR156597/TDU11325/CSR/REPORT/PGM/ae_aeover_s_t.sas
OUT = REPORT/OUTPUT/ae_aeover_s_t_i.rtf (08MAR2012 - 15:31)

TABLE 24

Number (%) of subjects with TEAE(s) by Primary SOC and PT - safety population

| | | SAR156597 | | | | | |
|---|---|---|---|---|---|---|---|
| Primary system organ class Preferred term [n (%)] | Placebo (N = 12) | 10 mg (N = 6) | 20 mg (N = 6) | 40 mg (N = 6) | 80 mg (N = 6) | 150 mg (N = 6) | 300 mg (N = 6) |
| Any class | 11 (91.7%) | 3 (50.0%) | 4 (66.7%) | 4 (66.7%) | 4 (66.7%) | 5 (83.3%) | 3 (50.0%) |
| Infections and infestations | 2 (16.7%) | 2 (33.3%) | 1 (16.7%) | 1 (16.7%) | 2 (33.3%) | 1 (16.7%) | 2 (33.3%) |
| Infectious mononucleosis | 0 | 0 | 0 | 0 | 0 | 0 | 1 (16.7%) |
| Upper respiratory tract infection | 2 (16.7%) | 1 (16.7%) | 0 | 1 (16.7%) | 0 | 0 | 1 (16.7%) |
| Bronchitis | 0 | 0 | 0 | 0 | 0 | 1 (16.7%) | 0 |
| Conjunctivitis infective | 0 | 0 | 0 | 0 | 1 (16.7%) | 0 | 0 |
| Gastroenteritis | 0 | 1 (16.7%) | 0 | 0 | 0 | 0 | 0 |
| Impetigo | 0 | 0 | 0 | 0 | 1 (16.7%) | 0 | 0 |
| Pharyngitis | 0 | 1 (16.7%) | 1 (16.7%) | 0 | 0 | 0 | 0 |
| Blood and lymphatic system disorders | 0 | 0 | 0 | 1 (16.7%) | 0 | 0 | 1 (16.7%) |
| Neutropenia | 0 | 0 | 0 | 0 | 0 | 0 | 1 (16.7%) |
| Eosinophilia | 0 | 0 | 0 | 1 (16.7%) | 0 | 0 | 0 |
| Metabolism and nutrition disorders | 0 | 0 | 1 (16.7%) | 0 | 0 | 0 | 0 |

TABLE 24-continued

Number (%) of subjects with TEAE(s) by Primary SOC and PT - safety population

| Primary system organ class<br>Preferred term [n (%)] | Placebo<br>(N = 12) | SAR156597 | | | | | |
|---|---|---|---|---|---|---|---|
| | | 10 mg<br>(N = 6) | 20 mg<br>(N = 6) | 40 mg<br>(N = 6) | 80 mg<br>(N = 6) | 150 mg<br>(N = 6) | 300 mg<br>(N = 6) |
| Decreased appetite | 0 | 0 | 1 (16.7%) | 0 | 0 | 0 | 0 |
| Nervous system disorders | 4 (33.3%) | 1 (16.7%) | 0 | 2 (33.3%) | 2 (33.3%) | 2 (33.3%) | 0 |
| Amnesia | 0 | 0 | 0 | 1 (16.7%) | 0 | 0 | 0 |
| Dizziness | 1 (8.3%) | 0 | 0 | 0 | 0 | 1 (16.7%) | 0 |
| Headache | 3 (25.0%) | 1 (16.7%) | 0 | 2 (33.3%) | 2 (33.3%) | 2 (33.3%) | 0 |
| Muscle contractions involuntary | 1 (8.3%) | 0 | 0 | 0 | 0 | 0 | 0 |
| Presyncope | 1 (8.3%) | 0 | 0 | 0 | 0 | 0 | 0 |
| Sinus headache | 0 | 0 | 0 | 1 (16.7%) | 0 | 0 | 0 |
| Cardiac disorders | 0 | 1 (16.7%) | 0 | 0 | 0 | 0 | 0 |
| Palpitations | 0 | 1 (16.7%) | 0 | 0 | 0 | 0 | 0 |
| Vascular disorders | 0 | 1 (16.7%) | 0 | 0 | 0 | 1 (16.7%) | 0 |
| Deep vein thrombosis | 0 | 0 | 0 | 0 | 0 | 1 (16.7%) | 0 |
| Orthostatic hypotension | 0 | 1 (16.7%) | 0 | 0 | 0 | 0 | 0 |
| Respiratory, thoracic and mediastinal disorders | 2 (16.7%) | 2 (33.3%) | 1 (16.7%) | 1 (16.7%) | 0 | 2 (33.3%) | 1 (16.7%) |
| Cough | 1 (8.3%) | 0 | 0 | 0 | 0 | 0 | 1 (16.7%) |
| Dyspnoea | 1 (8.3%) | 1 (16.7%) | 0 | 0 | 0 | 0 | 0 |
| Nasal congestion | 0 | 1 (16.7%) | 1 (16.7%) | 1 (16.7%) | 0 | 1 (16.7%) | 0 |
| Oropharyngeal pain | 0 | 0 | 0 | 0 | 0 | 1 (16.7%) | 0 |
| Pneumothorax | 0 | 0 | 0 | 0 | 0 | 1 (16.7%) | 0 |
| Gastrointestinal disorders | 3 (25.0%) | 0 | 0 | 0 | 2 (33.3%) | 3 (50.0%) | 1 (16.7%) |
| Constipation | 0 | 0 | 0 | 0 | 0 | 1 (16.7%) | 1 (16.7%) |
| Diarrhoea | 1 (8.3%) | 0 | 0 | 0 | 0 | 0 | 1 (16.7%) |
| Abdominal pain | 0 | 0 | 0 | 0 | 1 (16.7%) | 0 | 0 |
| Dyspepsia | 1 (8.3%) | 0 | 0 | 0 | 0 | 0 | 0 |
| Inguinal hernia | 1 (8.3%) | 0 | 0 | 0 | 0 | 0 | 0 |
| Nausea | 1 (8.3%) | 0 | 0 | 0 | 0 | 2 (33.3%) | 0 |
| Toothache | 0 | 0 | 0 | 0 | 1 (16.7%) | 0 | 0 |
| Vomiting | 0 | 0 | 0 | 0 | 0 | 1 (16.7%) | 0 |
| Skin and subcutaneous tissue disorders | 2 (16.7%) | 0 | 0 | 1 (16.7%) | 0 | 1 (16.7%) | 0 |
| Dermatitis contact | 2 (16.7%) | 0 | 0 | 1 (16.7%) | 0 | 1 (16.7%) | 0 |
| Papule | 0 | 0 | 0 | 0 | 0 | 1 (16.7%) | 0 |
| Musculoskeletal and connective tissue disorders | 2 (16.7%) | 0 | 2 (33.3%) | 1 (16.7%) | 1 (16.7%) | 0 | 1 (16.7%) |
| Back pain | 0 | 0 | 1 (16.7%) | 1 (16.7%) | 0 | 0 | 1 (16.7%) |
| Musculoskeletal stiffness | 0 | 0 | 0 | 0 | 0 | 0 | 1 (16.7%) |
| Myalgia | 1 (8.3%) | 0 | 1 (16.7%) | 0 | 1 (16.7%) | 0 | 0 |
| Myositis | 1 (8.3%) | 0 | 0 | 0 | 0 | 0 | 0 |
| Neck pain | 0 | 0 | 1 (16.7%) | 1 (16.7%) | 0 | 0 | 0 |
| Renal and urinary disorders | 0 | 0 | 1 (16.7%) | 0 | 0 | 0 | 0 |
| Haematuria | 0 | 0 | 1 (16.7%) | 0 | 0 | 0 | 0 |
| General disorders and administration site conditions | 2 (16.7%) | 1 (16.7%) | 1 (16.7%) | 0 | 1 (16.7%) | 0 | 0 |
| Fatigue | 1 (8.3%) | 0 | 0 | 0 | 1 (16.7%) | 0 | 0 |
| Influenza like illness | 1 (8.3%) | 0 | 0 | 0 | 0 | 0 | 0 |
| Injection site erythema | 1 (8.3%) | 0 | 0 | 0 | 0 | 0 | 0 |
| Pyrexia | 0 | 1 (16.7%) | 1 (16.7%) | 0 | 0 | 0 | 0 |
| Investigations | 2 (16.7%) | 0 | 1 (16.7%) | 0 | 0 | 0 | 2 (33.3%) |
| Aspartate aminotransferase increased | 0 | 0 | 0 | 0 | 0 | 0 | 1 (16.7%) |
| Blood creatine phosphokinase increased | 1 (8.3%) | 0 | 1 (16.7%) | 0 | 0 | 0 | 1 (16.7%) |
| C-reactive protein increased | 0 | 0 | 0 | 0 | 0 | 0 | 1 (16.7%) |
| Liver function test abnormal | 0 | 0 | 0 | 0 | 0 | 0 | 1 (16.7%) |
| Activated partial thromboplastin time prolonged | 1 (8.3%) | 0 | 0 | 0 | 0 | 0 | 0 |
| Transaminases increased | 1 (8.3%) | 0 | 0 | 0 | 0 | 0 | 0 |
| Injury, poisoning and procedural complications | 3 (25.0%) | 0 | 1 (16.7%) | 0 | 1 (16.7%) | 3 (50.0%) | 0 |
| Arthropod bite | 1 (8.3%) | 0 | 0 | 0 | 0 | 1 (16.7%) | 0 |
| Contusion | 0 | 0 | 1 (16.7%) | 0 | 1 (16.7%) | 0 | 0 |
| Excoriation | 1 (8.3%) | 0 | 1 (16.7%) | 0 | 0 | 2 (33.3%) | 0 |
| Laceration | 1 (8.3%) | 0 | 0 | 0 | 0 | 0 | 0 |
| Multiple fractures | 0 | 0 | 0 | 0 | 0 | 1 (16.7%) | 0 |

TABLE 24-continued

Number (%) of subjects with TEAE(s) by Primary SOC and PT - safety population

|  | Placebo (N = 12) | SAR156597 | | | | | |
|---|---|---|---|---|---|---|---|
| Primary system organ class Preferred term [n (%)] |  | 10 mg (N = 6) | 20 mg (N = 6) | 40 mg (N = 6) | 80 mg (N = 6) | 150 mg (N = 6) | 300 mg (N = 6) |
| Muscle strain | 0 | 0 | 0 | 0 | 0 | 1 (16.7%) | 0 |
| Road traffic accident | 0 | 0 | 1 (16.7%) | 0 | 0 | 1 (16.7%) | 0 |

TEAE: Treatment emergent adverse event,

SOC: Sytem organ class,

PT: Preferred term MedDRA 14.1

N = Number of subjects treated within each group, n (%) = number and % of subjects with at least one TEAE in each category Note:

Table sorted by SOC internationally agreed order and decreasing frequency of PT in SAR156597 300 mg group Note:

An adverse event is considered as treatment emergent if it occurred from the time of the first investigational product (IP) administration up to the end of study visit (included).

PGM = PRODOPS/SAR156597/TDU11325/CSR/REPORT/PGM/ae_iaeteae_s_t.sas

OUT = REPORT/OUTPUT/ae_iaeteae_s_t_i.rtf (08MAR2012 - 15:32)

TABLE 25

Hematology - Number of subjects with abnormalities (PCSA) during the TEAE period according to baseline status - safety population

|  | Placebo (N = 12) | | SAR156597 | | | | | | | | | | | |
|---|---|---|---|---|---|---|---|---|---|---|---|---|---|---|
|  |  |  | 10 mg (N = 6) | | 20 mg (N = 6) | | 40 mg (N = 6) | | 80 mg (N = 6) | | 150 mg (N = 6) | | 300 mg (N = 6) | |
| Laboratory parameter PCSA criteria n/N1 | Nor. bas. | Abn. bas. | Nor. bas. | Abn. bas. | Nor. bas. | Abn. bas. | Nor. bas. | Abn. bas. | Nor. bas. | Abn. bas. | Nor. bas. | Abn. bas. | Nor. bas. | Abn. bas. |
| Hemoglobin |  |  |  |  |  |  |  |  |  |  |  |  |  |  |
| Decr. from B ≥20 g/L | 1/12 | na | 1/6 | na | 0/6 | na | 0/6 | na | 0/6 | na | 1/6 | na | 0/6 | na |
| Platelet count (thrombocyte count) |  |  |  |  |  |  |  |  |  |  |  |  |  |  |
| <100 Giga/L | 0/12 | 0/0 | 0/6 | 0/0 | 0/6 | 0/0 | 0/6 | 0/0 | 0/6 | 0/0 | 0/6 | 0/0 | 0/6 | 0/0 |
| White blood cell count (leukocyte count) |  |  |  |  |  |  |  |  |  |  |  |  |  |  |
| <3.0 Giga/L (Non-Black); <2.0 Giga/L (Black) | 0/12 | 0/0 | 0/6 | 0/0 | 0/6 | 0/0 | 0/6 | 0/0 | 0/6 | 0/0 | 0/6 | 0/0 | 0/6 | 0/0 |
| Neutrophils |  |  |  |  |  |  |  |  |  |  |  |  |  |  |
| <1.5 Giga/L (Non-Black); <1.0 Giga/L (Black) | 0/12 | 0/0 | 0/6 | 0/0 | 0/6 | 0/0 | 0/6 | 0/0 | 0/6 | 0/0 | 0/6 | 0/0 | 1/6 | 0/0 |
| Eosinophils |  |  |  |  |  |  |  |  |  |  |  |  |  |  |
| >0.5 Giga/L or >ULN (if ULN ≥0.5 Giga/L) | 0/12 | 0/0 | 0/6 | 0/0 | 0/6 | 0/0 | 0/5 | 1/1 | 1/6 | 0/0 | 0/6 | 0/0 | 0/6 | 0/0 |

PCSA: Potentially Clinically Significant Abnormalities (Version of 14 Sep. 2009)

LLN/ULN = Lower/Upper Limit of Normal range,

B = Baseline,

Nor. bas. = Normal baseline,

Abn. bas. = Abnormal baseline (LLN/ULN or PCSA),

Miss. bas. = Missing baseline, na = not applicable n/N1 = number of subjects who met the criterion at least once/number of subjects within each group who had that parameter assessed For hemoglobin, baseline values <LLN or >ULN (or LLN/ULN missing) are counted in one unique group (ie as normal), for eosinophils, values <LLN (or LLN missing) are counted as normal.

Note:

A PCSA is considered to be on-treatment if it occurred from the time of the first investigational product (IP) administration up to the end of study visit (included).

PGM = PRODOPS/SAR156597/TDU11325/CSR/REPORT/PGM/lab_lbpcsa_s_t.sas

OUT = REPORT/OUTPUT/lab_lbpcsa_s_t_hem_i.rtf (08MAR2012 - 15:33)

TABLE 26

Biochemistry - Number of subjects with abnormalities (PCSA) during the TEAE period according to baseline status - safety population

| | Placebo (N = 12) | | 10 mg (N = 6) | | 20 mg (N = 6) | | 40 mg (N = 6) | | 80 mg (N = 6) | | 150 mg (N = 6) | | 300 mg (N = 6) | |
|---|---|---|---|---|---|---|---|---|---|---|---|---|---|---|
| Laboratory parameter PCSA criteria n/N1 | Nor. bas. | Abn. bas. | Nor. bas. | Abn. bas. | Nor. bas. | Abn. bas. | Nor. bas. | Abn. bas. | Nor. bas. | Abn. bas. | Nor. bas. | Abn. bas. | Nor. bas. | Abn. bas. |
| Glucose | | | | | | | | | | | | | | |
| ≤3.9 mmol/L and <LLN | 1/12 | 0/0 | 1/6 | 0/0 | 0/5 | 1/1 | 0/6 | 0/0 | 1/6 | 0/0 | 0/6 | 0/0 | 1/5 | 0/1 |
| ≥11.1 mmol/L (unfasted); ≥7 mmol/L (fasted) | 0/12 | 0/0 | 0/6 | 0/0 | 0/5 | 0/1 | 0/6 | 0/0 | 0/6 | 0/0 | 0/6 | 0/0 | 0/5 | 0/1 |
| Total cholesterol | | | | | | | | | | | | | | |
| ≥7.74 mmol/L | 0/8 | 0/4 | 0/6 | 0/0 | 0/6 | 0/0 | 0/4 | 0/2 | 0/5 | 0/1 | 0/6 | 0/0 | 0/4 | 0/2 |
| Triglycerides | | | | | | | | | | | | | | |
| ≥4.6 mmol/L | 0/10 | 2/2 | 0/6 | 0/0 | 0/6 | 0/0 | 0/4 | 2/2 | 0/6 | 0/0 | 0/5 | 0/1 | 1/4 | 0/2 |
| Creatine phospho kinase | | | | | | | | | | | | | | |
| >3 ULN | 1/12 | 0/0 | 0/6 | 0/0 | 1/5 | 0/1 | 0/6 | 0/0 | 0/5 | 0/1 | 0/4 | 1/2 | 1/6 | 0/0 |
| >10 ULN | 1/12 | 0/0 | 0/6 | 0/0 | 0/5 | 0/1 | 0/6 | 0/0 | 0/5 | 0/1 | 0/4 | 0/2 | 1/6 | 0/0 |
| Highly sensitive c-reactive protein | | | | | | | | | | | | | | |
| >2 ULN | 1/12 | 0/0 | 1/6 | 0/0 | 0/6 | 0/0 | 0/6 | 0/0 | 0/6 | 0/0 | 1/6 | 0/0 | 1/6 | 0/0 |
| Sodium | | | | | | | | | | | | | | |
| ≤129 mmol/L | 0/12 | 0/0 | 0/6 | 0/0 | 0/6 | 0/0 | 0/6 | 0/0 | 0/6 | 0/0 | 0/6 | 0/0 | 0/6 | 0/0 |
| ≥160 mmol/L | 0/12 | 0/0 | 0/6 | 0/0 | 0/6 | 0/0 | 0/6 | 0/0 | 0/6 | 0/0 | 0/6 | 0/0 | 0/6 | 0/0 |
| Potassium | | | | | | | | | | | | | | |
| <3 mmol/L | 0/12 | 0/0 | 0/6 | 0/0 | 0/6 | 0/0 | 0/6 | 0/0 | 0/6 | 0/0 | 0/6 | 0/0 | 0/6 | 0/0 |
| ≥5.5 mmol/L | 0/12 | 0/0 | 0/6 | 0/0 | 0/6 | 0/0 | 0/6 | 0/0 | 0/6 | 0/0 | 0/6 | 0/0 | 0/6 | 0/0 |
| Creatinine | | | | | | | | | | | | | | |
| ≥150 μmol/L (Adults) | 0/12 | 0/0 | 0/6 | 0/0 | 0/6 | 0/0 | 0/6 | 0/0 | 0/6 | 0/0 | 0/6 | 0/0 | 0/6 | 0/0 |
| ≥30% change from B | 0/12 | na | 0/6 | na | 0/6 | na | 0/6 | na | 0/6 | na | 0/6 | na | 0/6 | na |
| ALT (SGPT-ALAT) | | | | | | | | | | | | | | |
| >3 ULN | 0/12 | 0/0 | 0/6 | 0/0 | 0/6 | 0/0 | 0/6 | 0/0 | 0/6 | 0/0 | 0/6 | 0/0 | 0/6 | 0/0 |
| AST (SGOT-ASAT) | | | | | | | | | | | | | | |
| >3 ULN | 1/12 | 0/0 | 0/6 | 0/0 | 0/6 | 0/0 | 0/6 | 0/0 | 0/6 | 0/0 | 0/6 | 0/0 | 0/6 | 0/0 |
| >5 ULN | 1/12 | 0/0 | 0/6 | 0/0 | 0/6 | 0/0 | 0/6 | 0/0 | 0/6 | 0/0 | 0/6 | 0/0 | 0/6 | 0/0 |
| >10 ULN | 0/12 | 0/0 | 0/6 | 0/0 | 0/6 | 0/0 | 0/6 | 0/0 | 0/6 | 0/0 | 0/6 | 0/0 | 0/6 | 0/0 |
| Alkaline phosphatase | | | | | | | | | | | | | | |
| >1.5 ULN | 0/12 | 0/0 | 0/6 | 0/0 | 0/6 | 0/0 | 0/6 | 0/0 | 0/6 | 0/0 | 0/6 | 0/0 | 0/6 | 0/0 |
| Total bilirubin | | | | | | | | | | | | | | |
| >1.5 ULN | 0/12 | 0/0 | 0/6 | 0/0 | 0/6 | 0/0 | 1/5 | 1/1 | 0/6 | 0/0 | 0/6 | 0/0 | 0/6 | 0/0 |
| >2 ULN | 0/12 | 0/0 | 0/6 | 0/0 | 0/6 | 0/0 | 0/5 | 0/1 | 0/6 | 0/0 | 0/6 | 0/0 | 0/6 | 0/0 |

PCSA: Potentially Clinically Significant Abnormalities (Version of 14 Sep. 2009)
LLN/ULN = Lower/Upper Limit of Normal range,
B = Baseline,
Nor. bas. = Normal baseline,
Abn. bas. = Abnormal baseline (LLN/ULN or PCSA),
Miss. bas. = Missing baseline,
na = not applicable
n/N1 = number of subjects who met the criterion at least once/number of subjects within each group who had that parameter assessed
For % change creatinine, baseline values <LLN or >ULN (or LLN/ULN missing) are counted in one unique group (ie as normal), for CPK, ALT, AST, ALP and Total Bilirubin, values <LLN (or LLN missing) are counted as normal.
Note:
A PCSA is considered to be on-treatment if it occurred from the time of the first investigational product (IP) administration up to the end of study visit (included).
PGM = PRODOPS/SAR156597/TDU11325/CSR/REPORT/PGM/lab_lbpcsa_s_t.sas
OUT = REPORT/OUTPUT/lab_lbpcsa_s_t_bio_i.rtf (08MAR2012 - 15:32)

TABLE 27

Listing of subjects with combined PCSAs
for liver function - safety population

| No occurrence | 5 |
|---|---|

PCSA: Potentially Clinically Significant Abnormalities (Version of 14 SEP. 2009)
ULN = Upper Limit of Normal range,
r = rechecked values,
B = Baseline value
* = ALT >3 ULN and Total bilirubin >2 ULN during the study, with at least one of them being post dose
# = Conjugated Bilirubin >35% Total bilirubin and Total Bilirubin >1.5 ULN on the same sample post dose
+/++ = Abnormal value reaching a $1^{st}/2^{nd}$ upper PCSA limit
Note:
A PCSA is considered to be on-treatment if it occurred from the time of the first investigational product (IP) administration up to the end of study visit (included).
PGM = PRODOPS/SAR156597/TDU11325/CSR/REPORT/PGM/lab_lbhep_s_l.sas
OUT = REPORT/OUTPUT/lab_lbhep_s_l_i.rtf (8 MAR. 2012 - 15:33)

TABLE 28

Listing of hsCRP >10 mg/L for at least 72 hours

| Treatment group | Subject | Visit | Theor. time | Sample Date | Sample Time | Lab. code | hsCRP (mg/L) |
|---|---|---|---|---|---|---|---|
| SAR156597 150 mg | 840001039 | D −1 | | 2011 Jun. 7 | 09:57 | 840000276 | 0.8B |
| | | D 1 | T8 H | 2011 Jun. 8 | 16:25 | 840000276 | 0.5 |
| | | D 2 | T24 H | 2011 Jun. 9 | 08:25 | 840000276 | 0.5 |
| | | D 3 | T48 H | 2011 Jun. 10 | 08:25 | 840000276 | 0.5 |
| | | D 4 | T72 H | 2011 Jun. 11 | 08:38 | 840000276 | 0.7 |
| | | D 5 | | 2011 Jun. 12 | 08:14 | 840000276 | 0.7 |
| | | D 8 | | 2011 Jun. 15 | 08:53 | 840000276 | 0.8 |
| | | D 15 | | 2011 Jun. 22 | 09:00 | 840000276 | 1.6 |
| | | D 29 | | 2011 Jul. 6 | 10:10 | 840000276 | 18.8H+ |
| | | | r | 2011 Jul. 14 | 11:44 | 840000276 | 13.9H+ |
| | | D 57 | | 2011 Aug. 3 | 10:13 | 840000276 | 1.2 |
| | | EOS | | 2011 Aug. 31 | 10:25 | 840000276 | 0.9 |
| | | | r | 2011 Oct. 13 | 10:36 | 840000276 | 2.2 |
| | | FUP | | 2011 Dec. 1 | 10:56 | 840000276 | 1.3 |
| | | | r | 2012 Feb. 6 | 10:59 | 840000276 | 0.8 |
| SAR156597 300 mg | 840001046 | D −1 | | 2011 Nov. 15 | 08:05 | 840000276 | 0.4B |
| | | D 1 | T8 H | 2011 Nov. 16 | 17:35 | 840000276 | 0.4 |
| | | D 2 | T24 H | 2011 Nov. 17 | 09:35 | 840000276 | 0.3 |
| | | D 3 | T48 H | 2011 Nov. 18 | 09:35 | 840000276 | 0.2 |
| | | D 4 | T72 H | 2011 Nov. 19 | 09:35 | 840000276 | 0.6 |
| | | D 5 | | 2011 Nov. 20 | 09:35 | 840000276 | 0.6 |
| | | D 8 | | 2011 Nov. 23 | 08:14 | 840000276 | 0.3 |
| | | D 15 | | 2011 Nov. 30 | 08:21 | 840000276 | 0.3 |
| | | D 29 | | 2011 Dec. 14 | 08:21 | 840000276 | 0.7 |
| | | D 57 | | 2012 Jan. 11 | 08:25 | 840000276 | 0.3 |
| | | EOS | | 2012 Feb. 8 | 08:32 | 840000276 | 37.0H+ |
| | | | r | 2012 Feb. 10 | 07:55 | 840000276 | 91.5H+ |
| | | | r | 2012 Feb. 13 | 08:17 | 840000276 | 23.6H+ |
| | | | r | 2012 Feb. 27 | 08:07 | 840000276 | 0.5 |

L or H: Abnormal value <LLN or >ULN,
−/−− or +/++: Abnormal value reaching a 1st/2nd lower or a 1st/2nd upper PCSA limit
PCSA: Potentially Clinically Significant Abnormalities (Version of 14 Sep. 2009)
LLN/ULN = Lower/Upper Limit of Normal range,
r = rechecked values,
B = Baseline value
Baseline is Day −1
PGM = PRODOPS/SAR156597/TDU11325/CSR/REPORT/PGM/lab_hscrp_s_l.sas
OUT = REPORT/OUTPUT/lab_hscrp_s_l_1_i.rtf (08MAR2012 - 15:34)

TABLE 29

Listing of subjects with hsCRP >20 mg/L for 2 consecutive blood collections >=24 hours apart

| Treatment group | Subject | Visit | Theor. time | Sample Date | Sample Time | Lab. code | hsCRP (mg/L) |
|---|---|---|---|---|---|---|---|
| SAR156597 300 mg | 840001046 | D −1 | | 2011 Nov. 15 | 08:05 | 840000276 | 0.4B |
| | | D 1 | T8 H | 2011 Nov. 16 | 17:35 | 840000276 | 0.4 |
| | | D 2 | T24 H | 2011 Nov. 17 | 09:35 | 840000276 | 0.3 |

TABLE 29-continued

Listing of subjects with hsCRP >20 mg/L for 2 consecutive blood collections >=24 hours apart

| Treatment group | Subject | Visit | Theor. time | Sample Date | Time | Lab. code | hsCRP (mg/L) |
|---|---|---|---|---|---|---|---|
| | | D 3 | T48 H | 2011 Nov. 18 | 09:35 | 840000276 | 0.2 |
| | | D 4 | T72 H | 2011 Nov. 19 | 09:35 | 840000276 | 0.6 |
| | | D 5 | | 2011 Nov. 20 | 09:35 | 840000276 | 0.6 |
| | | D 8 | | 2011 Nov. 23 | 08:14 | 840000276 | 0.3 |
| | | D 15 | | 2011 Nov. 30 | 08:21 | 840000276 | 0.3 |
| | | D 29 | | 2011 Dec. 14 | 08:21 | 840000276 | 0.7 |
| | | D 57 | | 2012 Jan. 11 | 08:25 | 840000276 | 0.3 |
| | | EOS | | 2012 Feb. 8 | 08:32 | 840000276 | 37.0H+ |
| | | r | | 2012 Feb. 10 | 07:55 | 840000276 | 91.5H+ |
| | | r | | 2012 Feb. 13 | 08:17 | 840000276 | 23.6H+ |
| | | r | | 2012 Feb. 27 | 08:07 | 840000276 | 0.5 |

PGM = PRODOPS/SAR156597/TDU11325/CSR/REPORT/PGM/lab_hscrp_s_l.sas
OUT = REPORT/OUTPUT/lab_hscrp_s_l_2_i.rtf (08MAR2012 - 15:34)

TABLE 30

Listing of subjects with cTnI > 2ULN

No occurrence

L or H: Abnormal value <LLN or >ULN,
−/−− or +/++: Abnormal value reaching a 1st/2nd lower or a 1st/2nd upper PCSA limit
cTnI = Cardiac Troponin I
PGM = PRODOPS/SAR156597/TDU11325/CSR/REPORT/PGM/lab_lbctnl_s_l.sas
OUT = REPORT/OUTPUT/lab_lbctnl_s_l_i.rtf (08 MAR. 2012 - 15:34)

TABLE 31

Vital signs - Number of subjects with abnormalities (PCSA) during the TEAE period - safety population

| Vital signs parameter PCSA criteria n/N1 | Placebo (N = 12) | SAR156597 10 mg (N = 6) | 20 mg (N = 6) | 40 mg (N = 6) | 80 mg (N = 6) | 150 mg (N = 6) | 300 mg (N = 6) |
|---|---|---|---|---|---|---|---|
| Systolic blood pressure | | | | | | | |
| ≤95 mmHg and decr. from B ≥20 mmHg | 0/12 | 0/6 | 0/6 | 0/6 | 0/6 | 0/6 | 0/6 |
| ≥140 mmHg and incr. from B ≥20 mmHg | 0/12 | 0/6 | 0/6 | 0/6 | 0/6 | 0/6 | 1/6 |
| Diastolic blood pressure | | | | | | | |
| ≤45 mmHg and decr. from B ≥10 mmHg | 0/12 | 1/6 | 0/6 | 0/6 | 0/6 | 0/6 | 0/6 |
| ≥90 mmHg and incr. from B ≥10 mmHg | 0/12 | 0/6 | 0/6 | 0/6 | 0/6 | 0/6 | 0/6 |
| Orthostatic systolic blood pressure | | | | | | | |
| ≤−20 mmHg | 0/12 | 1/6 | 1/6 | 1/6 | 0/6 | 1/6 | 1/6 |
| Orthostatic diastolic blood pressure | | | | | | | |
| ≤−10 mmHg | 0/12 | 1/6 | 1/6 | 1/6 | 1/6 | 1/6 | 1/6 |
| Heart rate | | | | | | | |
| ≤40 bpm and decr. from B ≥20 bpm | 0/12 | 0/6 | 0/6 | 0/6 | 0/6 | 0/6 | 0/6 |
| ≥100 bpm and incr. from B ≥20 bpm | 0/12 | 0/6 | 0/6 | 0/6 | 0/6 | 0/6 | 0/6 |
| Weight | | | | | | | |
| ≥5% decr. from B | 2/12 | 0/6 | 0/6 | 0/6 | 0/6 | 0/6 | 0/6 |
| ≥5% incr. from B | 0/12 | 0/6 | 0/6 | 0/6 | 2/6 | 0/6 | 0/6 |

PCSA: Potentially Clinically Significant Abnormalities (Version of 14 Sep. 2009)
decr./incr. = decrease/increase,
B = Baseline
n/N1 = Number of subjects who met the criterion at least once/number of subjects within each group who had that parameter assessed
Note:
A PCSA is considered to be on-treatment if it occurred from the time of the first investigational product (IP) administration up to the end of study visit (included).
Orthostatic = standing after 3 minutes - supine after 10 minutes
PGM = PRODOPS/SAR156597/TDU11325/CSR/REPORT/PGM/osa_vspcsa_s_t.sas
OUT = REPORT/OUTPUT/osa_vspcsa_s_t_i.rtf (08MAR2012 - 15:34)

TABLE 32

ECG - Number of subjects with abnormalities (PCSA) during the TEAE period - safety population

| ECG parameter (automatic reading) PCSA criteria n/N1 | Placebo (N = 12) | SAR156597 | | | | | |
|---|---|---|---|---|---|---|---|
| | | 10 mg (N = 6) | 20 mg (N = 6) | 40 mg (N = 6) | 80 mg (N = 6) | 150 mg (N = 6) | 300 mg (N = 6) |
| Heart rate | | | | | | | |
| ≤40 bpm and decr. from B ≥20 bpm | 0/12 | 0/6 | 0/6 | 0/6 | 0/6 | 0/6 | 0/6 |
| ≥100 bpm and incr. from B ≥20 bpm | 0/12 | 0/6 | 0/6 | 0/6 | 0/6 | 0/6 | 0/6 |
| PR interval | | | | | | | |
| ≥220 ms | 1/12 | 1/6 | 0/6 | 0/6 | 0/6 | 0/6 | 0/6 |
| QRS interval | | | | | | | |
| ≥20 ms | 1/12 | 0/6 | 2/6 | 0/6 | 0/6 | 0/6 | 0/6 |
| QTc interval | | | | | | | |
| Borderline: 431-450 ms (Male); 451-470 ms (Female) | 3/12 | 0/6 | 0/6 | 2/6 | 1/6 | 3/6 | 0/6 |
| Prolonged: >450 ms (Male); >470 ms (Female) | 0/12 | 0/6 | 0/6 | 0/6 | 0/6 | 0/6 | 0/6 |
| ≥500 ms | 0/12 | 0/6 | 0/6 | 0/6 | 0/6 | 0/6 | 0/6 |
| QTc interval - change from baseline | | | | | | | |
| Borderline: Incr. from B 30-60 ms | 2/12 | 2/6 | 1/6 | 1/6 | 1/6 | 0/6 | 0/6 |
| Prolonged: Incr. from B >60 ms | 0/12 | 0/6 | 0/6 | 0/6 | 0/6 | 0/6 | 0/6 |

PCSA: Potentially Clinically Significant Abnormalities (Version of 14 Sep. 2009)
decr./incr. = decrease/increase,
B = Baseline
n/N1 = number of subjects who met the criterion at least once/number of subjects within each group who had that parameter assessed
Note:
A PCSA is considered to be on-treatment if it occurred from the time of the first investigational product (IP) administration up to the end of study visit (included).
PGM = PRODOPS/SAR156597/TDU11325/CSR/REPORT/PGM/osa_egpcsa_s_t.sas
OUT = REPORT/OUTPUT/osa_egpcsa_s_t_i.rtf (08MAR2012-15:33)

TABLE 33

Listing of subjects with prolonged QTc and/or delta QTc >60 ms (automatic reading) - safety population

| No occurrence |
|---|

PCSA: Potentially Clinically Significant Abnormalities (Version of 14 SEP. 2009)
B = Baseline,
Delta = change from baseline (B),
r = rechecked values
− or +/++: Abnormal value reaching the lower or a $1^{st}/2^{nd}$ upper PCSA limit
Note:
Baseline is defined as the mean of triplicates at D1 predose.
Note:
A PCSA is considered to be on-treatment if it occurred from the time of the first investigational product (IP) administration up to the end of study visit(included).
PGM = PRODOPS/SAR156597/TDU11325/CSR/REPORT/PGM/osa_egauprol_s_l.sas
OUT = REPORT/OUTPUT/osa_egauprol_s_l_i.rtf (8 MAR. 2012 -15:33)

TABLE 34

Total IgE - Descriptive statistics

| | Raw data | | | | | | % Change from baseline | | | | | |
|---|---|---|---|---|---|---|---|---|---|---|---|---|
| | N | Mean | SD | SEM | Median | Min | Max | N | Mean | SD | SEM | Median | Min | Max |
| Placebo | | | | | | | | | | | | | | |
| Baseline | 12 | 80.70 | 109.71 | 31.672 | 35.75 | 1.0 | 397.0 | | | | | | |
| D 2 T24 H | 12 | 85.87 | 121.41 | 35.049 | 36.90 | 1.0 | 435.0 | 12 | 2.26 | 11.32 | 3.267 | 3.27 | −25.6 | 19.7 |
| D 15 | 12 | 82.64 | 112.33 | 32.427 | 35.40 | 1.0 | 393.0 | 12 | −1.40 | 11.83 | 3.416 | −0.84 | −19.2 | 30.3 |
| D 29 | 12 | 76.58 | 109.84 | 31.709 | 34.95 | 1.0 | 402.0 | 12 | −6.06 | 10.09 | 2.912 | −2.98 | −23.2 | 6.0 |
| EOS | 12 | 76.26 | 103.95 | 30.007 | 32.70 | 1.0 | 386.0 | 12 | 7.74 | 44.99 | 12.988 | −1.39 | −31.0 | 142.4 |

TABLE 34-continued

Total IgE - Descriptive statistics

| | Raw data | | | | | | % Change from baseline | | | | | |
|---|---|---|---|---|---|---|---|---|---|---|---|---|
| | N | Mean | SD | SEM | Median | Min | Max | N | Mean | SD | SEM | Median | Min | Max |

| | N | Mean | SD | SEM | Median | Min | Max | N | Mean | SD | SEM | Median | Min | Max |
|---|---|---|---|---|---|---|---|---|---|---|---|---|---|---|
| SAR156597 10 mg | | | | | | | | | | | | | | |
| Baseline | 6 | 26.18 | 11.65 | 4.754 | 24.70 | 14.3 | 40.1 | | | | | | | |
| D 2 T24 H | 6 | 26.67 | 11.66 | 4.760 | 25.50 | 14.4 | 39.8 | 6 | 2.12 | 3.13 | 1.280 | 0.67 | −0.7 | 7.8 |
| D 15 | 6 | 23.27 | 9.44 | 3.854 | 20.15 | 14.8 | 38.5 | 6 | −7.25 | 17.53 | 7.157 | −3.27 | −41.8 | 7.7 |
| D 29 | 6 | 22.43 | 9.01 | 3.678 | 19.90 | 14.5 | 38.1 | 6 | −10.02 | 18.40 | 7.511 | −5.72 | −45.0 | 5.6 |
| EOS | 6 | 23.55 | 9.76 | 3.983 | 22.05 | 14.1 | 39.2 | 6 | −7.51 | 13.14 | 5.365 | −4.31 | −33.1 | 4.4 |
| SAR156597 20 mg | | | | | | | | | | | | | | |
| Baseline | 6 | 198.60 | 434.00 | 177.179 | 27.30 | 1.0 | 1084.0 | | | | | | | |
| D 2 T24 H | 6 | 192.57 | 420.30 | 171.585 | 27.60 | 1.0 | 1050.0 | 6 | −1.85 | 5.59 | 2.284 | −2.00 | −8.9 | 7.4 |
| D 15 | 6 | 163.95 | 352.56 | 143.931 | 23.85 | 1.0 | 883.0 | 6 | −8.53 | 8.76 | 3.578 | −8.13 | −18.5 | 2.0 |
| D 29 | 6 | 161.83 | 346.71 | 141.545 | 25.35 | 1.0 | 869.0 | 6 | −6.62 | 7.02 | 2.865 | −4.80 | −19.8 | 0.0 |
| EOS | 6 | 179.87 | 393.19 | 160.519 | 23.50 | 1.0 | 982.0 | 6 | −8.19 | 7.64 | 3.118 | −6.24 | −20.0 | 0.0 |
| SAR156597 40 mg | | | | | | | | | | | | | | |
| Baseline | 6 | 134.77 | 191.25 | 78.076 | 67.50 | 19.2 | 516.0 | | | | | | | |
| D 2 T24 H | 6 | 139.22 | 202.79 | 82.789 | 64.70 | 19.8 | 545.0 | 6 | 1.61 | 4.05 | 1.653 | 2.68 | −6.2 | 5.6 |
| D 15 | 5 | 125.94 | 178.28 | 79.730 | 31.00 | 20.5 | 437.0 | 5 | −1.33 | 8.59 | 3.841 | 1.75 | −15.3 | 6.8 |
| D 29 | 5 | 125.32 | 186.47 | 83.390 | 31.30 | 19.2 | 454.0 | 5 | −5.70 | 6.91 | 3.091 | −2.19 | −14.3 | 0.0 |
| EOS | 6 | 129.82 | 172.61 | 70.467 | 73.85 | 25.0 | 477.0 | 6 | 28.14 | 85.72 | 34.994 | −4.40 | −14.4 | 202.6 |
| SAR156597 80 mg | | | | | | | | | | | | | | |
| Baseline | 6 | 56.05 | 44.60 | 18.207 | 50.85 | 7.2 | 118.0 | | | | | | | |
| D 2 T24 H | 6 | 56.03 | 46.43 | 18.954 | 50.10 | 3.8 | 119.0 | 6 | −7.61 | 19.58 | 7.995 | 0.63 | −47.2 | 3.8 |
| D 15 | 6 | 53.33 | 40.62 | 16.585 | 56.65 | 3.9 | 103.0 | 6 | −9.13 | 21.02 | 8.582 | −7.95 | −45.8 | 17.7 |
| D 29 | 6 | 56.83 | 44.87 | 18.320 | 60.00 | 3.0 | 114.0 | 6 | −6.92 | 28.41 | 11.598 | −4.14 | −58.3 | 29.2 |
| EOS | 6 | 56.60 | 43.95 | 17.942 | 59.95 | 2.8 | 114.0 | 6 | −2.35 | 36.51 | 14.904 | −7.33 | −61.1 | 37.4 |
| SAR156597 150 mg | | | | | | | | | | | | | | |
| Baseline | 6 | 38.67 | 28.37 | 11.582 | 32.45 | 13.0 | 93.8 | | | | | | | |
| D 2 T24 H | 6 | 38.67 | 27.72 | 11.315 | 31.40 | 11.7 | 91.0 | 6 | −0.47 | 9.00 | 3.674 | −2.91 | −10.0 | 16.6 |
| D 15 | 6 | 36.07 | 26.61 | 10.862 | 30.95 | 10.6 | 87.1 | 6 | −7.95 | 6.29 | 2.569 | −8.09 | −18.5 | 0.0 |
| D 29 | 6 | 47.43 | 51.09 | 20.857 | 31.15 | 12.1 | 150.0 | 6 | 7.12 | 26.56 | 10.844 | −1.30 | −11.4 | 59.9 |
| EOS | 6 | 39.95 | 29.18 | 11.912 | 30.65 | 13.0 | 96.4 | 6 | 3.86 | 12.13 | 4.952 | 4.23 | −16.3 | 20.0 |
| SAR156597 300 mg | | | | | | | | | | | | | | |
| Baseline | 6 | 51.15 | 62.93 | 25.689 | 24.45 | 20.0 | 179.0 | | | | | | | |
| D 2 T24 H | 6 | 48.52 | 61.22 | 24.992 | 21.60 | 20.3 | 173.0 | 6 | −6.57 | 6.20 | 2.532 | −6.57 | −16.9 | 2.0 |
| D 15 | 6 | 37.43 | 42.19 | 17.223 | 21.75 | 14.4 | 123.0 | 6 | −21.12 | 18.99 | 7.753 | −28.65 | −31.3 | 17.4 |
| D 29 | 6 | 36.47 | 39.32 | 16.051 | 20.85 | 15.1 | 116.0 | 6 | −21.67 | 16.26 | 6.637 | −26.71 | −35.2 | 10.1 |
| EOS | 6 | 50.30 | 56.09 | 22.900 | 22.95 | 13.7 | 158.0 | 6 | 0.82 | 38.97 | 15.909 | −10.03 | −31.5 | 78.0 |

N corresponds to the count of subjects with available data
Baseline is the Day −1 value
Values below LOQ (Limit Of Quantification) were replaced by LOQ/2
PGM = PRODOPS/SAR156597/TDU11325/CSR/REPORT/PGM/pd_lbsum_s_t.sas
OUT = REPORT/OUTPUT/pd_lbsum_s_t_1_i.rtf (08MAR2012 - 15:35

TABLE 35

Pharmacokinetic parameters for plasma concentration of SAR156597 after a single subcutaneous dose given to young healthy male subjects (TDU11325)

| | Mean ± SD (Geometric Mean) [CV %] Plasma SAR156597 | | | | | |
|---|---|---|---|---|---|---|
| | 10 mg | 20 mg | 40 mg | 80 mg | 150 mg | 300 mg |
| N | 6 | 6 | 5 | 6 | 6 | 6 |
| $C_{max}$ (µg/ml) | 0.971 ± 0.254 (0.943) [26.1] | 1.69 ± 0.222 (1.67) [13.1] | 3.32 ± 0.797 (3.25) [24.0] | 7.01 ± 1.97 (6.81) [28.1] | 9.44 ± 1.78 (9.29) [18.9] | 24.1 ± 4.60 (23.8) [19.0] |
| $t_{max}^{a}$ (hr) | 108 (48-168) | 96 (73-170) | 119 (48-240) | 144 (72-240) | 168 (120-240) | 96 (71-168) |
| $t_{1/2z}$ (hr) | 369 ± 106 (355) [28.6] | 350 ± 54.4 (345) [15.6] | 320 ± 34.8 (319) [10.9] | 372 ± 104 (358) [27.9] | 464 ± 72.0 (460) [15.5] | 315 ± 71.4 (308) [22.7] |
| $AUC_{last}$ | 607 ± 174 | 1000 ± 295 | 1920 ± 377 | 3670 ± 1100 | 5570 ± 761 | 11300 ± 2900 |

TABLE 35-continued

Pharmacokinetic parameters for plasma concentration of SAR156597 after a single subcutaneous dose given to young healthy male subjects (TDU11325)

| | Mean ± SD (Geometric Mean) [CV %] Plasma SAR156597 | | | | | |
|---|---|---|---|---|---|---|
| | 10 mg | 20 mg | 40 mg | 80 mg | 150 mg | 300 mg |
| (μg · hr/ml) | (587) [28.7] | (967) [29.4] | (1890) [19.6] | (3530) [30.0] | (5530) [13.7] | (10900) [25.7] |
| AUC | 644 ± 185 | 1050 ± 297 | 1960 ± 378 | 3780 ± 1140 | 5820 ± 844 | 11500 ± 3000 |
| (μg · hr/ml) | (622) [28.7] | (1010) [28.3] | (1930) [19.3] | (3630) [30.2] | (5770) [14.5] | (11100) [26.1] |
| $V_{ss}/F$ | 9230 ± 2400 | 11400 ± 2370 | 10700 ± 1740 | 11400 ± 2870 | 16500 ± 2270 | 13100 ± 2300 |
| (ml) | (8990) [26.0] | (11100) [20.9] | (10600) [16.2] | (11100) [25.1] | (16300) [13.8] | (12900) [17.6] |
| CL/F | 16.6 ± 4.55 | 20.4 ± 5.86 | 21.0 ± 4.05 | 23.0 ± 7.62 | 26.2 ± 3.66 | 28.2 ± 10.2 |
| (ml/hr) | (16.1) [27.4] | (19.7) [28.7] | (20.7) [19.2] | (22.0) [33.1] | (26.0) [14.0] | (27.0) [36.2] |
| $t_{last}{}^a$ | 1679 | 1680 | 1704 | 2016 | 2020 | 2016 |
| (hr) | (1008-2016) | (1345-2016) | (1633-2016) | (1368-2018) | (2014-2111) | (1344-2039) |

$^a$Median (Min-Max)
NA = Not Applicable
Source = PKS Study: TDU11325 DBLII E02; Scenario: P-D-EV-SD-E02, Version 1
Date/Time = 3 Jun. 2012 11:25:36 AM

---

The invention claimed is:

1. A stable lyophilized antibody formulation comprising: 100 mg/mL of a bispecific antibody or a bispecific antigen binding fragment thereof, wherein the bispecific antibody or bispecific antibody fragment comprises a light chain variable domain $VL_{hB-B13}$, a light chain variable domain $VL_{hBD4-8}$, a heavy chain variable domain $VH_{hB-B13}$ and a heavy chain variable domain $VH_{hBD4-8}$, wherein:

$VL_{hB-B13}$ comprises CDRs comprising the amino acid sequences RASESVDSYGQSYMH (SEQ ID NO:8), LASNLES (SEQ ID NO:9), and QQNAEDSRT (SEQ ID NO:10);

$VL_{hBD4-8}$ comprises CDRs comprising the amino acid sequences HASQNIDVWLS (SEQ ID NO:14), KASNLHTG (SEQ ID NO:15), and QQAHSYPFT (SEQ ID NO:16), $VH_{hB-B13}$ comprises CDRs comprising the amino acid sequences GFSLTDSSIN (SEQ ID NO:11), DGRID (SEQ ID NO:12), and DGYFPYAMDF (SEQ ID NO:13), $VH_{hBD4-8}$ comprises CDRs comprising the amino acid sequences GYSFTSYWIH (SEQ ID NO:17), IDPSDGETR (SEQ ID NO:18) and LKEYGNYDSFYFDV (SEQ ID NO:19) or the amino acid sequences GYSFTSYWIH (SEQ ID NO:20), IDASDGETR (SEQ ID NO:21), and LKEYGNYDSFYFDV (SEQ ID NO:22);

10 mM of a buffering system, wherein the buffering system comprises a tromethamine buffer concentration of 3.7 mM and a monobasic sodium phosphate buffer concentration of 6.3 mM;

0.2% (w/v) polysorbate 80;

5% (w/v) sucrose; and

3% (w/v) proline;

wherein the pH of the formulation is about pH 7.

2. The formulation of claim 1, wherein the bispecific antibody or fragment thereof comprises a heavy chain variable region comprising the amino acid sequences of SEQ ID NOs: 2 and 4, and a light chain variable region comprising the amino acid sequences of SEQ ID NOs: 1 and 3.

3. The formulation of claim 1, wherein the bispecific antibody or fragment thereof comprises a heavy chain variable region comprising the amino acid sequences of SEQ ID NOs: 2 and 5, and a light chain variable region comprising the amino acid sequences of SEQ ID NOs: 1 and 3.

4. The formulation of claim 1, wherein:

$VL_{hB-B13}$ comprises an amino acid sequence at least 95% identical to the amino acid sequence of SEQ ID NO:1, $VL_{hBD4-8}$ comprises an amino acid sequence at least 95% identical to the amino acid sequence of SEQ ID NO:3, $VH_{hB-B13}$ comprises an amino acid sequence at least 95% identical to the amino acid sequence of SEQ ID NO:2, $VH_{hBD4-8}$ comprises an amino acid sequence at least 95% identical to the amino acid sequence of SEQ ID NO:4 or SEQ ID NO:5.

5. The formulation of claim 1, wherein the bispecific antibody or bispecific antigen fragment comprises light chains comprising the structure N-$VL_{hB-B13}$-linker-$VL_{hBD4-8}$-CL-C and the heavy chains comprising the structure N-$VH_{hB-B13}$-linker-$VH_{hBD4-8}$-CH1-CH2-CH3-C.

6. The formulation of claim 5, wherein the linker comprises the amino acid sequence of SEQ ID NO:6.

7. The formulation of claim 5, wherein the bispecific antibody or bispecific antibody fragment thereof comprises two light chains and two heavy chains.

8. The formulation of claim 1, wherein the bispecific antibody or bispecific antibody fragment comprises light chains comprising the structure N-$VL_{hBD4-8}$-linker-$VL_{hB-B13}$-CL-C and the heavy chains comprising the structure N-$VH_{hBD4-8}$-linker-$VH_{hB-B13}$-CH1-CH2-CH3-C.

9. The formulation of claim 8, wherein the linker comprises the amino acid sequence of SEQ ID NO:6.

10. The formulation of claim 8, wherein the bispecific antibody or bispecific antibody fragment thereof comprises two light chains and two heavy chains.

11. The formulation of claim 1, wherein the formulation is for administration to an individual in need thereof subcutaneously at a dose of 10 mg to 300 mg.

* * * * *

UNITED STATES PATENT AND TRADEMARK OFFICE
CERTIFICATE OF CORRECTION

PATENT NO. : 11,008,389 B2
APPLICATION NO. : 15/206045
DATED : May 18, 2021
INVENTOR(S) : Florent C. Bender Page 1 of 1

It is certified that error appears in the above-identified patent and that said Letters Patent is hereby corrected as shown below:

On the Title Page

In the Abstract, right-hand column, Lines 1-2: please replace "a dual V region antibody-like region" with --a dual V region antibody-like protein--;

In the Claims

At Column 79, Claim 1, Line 20: please replace "A stable lyophilized antibody formulation" with --A stable antibody formulation--;
At Column 79, Claim 1, Line 23: please replace "or bispecific antibody fragment comprises" with --or bispecific antigen binding fragment thereof comprises--;
At Column 79, Claim 2, Line 55: please replace "antibody or fragment thereof" with --antibody or bispecific antigen binding fragment thereof--;
At Column 80, Claim 3, Line 20: please replace "antibody or fragment thereof" with --antibody or bispecific antigen binding fragment thereof--;
At Column 80, Claim 5, Line 37: please replace "or bispecific antibody fragment thereof" with --or bispecific antigen binding fragment thereof--;
At Column 80, Claim 7, Line 44: please replace "bispecific antibody fragment" with --bispecific antigen binding fragment--;
At Column 80, Claim 8, Line 47: please replace "bispecific antibody fragment" with --bispecific antigen binding fragment--; and
At Column 80, Claim 10, Line 54: please replace "bispecific antibody fragment" with --bispecific antigen binding fragment--.

Signed and Sealed this
Tenth Day of August, 2021

Drew Hirshfeld
*Performing the Functions and Duties of the
Under Secretary of Commerce for Intellectual Property and
Director of the United States Patent and Trademark Office*